United States Patent
Hauel et al.

(10) Patent No.: US 6,362,210 B1
(45) Date of Patent: Mar. 26, 2002

(54) CARBOXYLIC ACID AMIDES, PHARMACEUTICAL COMPOSITIONS CONTAINING THESE COMPOUNDS AND THEIR USE

(75) Inventors: Norbert Hauel, Schemmerhofen; Henning Priepke, Warthausen; Klaus Damm; Andreas Schnapp, both of Biberach, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/618,702

(22) Filed: Jul. 18, 2000

(30) Foreign Application Priority Data

Jul. 27, 1999 (DE) .......................................... 199 35 219

(51) Int. Cl.[7] ..................... A61K 31/4164; A61P 35/00; C07D 233/61
(52) U.S. Cl. ..................... 514/396; 548/338.1; 562/457
(58) Field of Search ..................... 548/338.1; 562/457; 514/396

(56) References Cited

U.S. PATENT DOCUMENTS 3,940,422 A    2/1976   Harita et al.

OTHER PUBLICATIONS

Chemical Abstracts 104:33908 (1986).

*Primary Examiner*—Robert W. Ramsuer
(74) *Attorney, Agent, or Firm*—Robert P. Raymond; Alan R. Stempel; Mary-Ellen M. Devlin

(57) ABSTRACT

Carboxylic acid amides of general formula

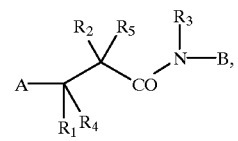

(I)

which inhibit telomerase and are useful for treating tumour diseases such as carcinomas, sarcomas and leukaemias. Exemplary compounds are:

(1) trans-3-(naphth-2-yl)-but-2-enoic acid-N-(2-carboxy-phenyl)-amide, and,
(2) trans-3-(naphth-2-yl)-but-2-enoic acid-N-(2-carboxy-4,5-dimethoxy-phenyl)-amide.

6 Claims, No Drawings

CARBOXYLIC ACID AMIDES, PHARMACEUTICAL COMPOSITIONS CONTAINING THESE COMPOUNDS AND THEIR USE

FIELD OF THE INVENTION

The invention relates to carboxylic acid amides that have an inhibitory effect on telomerase, and their use in the treatment of pathophysiological processes which are characterised by an increased telomerase activity, e.g. tumour diseases such as carcinomas, sarcomas and leukaemias.

BACKGROUND OF THE INVENTION

The last decade of oncological research has made it possible for the first time to achieve a molecular understanding of the regulatory mechanisms involved in the formation of tumours. These include, for example, the function of oncogenes, tumour suppressor genes, growth factors, receptors, signal transduction cascades, pro- and anti-apoptotic genes in controlling cell growth, differentiation, migration and cell death. These new findings have also shown, however, that cancer is a multifactorial disease at the molecular level, during the onset of which tissues may undergo malignant degeneration as a result of different mechanisms. This heterogeneity of the malignant cells in turn explains the clinical problems of tumour therapy.

In 1965 Hayflick postulated (Hayflick, Exp. Cell Res. 37, 614–636 (1965)) that the limited proliferative lifespan of normal somatic cells, replicative senescence, can act as a tumour suppressing mechanism. This hypothesis was supported by experimental work which showed that the overcoming of replicative senescence is a prerequisite for the malignant transformation of cells (Newbold et., al. in Nature, 299, 633–636 (1989); Newbold and Overell in Nature, 304, 648–651 (1983)).

However, only in the last few years has there been any understanding of the molecular mechanisms by which somatic cells achieve the state of replicative senescence.

The ends of eukaryotic chromosomes, the telomers, consist of simple repetitive sequences the integrity of which is essential for the function and structure of the chromosomes. However, linear chromosomes lose a certain length of their telomers in each round of DNA replication, a phenomenon which was recognised by Watson back in 1972 (Watson in Nature New Biol. 239, 197–201 (1972)). The cumulative loss of telomeric DNA over numerous cell divisions constitutes the basis for the limited replicative potential of somatic cells, whereas more than 85% of all tumours in humans reactivate an enzyme, telomerase, in order to compensate for the loss of telomers and thus become immortal (see Shay and Bacchetti in European Journal of Cancer, 33, 787–791 (1997)).

Telomerase in humans is a ribonucleoprotein (RNP) which is made up of at least one catalytic subunit (hTERT), and one RNA (hTR). Both components have been molecularly cloned and characterised. Biochemically, telomerase is a reverse transcriptase which uses a sequence fragment in hTR as matrix in order to synthesise a strand of telomeric DNA (Morin in Cell 59, 521–529 (1989)). Methods of identifying telomerase activity and also methods of diagnosing and treating replicative senescence and immortality by modifying telomers and telomerase have already been described (Morin in Cell 59, 521–529 (1989); Kim et al. in Science 266, 2011–2014 (1994)).

Inhibitors of telomerase can be used for tumour therapy since somatic cells, unlike tumour cells, are not dependent on telomerase.

Moreover, U.S. Pat. No. 3,940,422 inter alia describes the compound trans-3,4-dimethoxy-cinnamic acid-N-anthranilic acid-amide which has antiallergenic properties in particular.

DESCRIPTION OF THE INVENTION

It has now been found that the carboxylic acid amides of general formula

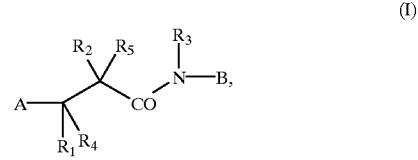

(I)

the isomers thereof, particularly the trans-isomers thereof, and the salts thereof, particularly the physiologically acceptable salts thereof, surprisingly have an inhibitory effect on telomerase.

In the above general formula I $R_1$ denotes a hydrogen atom, a $C_{1-3}$-alkyl or trifluoromethyl group, $R_2$ denotes a hydrogen, fluorine, chlorine or bromine atom, a $C_{1-3}$-alkyl, $C_{3-7}$-cycloalkyl or $C_{1-3}$-alkoxy group or also, if $R_4$ and $R_5$ each denote a hydrogen atom, $R_1$ and $R_2$ together denote an n-$C_{1-3}$-alkylene group optionally substituted by a $C_{1-3}$-alkyl group, $R_3$ denotes a hydrogen atom or a $C_{1-5}$-alkyl group, $R_4$ and $R_5$ each denote a hydrogen atom or together denote another carbon-carbon bond, A denotes a phenyl, naphthyl or tetrahydronaphthyl group substituted by a fluorine, chlorine, bromine or iodine atom, by a $C_{1-6}$-alkyl, $C_{3-7}$-cycloalkyl, phenyl, $C_{1-3}$-alkoxy, cyano, trifluoromethyl or nitro group, whilst the abovementioned monosubstituted phenyl and naphthyl groups may additionally be substituted by a fluorine, chlorine or bromine atom, by a $C_{1-3}$-alkyl or $C_{1-3}$-alkoxy group and the abovementioned disubstituted phenyl groups may additionally be substituted by a $C_{1-3}$-alkyl or $C_{1-3}$-alkoxy group, a naphthyl group, a chromane or chromene group wherein a methylene group may be replaced by a carbonyl group, a 5- or 6-membered heteroaryl group optionally substituted in the carbon skeleton by a fluorine, chlorine or bromine atom, by a $C_{1-3}$-alkyl or $C_{1-3}$-alkoxy group, whilst the 6-membered heteroaryl groups contain one, two or three nitrogen atoms and the 5-membered heteroaryl groups contain an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and additionally a phenyl ring may be fused to the abovementioned monocyclic heteroaryl groups via two adjacent carbon atoms whilst said phenyl ring may also be substituted in the carbon skeleton by a fluorine, chlorine or bromine atom, by a $C_{1-3}$-alkyl or $C_{1-3}$-alkoxy group, a phenylvinyl group or $R_1$ together with A and the carbon atom between them denotes a $C_{5-7}$-cycloalkylidene group to which a phenyl ring may be fused via two adjacent carbon atoms, whilst said phenyl ring may additionally be substituted by one or two $C_{1-3}$-alkyl or $C_{1-3}$-alkoxy groups, whilst the substituents may be identical or different, and B denotes a 5- or 6-membered heteroaryl group substituted by a carboxy group or capable of being converted into a carboxy group in vivo, a phenyl or naphthyl group, each of which may be substituted by a carboxy group, by a group which may be converted into a carboxy group in vivo or by a group which is negatively charged under physiological conditions, whilst the abovementioned phenyl groups may additionally be substituted by a fluorine, chlorine, bromine or iodine atom, by a $C_{1-3}$-alkyl, trifluoromethyl, phenyl, hydroxy, $C_{1-3}$-alkoxy, $C_{1-3}$-alkylsulphonyloxy, phenylsulphonyloxy, carboxy, $C_{1-3}$-alkoxycarbonyl, formyl, $C_{1-3}$-alkylcarbonyl, $C_{1-3}$-alkylsulphonyl, phenylsulphonyl, nitro, pyrrolidino, piperidino, morpholino, N-($C_{1-3}$-alkyl)-piperazino, aminosulphonyl, $C_{1-3}$-alkylaminosulphonyl or di-($C_{1-3}$-alkyl)-aminosulphonyl group, by a $C_{1-3}$-alkyl group which is substituted by a hydroxy, $C_{1-3}$-alkoxy, amino, $C_{1-4}$-alkylamino, di-($C_{1-4}$-alkyl)-amino, $C_{3-7}$-cycloalkylamino, pyrrolidino, piperidino, morpholino, piperazino or N-($C_{1-3}$-alkyl)-piperazino group, by an n-$C_{2-3}$-alkoxy, $C_{2-3}$-alkenyl or $C_{2-3}$-alkynyl group substituted in the 2 or 3 position by a di-($C_{1-3}$-alkyl)-amino group, by an amino group, by an N-($C_{1-3}$-alkyl)-amino or N,N-di-($C_{1-3}$-alkyl)-amino group wherein the alkyl moiety may in each case be substituted in the 2 or 3 position in relation to the nitrogen atom by a $C_{1-3}$-alkoxy group, by a N-phenylamino, N-(phenyl-$C_{1-3}$-alkyl)-amino or N-(pyridyl-$C_{1-3}$-alkyl)-amino group wherein in each case a hydrogen atom of the abovementioned amino groups may be substituted by a $C_{1-3}$-alkylsulphonyl, phenyl-$C_{1-3}$-alkylsulphonyl or phenylsulphonyl group or by a $C_{1-7}$-alkyl group, which may be replaced in the 2 to 5 position by a $C_{1-3}$-alkoxy, cyano, amino, $C_{1-3}$-alkylamino, di-($C_{1-3}$-alkyl)-amino or tetrazolyl group, by an aminocarbonyl or $C_{1-3}$-alkylaminocarbonyl group which may in each case be substituted at the amino-nitrogen atom by a $C_{1-4}$-alkyl group which may be substituted by a vinyl, ethynyl, phenyl, pyridyl, imidazolyl, carboxy or trifluoromethyl group or, with the exception of the 2 position based on the aminocarbonyl nitrogen atom, by a hydroxy, $C_{1-3}$-alkoxy, $C_{1-3}$-alkylthio, amino, $C_{1-3}$-alkylamino, di-($C_{1-3}$-alkyl)-amino, $C_{1-4}$-alkanoylamino or $C_{1-5}$-alkoxycarbonylamino group, by a $C_{3-7}$-cycloalkyl, $C_{5-9}$-Azabicycloalkyl, phenyl, pyridyl, $C_{1-3}$-alkoxy or di-($C_{1-3}$-alkyl)-amino group, by a $C_{1-3}$-alkyl group which is substituted by a piperidin-3-yl or piperidin-4-yl group optionally substituted in the 1 position by a $C_{1-3}$-alkyl or $C_{1-5}$-alkoxycarbonyl group, or by an amino, $C_{1-3}$-alkylamino or phenyl-$C_{1-3}$-alkylamino group optionally substituted at the amino-nitrogen atom by a $C_{1-4}$-alkanoyl, $C_{1-5}$-alkoxycarbonyl, benzoyl, pyrrolidino, piperidino, morpholino or N-($C_{1-3}$-alkyl)-piperazino group, by a carbonyl group substituted by a pyrrolidino, pyrrolino, piperidino, morpholino or N-($C_{1-3}$-alkyl)-piperazino group, by a sulphonyl group substituted by an amino, $C_{1-3}$-alkylamino, di-($C_{1-3}$-alkyl)-amino, pyrrolidino, piperidino, morpholino or N-($C_{1-3}$-alkyl)-piperazino group, by an amino or N-($C_{1-3}$-alkyl)-amino group which is substituted in each case at the amino-nitrogen atom by an aminocarbonyl, $C_{1-3}$-alkylaminocarbonyl, phenyl-$C_{1-3}$-alkylaminocarbonyl, phenylaminocarbonyl, phenoxyphenylaminocarbonyl, pyridylaminocarbonyl, pyrrolidinocarbonyl, piperidinocarbonyl, morpholinocarbonyl or N-($C_{1-3}$-alkyl)-piperazinocarbonyl group, whilst any hydrogen atom present in the abovementioned aminocarbonyl groups may additionally be substituted by a $C_{1-3}$-alkyl group, by a 5- or 6-membered heteroaryl group, by a dihydro-oxazolyl, dihydro-imidazolyl, 2-oxopyrrolidino, 2-oxo-piperidino or 2-oxohexamethyleneimino group to which a phenyl ring may be fused via two adjacent carbon atoms, by an ethynyl group substituted by a phenyl, hydroxymethyl or dimethylamino group, whilst additionally the abovementioned mono- or disubstituted phenyl groups may be substituted by another fluorine, chlorine or bromine atom or by one or two other $C_{1-3}$-alkyl or $C_{1-3}$-alkoxy groups and two $C_{1-3}$-alkoxy groups in the o position may be replaced by a methylenedioxy group, in particular $R_1$ denotes a hydrogen atom, a $C_{1-3}$-alkyl or trifluoromethyl group, $R_2$ denotes a hydrogen, fluorine, chlorine or bromine atom, a $C_{1-3}$-alkyl, $C_{3-7}$-cycloalkyl or $C_{1-3}$-alkoxy group or, if $R_4$ and $R_5$ each denote a hydrogen atom, $R_1$ and $R_2$ together denote an n-$C_{1-3}$-alkylene group optionally substituted by a $C_{1-3}$-alkyl group, $R_3$ denotes a hydrogen atom or a $C_{1-5}$-alkyl group, $R_4$ and $R_5$ each denote a hydrogen atom or together denote another carbon-carbon bond, A denotes a phenyl, naphthyl or tetrahydronaphthyl group substituted by a fluorine, chlorine, bromine or iodine atom, by a $C_{1-6}$-alkyl, $C_{3-7}$-cycloalkyl, phenyl, $C_{1-3}$-alkoxy, trifluoromethyl or nitro group, whilst the abovementioned monosubstituted phenyl and naphthyl groups may additionally be substituted by a fluorine, chlorine or bromine atom, or by a $C_{1-3}$-alkyl or $C_{1-3}$-alkoxy group, a naphthyl group, a chromane or chromene group wherein a methylene group may be replaced by a carbonyl group, a 5- or 6-membered heteroaryl group optionally substituted in the carbon skeleton by a fluorine, chlorine or bromine atom or by a $C_{1-3}$-alkyl or $C_{1-3}$-alkoxy group, whilst the 6-membered heteroaryl groups contain one, two or three nitrogen atoms and the 5-membered heteroaryl groups contain an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and additionally a phenyl ring may be fused to the abovementioned monocyclic heteroaryl groups via two adjacent carbon atoms whilst said phenyl ring may also be substituted in the carbon skeleton by a fluorine, chlorine or bromine atom or by a $C_{1-3}$-alkyl or $C_{1-3}$-alkoxy group, a phenylvinyl group or R₁ together with A and the carbon atom between them denote a $C_{5-7}$-cycloalkylidene group to which a phenyl ring may be fused via two adjacent carbon atoms, whilst said phenyl ring may additionally be substituted by one or two $C_{1-3}$-alkyl or $C_{1-3}$-alkoxy groups, whilst the substituents may be identical or different, and B denotes a phenyl, naphthyl or heteroaryl group, each of which may be substituted by a carboxy group, by a group which may be converted into a carboxy group in vivo or by a group which is negatively charged under physiological conditions, whilst the abovementioned phenyl groups may additionally be substituted by a fluorine, chlorine, bromine or iodine atom, by a $C_{1-3}$-alkyl, hydroxy, $C_{1-3}$-alkoxy, $C_{1-3}$-alkylsulphonyloxy, phenylsulphonyloxy, carboxy, $C_{1-3}$-alkoxycarbonyl, formyl, $C_{1-3}$-alkylcarbonyl, $C_{1-3}$-alkylsulphonyl, phenylsulphonyl, nitro, pyrrolidino, piperidino, morpholino, N-($C_{1-3}$-alkyl)-piperazino, aminosulphonyl, $C_{1-3}$-alkylaminosulphonyl or di-($C_{1-3}$-alkyl)-aminosulphonyl group, by an n-$C_{2-3}$-alkoxy group substituted in the 2 or 3 position by a di-($C_{1-3}$-alkyl)-amino group, by an amino, N-($C_{1-3}$-alkyl)-amino, N-(phenyl-$C_{1-3}$-alkyl)-amino or N-(pyridyl-$C_{1-3}$-alkyl)-amino group wherein in each case a hydrogen atom of the amino group may be substituted by a $C_{1-3}$-alkylsulphonyl or phenylsulphonyl group or by a $C_{1-7}$-alkyl group, which may be substituted in the 2 to 5 position by a $C_{1-3}$-alkoxy, cyano, amino, $C_{1-3}$-alkylamino, di-($C_{1-3}$-alkyl)-amino or tetrazolyl group, by a carbonyl or sulphonyl group substituted by an amino, $C_{1-3}$-alkylamino, di-($C_{1-3}$-alkyl)-amino, pyrrolidino, piperidino, morpholino or N-($C_{1-3}$-alkyl)-piperazino group, by an imidazolyl or pyrazolyl group optionally substituted by a $C_{1-4}$-alkyl group, which may additionally be substituted by a $C_{1-3}$-alkyl, phenyl, trifluoromethyl or furyl group, and may additionally be substituted by another fluorine, chlorine or bromine atom, by another $C_{1-3}$-alkyl or $C_{1-3}$-alkoxy group, and the abovementioned 6-membered heteroaryl groups contain one, two or three nitrogen atoms and the abovementioned 5-membered heteroaryl groups contain an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and additionally a phenyl ring may be fused to the abovementioned monocyclic heteroaryl groups via two adjacent carbon atoms, whilst said phenyl ring may be substituted in the carbon skeleton by a fluorine, chlorine or bromine atom or by a $C_{1-3}$-alkyl or $C_{1-3}$-alkoxy group, whilst the abovementioned 5-membered monocyclic heteroaryl groups in the carbon skeleton may additionally be substituted by a $C_{1-4}$-alkyl, trifluoromethyl, phenyl or furanyl group and by another $C_{1-3}$-alkyl group, whilst amino and imino groups mentioned in the definition of the abovementioned groups may additionally be substituted by a group which can be cleaved in vivo.

By a group which can be converted in vivo into a carboxy group is meant, for example, a hydroxymethyl group, a carboxy group esterified with an alcohol, wherein the alcoholic moiety preferably denotes a $C_{1-6}$-alkanol, a phenyl-$C_{1-3}$-alkanol, a $C_{3-9}$-cycloalkanol, whilst a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-Cycloalkyl-$C_{1-3}$-alkanol, a bicycloalkanol having a total of 8 to 10 carbon atoms which may additionally be substituted by one or two $C_{1-3}$-alkyl groups in the bicycloalkyl moiety, a 1,3-dihydro-3-oxo-1-isobenzfuranol or an alcohol of formula

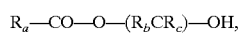

wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom or a $C_{1-3}$-alkyl group, by a group which is negatively charged under physiological conditions is meant a carboxy, hydroxysulphonyl, phosphono, tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert. butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_a$—CO—O—($R_bCR_c$)—O—CO group wherein $R_a$ to $R_c$ are as hereinbefore defined.

Moreover, the saturated alkyl and alkoxy moieties containing more than 2 carbon atoms mentioned in the definitions given above also include the branched isomers thereof, such as the isopropyl, tert.butyl, isobutyl group, etc.

The present invention thus relates to the use of the above carboxylic acid amides of general formula I in the inhibition of telomerase and the preparation of a corresponding pharmaceutical composition.

The invention also relates to the new carboxylic acid amides of the above general formula I and the salts thereof, particularly the physiologically acceptable salts thereof, which have an inhibitory effect on telomerase, processes for preparing them, pharmaceutical compositions containing these compounds and their use.

In the new carboxylic acid amides of the above general formula I $R_1$ denotes a hydrogen atom, a $C_{1-3}$-alkyl or trifluoromethyl group, $R_2$ denotes a hydrogen, fluorine, chlorine or bromine atom, a $C_{1-3}$-alkyl, $C_{3-7}$-cycloalkyl or $C_{1-3}$-alkoxy group or, if $R_4$ and $R_5$ each denote a hydrogen atom, $R_1$ and $R_2$ together denote n n-$C_{1-3}$-alkylene group optionally substituted by a $C_{1-3}$-alkyl group, $R_3$ denotes a hydrogen atom or a $C_{1-5}$-alkyl group, $R_4$ and $R_5$ each denote a hydrogen atom or together denote another carbon-carbon bond, A denotes a phenyl, naphthyl or tetrahydronaphthyl group substituted by a fluorine, chlorine, bromine or iodine atom, by a $C_{1-6}$-alkyl, $C_{3-7}$-cycloalkyl, phenyl, $C_{1-3}$-alkoxy, cyano, trifluoromethyl or nitro group, whilst the abovementioned monosubstituted phenyl and naphthyl groups may additionally be substituted by a fluorine, chlorine or bromine atom, by a $C_{1-3}$-alkyl or $C_{1-3}$-alkoxy group and the abovementioned disubstituted phenyl groups may additionally be substituted by a $C_{1-3}$-alkyl or $C_{1-3}$-alkoxy group, with the proviso that A does not denote a phenyl group which is substituted
- by a halogen atom, by a methyl, pentyl, $C_{1-3}$-alkoxy or phenyl group or by two $C_{1-3}$-alkoxy groups, if
  $R_3$ denotes a hydrogen atom,
  $R_4$ and $R_5$ each denote a hydrogen atom or
  $R_4$ and $R_5$ together denote another carbon-carbon bond and
  B denotes a carboxyphenyl or methoxycarbonylphenyl group,
- and A does not denote a phenyl group substituted by a methyl or phenyl group if
  $R_1$ and $R_2$ each denote a hydrogen atom,
  $R_3$ denotes a hydrogen atom,
  $R_4$ and $R_5$ together denote another carbon-carbon bond and
  B denotes a carboxyphenyl or methoxycarbonylphenyl group, a naphthyl group, a chromane or chromene group wherein a methylene group may be replaced by a carbonyl group, a 5- or 6-membered heteroaryl group optionally substituted in the carbon skeleton by a fluorine, chlorine or bromine atom or by a $C_{1-3}$-alkyl or $C_{1-3}$-alkoxy group, whilst the 6-membered heteroaryl groups contain one, two or three nitrogen atoms and the 5-membered heteroaryl groups contain an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and additionally a phenyl ring may be fused to the abovementioned monocyclic heteroaryl groups via two adjacent carbon atoms, whilst said phenyl ring may also be substituted in the carbon skeleton by a fluorine, chlorine or bromine atom, by a $C_{1-3}$-alkyl or $C_{1-3}$-alkoxy group, a phenylvinyl group or $R_1$ together with A and the carbon atom between them denote a $C_{5-7}$-cycloalkylidene group to which a phenyl ring may be fused via two adjacent carbon atoms, whilst said phenyl ring may additionally be substituted by one or two $C_{1-3}$-alkyl or $C_{1-3}$-alkoxy groups, whilst the substituents may be identical or different, and B denotes a 5- or 6-membered heteroaryl group substituted by a carboxy group or by a group which may be converted into a carboxy group in vivo, a phenyl or naphthyl group, each of which may be substituted by a carboxy group, by a group which may be converted into a carboxy group in vivo or by a group which is negatively charged under physiological conditions, whilst the abovementioned phenyl groups may additionally be substituted by a fluorine, chlorine, bromine or iodine atom, by a $C_{1-3}$-alkyl, trifluoromethyl, phenyl, hydroxy, $C_{1-3}$-alkoxy, $C_{1-3}$-alkylsulphonyloxy, phenylsulphonyloxy, carboxy, $C_{1-3}$-alkoxycarbonyl, formyl, $C_{1-3}$-alkylcarbonyl, $C_{1-3}$-alkylsulphonyl, phenylsulphonyl, nitro, pyrrolidino, piperidino, morpholino, N-($C_{1-3}$-alkyl)-piperazino, aminosulphonyl, $C_{1-3}$-alkylaminosulphonyl or di-($C_{1-3}$-alkyl)-aminosulphonyl group, by a $C_{1-3}$-alkyl group which is substituted by a hydroxy, $C_{1-3}$-alkoxy, amino, $C_{1-4}$-alkylamino, di-($C_{1-4}$-alkyl)-amino, $C_{3-7}$-cycloalkylamino, pyrrolidino, piperidino, morpholino, piperazino or N-($C_{1-3}$-alkyl)-piperazino group, by an n-$C_{2-3}$-alkoxy, $C_{2-3}$-alkenyl or $C_{2-3}$-alkynyl group substituted in the 2 or 3 position by a di-($C_{1-3}$-alkyl)-amino group, by an amino group, by an N-($C_{1-3}$-alkyl)-amino or N,N-di-($C_{1-3}$-alkyl)-amino group wherein the alkyl moiety may in each case be substituted in the 2 or 3 position in relation to the nitrogen atom by a $C_{1-3}$-alkoxy group, by an N-phenylamino, N-(phenyl-$C_{1-3}$-alkyl)-amino or N-(pyridyl-$C_{1-3}$-alkyl)-amino group wherein in each case a hydrogen atom of the abovementioned amino groups may be substituted by a $C_{1-3}$-alkylsulphonyl, phenyl-$C_{1-3}$-alkylsulphonyl or phenylsulphonyl group or by a $C_{1-7}$-alkyl group which may be replaced in the 2 to 5 position by a $C_{1-3}$-alkoxy, cyano, amino, $C_{1-3}$-alkylamino, di-($C_{1-3}$-alkyl)-amino or tetrazolyl group, by an aminocarbonyl or $C_{1-3}$-alkylaminocarbonyl group which may in each case be substituted at the amino-nitrogen atom by a $C_{1-4}$-alkyl group which may be substituted by a vinyl, ethynyl, phenyl, pyridyl, imidazolyl, carboxy or trifluoromethyl group or, with the exception of the 2 position relative to the aminocarbonyl nitrogen atom, by a hydroxy, $C_{1-3}$-alkoxy, $C_{1-3}$-alkylthio, amino, $C_{1-3}$-alkylamino, di-($C_{1-3}$-alkyl)-amino, $C_{1-4}$-alkanoylamino or $C_{1-5}$-alkoxycarbonylamino group, by a $C_{3-7}$-cycloalkyl, $C_{5-9}$-azabicycloalkyl, phenyl, pyridyl, $C_{1-3}$-alkoxy or di-($C_{1-3}$-alkyl)-amino group, by a $C_{1-3}$-alkyl group which is substituted by a piperidin-3-yl or piperidin-4-yl group optionally substituted in the 1 position by a $C_{1-3}$-alkyl or $C_{1-5}$-alkoxycarbonyl group, or by an amino, $C_{1-3}$-alkylamino or phenyl-$C_{1-3}$-alkylamino group optionally substituted at the amino-nitrogen atom by a $C_{1-4}$-alkanoyl, $C_{1-5}$-alkoxycarbonyl, benzoyl, pyrrolidino, piperidino, morpholino or N-($C_{1-3}$-alkyl)-piperazino group, by a carbonyl group substituted by a pyrrolidino, pyrrolino, piperidino, morpholino or N-($C_{1-3}$-alkyl)-piperazino group, by a sulphonyl group substituted by an amino, $C_{1-3}$-alkylamino, di-($C_{1-3}$-alkyl)-amino, pyrrolidino, piperidino, morpholino or N-($C_{1-3}$-alkyl)-piperazino group, by an amino or N-($C_{1-3}$-alkyl)-amino group which may in each case be substituted at the amino-nitrogen atom by an aminocarbonyl, $C_{1-3}$-alkylaminocarbonyl, phenyl-$C_{1-3}$-alkylaminocarbonyl, phenylaminocarbonyl, phenoxyphenylaminocarbonyl, pyridylaminocarbonyl, pyrrolidinocarbonyl, piperidinocarbonyl, morpholinocarbonyl or N-($C_{1-3}$-alkyl)-piperazinocarbonyl group, wherein additionally any hydrogen atom of one of the abovementioned aminocarbonyl groups present may be substituted by a $C_{1-3}$-alkyl group, by a 5- or 6-membered heteroaryl group, by a dihydro-oxazolyl, dihydro-imidazolyl, 2-oxo-pyrrolidino, 2-oxo-piperidino or 2-oxo-hexamethyleneimino group to which a phenyl ring may be fused via two adjacent carbon atoms, by an ethynyl group substituted by a phenyl, hydroxymethyl or dimethylamino group, whilst additionally the abovementioned mono- or disubstituted phenyl groups may be substituted by another fluorine, chlorine or bromine atom or by one or two other $C_{1-3}$-alkyl or $C_{1-3}$-alkoxy groups and two $C_{1-3}$-alkoxy groups in the o position may be replaced by a methylenedioxy group, in particular $R_1$ denotes a hydrogen atom, a $C_{1-3}$-alkyl or trifluoromethyl group, $R_2$ denotes a hydrogen, fluorine, chlorine or bromine atom, a $C_{1-3}$-alkyl, $C_{3-7}$-cycloalkyl or $C_{1-3}$-alkoxy group or, if $R_4$ and $R_5$ each denote a hydrogen atom, $R_1$ and $R_2$ together denote an n-$C_{1-3}$-alkylene group optionally substituted by a $C_{1-3}$-alkyl group, $R_3$ denotes a hydrogen atom or a $C_{1-5}$-alkyl group, $R_4$ and $R_5$ each denote a hydrogen atom or together denote another carbon-carbon bond, A denotes a phenyl, naphthyl or tetrahydronaphthyl group substituted by a fluorine, chlorine, bromine or iodine atom or by a $C_{1-6}$-alkyl, $C_{3-7}$-cycloalkyl, phenyl, $C_{1-3}$-alkoxy, trifluoromethyl or nitro group, whilst the abovementioned monosubstituted phenyl and naphthyl groups may additionally be substituted by a fluorine, chlorine or bromine atom or by a $C_{1-3}$-alkyl or $C_{1-3}$-alkoxy group, with the proviso that A does not denote a phenyl group which is substituted by a halogen atom, by a methyl, pentyl, $C_{1-3}$-alkoxy or phenyl group or by two $C_{1-3}$-alkoxy groups if
  $R_3$ denotes a hydrogen atom,
  $R_4$ and $R_5$ each denote a hydrogen atom or
  $R_4$ and $R_5$ together denote another carbon-carbon bond and
  B denotes a carboxyphenyl or methoxycarbonylphenyl group, and A does not denote a phenyl group which is substituted by a methyl or phenyl group if
  $R_1$ and $R_2$ each denote a hydrogen atom,
  $R_3$ denotes a hydrogen atom,
  $R_4$ and $R_5$ together denote another carbon-carbon bond and
  B denotes a carboxyphenyl or methoxycarbonylphenyl group, a naphthyl group, a chromane or chromene group wherein a methylene group may be replaced by a carbonyl group, a 5- or 6-membered heteroaryl group optionally substituted in the carbon skeleton by a fluorine, chlorine or bromine atom or by a $C_{1-3}$-alkyl or $C_{1-3}$-alkoxy group, whilst the 6-membered heteroaryl groups contain one, two or three nitrogen atoms and the 5-membered heteroaryl groups contain an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and additionally a phenyl ring may be fused to the abovementioned monocyclic heteroaryl groups via two adjacent carbon atoms, whilst said phenyl ring may also be substituted in the carbon skeleton by a fluorine, chlorine or bromine atom, by a $C_{1-3}$-alkyl or $C_{1-3}$-alkoxy group, a phenylvinyl group or $R_1$ together with A and the carbon atom between them denote a $C_{5-7}$-cycloalkylidene group to which a phenyl ring may be fused via two adjacent carbon atoms, whilst said phenyl ring may additionally be substituted by one or two $C_{1-3}$-alkyl or $C_{1-3}$-alkoxy group, whilst the substituents may be identical or different, and B denotes a phenyl, naphthyl or heteroaryl group, each of which may be substituted by a carboxy group, by a group which may be converted into a carboxy group in vivo or by a group which is negatively charged under physiological conditions, whilst the abovementioned phenyl groups may additionally be substituted by a fluorine, chlorine, bromine or iodine atom, by a $C_{1-3}$-alkyl, hydroxy, $C_{1-3}$-alkoxy, $C_{1-3}$-alkylsulphonyloxy, phenylsulphonyloxy, carboxy, $C_{1-3}$-alkoxycarbonyl, formyl, $C_{1-3}$-alkylcarbonyl, $C_{1-3}$-alkylsulphonyl, phenylsulphonyl, nitro, pyrrolidino, piperidino, morpholino, N-($C_{1-3}$-alkyl)-piperazino, aminosulphonyl, $C_{1-3}$-alkylaminosulphonyl or di-($C_{1-3}$-alkyl)-aminosulphonyl group, by an n-$C_{2-3}$-alkoxy, $C_{2-3}$-alkenyl or $C_{2-3}$-alkynyl group substituted in the 2 or 3 position by a di-($C_{1-3}$-alkyl)-amino group, by an amino, N-($C_{1-3}$-alkyl)-amino, N-(phenyl-$C_{1-3}$-alkyl)-amino or N-(pyridyl-$C_{1-3}$-alkyl)-amino group wherein in each case a hydrogen atom of the amino group may be substituted by a $C_{1-3}$-alkylsulphonyl or phenylsulphonyl group or by a $C_{1-7}$-alkyl group, which may be substituted in the 2 to 5 position by a $C_{1-3}$-alkoxy, cyano, amino, $C_{1-3}$-alkylamino, di-($C_{1-3}$-alkyl)-amino or tetrazolyl group, by a carbonyl or sulphonyl group substituted by an amino, $C_{1-3}$-alkylamino, di-($C_{1-3}$-alkyl)-amino, pyrrolidino, piperidino, morpholino or N-($C_{1-3}$-alkyl)-piperazino group, by an imidazolyl or pyrazolyl group optionally substituted by a $C_{1-4}$-alkyl group, which may additionally be substituted by a $C_{1-3}$-alkyl, phenyl, trifluoromethyl or furyl group, and may additionally be substituted by another fluorine, chlorine or bromine atom or by another $C_{1-3}$-alkyl or $C_{1-3}$-alkoxy group, and the abovementioned 6-membered heteroaryl groups contain one, two or three nitrogen atoms and the abovementioned 5-membered heteroaryl groups contain an imino group optionally substituted by a $C_{1-3}$-alkyl group, an oxygen or sulphur atom or an imino group optionally substituted by a $C_{1-3}$-alkyl group substituted and an oxygen or sulphur atom or one or two nitrogen atoms and additionally a phenyl ring may be fused to the abovementioned monocyclic heteroaryl groups via two adjacent carbon atoms, this phenyl ring optionally being substituted in the carbon skeleton by a fluorine, chlorine or bromine atom or by a $C_{1-3}$-alkyl or $C_{1-3}$-alkoxy group, whilst the abovementioned 5-membered monocyclic heteroaryl groups in the carbon skeleton may additionally be substituted by a $C_{1-4}$-alkyl, trifluoromethyl, phenyl or furanyl group and by another $C_{1-3}$-alkyl group, and the amino and imino groups mentioned in the definition of the abovementioned groups may additionally be substituted by a group which may be cleaved in vivo, the isomers thereof and the salts thereof.

Preferred compounds of the above general formula I are those wherein

B and $R_2$ to $R_5$ are as hereinbefore defined, $R_1$ denotes a hydrogen atom or a $C_{1-3}$-alkyl group and A denotes a phenyl, naphthyl or tetrahydronaphthyl group substituted by a fluorine, chlorine, bromine or iodine atom or by a $C_{1-6}$-alkyl, $C_{3-7}$-cycloalkyl, phenyl, $C_{1-3}$-alkoxy, trifluoromethyl or nitro group, whilst the abovementioned monosubstituted phenyl and naphthyl groups may additionally be substituted by a fluorine, chlorine or bromine atom or by a $C_{1-3}$-alkyl or $C_{1-3}$-alkoxy group, with the proviso that A does not denote a phenyl group which may be mono- or disubstituted by halogen atoms, $C_{1-4}$-alkyl or $C_{1-3}$-alkoxy groups, wherein the substituents may be identical or different, and does not represent a 4-biphenyl or pentylphenyl group if $R_1$ and $R_2$ each denote a hydrogen atom or a $C_{1-4}$-alkyl group, $R_3$ denotes a hydrogen atom, $R_4$ and $R_5$ each denote a hydrogen atom or $R_4$ and $R_5$ together denote another carbon-carbon bond and B denotes a carboxyphenyl or methoxycarbonylphenyl group, a naphthyl group, a chromane or chromene group wherein a methylene group may be replaced by a carbonyl group, a 5- or 6-membered heteroaryl group optionally substituted in the carbon skeleton by a fluorine, chlorine or bromine atom or by a $C_{1-3}$-alkyl or $C_{1-3}$-alkoxy group, whilst the 6-membered heteroaryl groups contain one, two or three nitrogen atoms and the 5-membered heteroaryl groups contain an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and additionally a phenyl ring may be fused to the abovementioned monocyclic heteroaryl groups via two adjacent carbon atoms, whilst said phenyl ring may also be substituted in the carbon skeleton by a fluorine, chlorine or bromine atom or by a $C_{1-3}$-alkyl or $C_{1-3}$-alkoxy group, the isomers thereof and the salts thereof.

Particularly preferred new compounds of the above general formula I are those wherein $R_1$ denotes a hydrogen atom or a $C_{1-3}$-alkyl group, $R_2$ denotes a hydrogen atom or a methyl group or, if $R_4$ and $R_5$ each denote a hydrogen atom, $R_1$ and $R_2$ together denote a methylene bridge, $R_3$ denotes a hydrogen atom or a $C_{1-5}$-alkyl group, $R_4$ and $R_5$ together denote another carbon-carbon bond, A denotes a phenyl group substituted by a fluorine, chlorine, bromine or iodine atom or by a $C_{1-5}$-alkyl, cyclohexyl, phenyl, methoxy, cyano or trifluoromethyl group, a phenyl group substituted by fluorine, chlorine or bromine atoms, by methyl or methoxy groups, whilst the substituents may be identical or different, or a $C_{1-3}$-alkylphenyl group, which is disubstituted by fluorine, chlorine or bromine atoms, whilst the substituents may be identical or different, with the proviso that A does not denote a phenyl group which is substituted by a halogen atom, by a methyl, pentyl, $C_{1-3}$-alkoxy or phenyl group or by two $C_{1-3}$-alkoxy groups, if $R_3$ denotes a hydrogen atom, $R_4$ and $R_5$ each denote a hydrogen atom or $R_4$ and $R_5$ together denote another carbon-carbon bond and B denotes a carboxyphenyl or methoxycarbonylphenyl group, and A does not denote a phenyl group which is substituted by a methyl or phenyl group if $R_1$ and $R_2$ each denote a hydrogen atom, $R_3$ denotes a hydrogen atom, $R_4$ and $R_5$ together denote another carbon-carbon bond and B denotes a carboxyphenyl or methoxycarbonylphenyl group, a naphthyl group optionally substituted by a fluorine, chlorine or bromine atom or by a methyl or methoxy group, a tetrahydronaphthyl group, a chromene group wherein a methylene group is replaced by a carbonyl group, a pyridyl, benzofuryl, benzothienyl, quinolyl or isoquinolyl group optionally substituted by a methyl group and B denotes a cyclohexyl, trimethoxyphenyl, methylenedioxyphenyl, naphthyl, pyridyl, thienyl, pyrazolyl, quinolyl or isoquinolyl group substituted by a carboxy group, a phenyl group substituted by a carboxy, methoxycarbonyl, ethoxycarbonyl, hydroxymethyl, sulpho, tetrazolyl, methylsulphonylaminocarbonyl or phenylsulphonylaminocarbonyl group, which may additionally be substituted by a fluorine, chlorine, bromine or iodine atom, by a methyl, trifluoromethyl, phenyl, hydroxymethyl, hydroxy, methoxy, methylsulphonyloxy, 2-dimethylamino-ethoxy, carboxy, nitro, methylsulphonylamino, phenylsulphonylamino, aminosulphonyl, pyrrolidino, piperidino or morpholino group, by a methyl group which is substituted by an amino, $C_{1-3}$-alkylamino, cyclopentylamino, pyrrolidino or piperidino group, by an amino, N-methyl-amino or N-(2-methoxy-ethyl)-amino group which may in each case be substituted at the amino-nitrogen atom by a $C_{1-7}$-alkyl or phenyl group, by an ethyl group which is substituted in the 1 or 2 position by a phenyl or pyridyl group, by a $C_{2-4}$-alkyl group which is terminally substituted by a methoxy, cyano, dimethylamino or tetrazolyl group, by an acetyl, benzoyl, $C_{1-5}$-alkoxycarbonyl, aminocarbonyl or methylaminocarbonyl group, whilst the aminocarbonyl moiety of the abovementioned groups may in each case additionally be substituted by an optionally phenyl-substituted $C_{1-3}$-alkyl group, by a phenyl, phenoxyphenyl or pyridyl group, by a methylsulphonyl, phenylsulphonyl or benzylsulphonyl group, by an aminocarbonyl or methylaminocarbonyl group which may in each case be substituted at the amino-nitrogen atom by a $C_{1-4}$-alkyl, $C_{3-6}$-cycloalkyl, phenyl, benzyl, pyridyl, pyridylmethyl or methoxy group, by a methyl group which is substituted by a vinyl, ethynyl, trifluoromethyl, $C_{7-9}$-azabicycloalkyl, carboxy or imidazolyl group or by a piperidin-4-yl group optionally substituted in the 1 position by a methyl or $C_{1-5}$-alkoxycarbonyl group, by a straight-chain or branched $C_{2-3}$-alkyl group substituted in the 2 or 3 position by a hydroxy, methoxy, methylthio, amino, acetylamino, $C_{1-5}$-alkoxycarbonylamino, carboxy-, $C_{1-5}$-alkoxycarbonyl or dimethylamino group, by a pyrrolidino, piperidino, morpholino, 4-methyl-piperazino, amino or methylamino group, whilst the abovementioned amino and methylamino groups may each additionally be substituted at the amino-nitrogen atom by a methyl, acetyl, benzoyl or $C_{1-5}$-alkoxycarbonyl group, by a dihydro-oxazolyl, dihydro-imidazolyl, 2-oxo-pyrrolidino, 2-oxo-piperidino or 2-oxo-hexamethyleneimino group to which a phenyl ring may be fused via two adjacent carbon atoms, by an imidazolyl or 4-methyl-imidazolyl group optionally substituted by a methyl, ethyl or phenyl group, to which a phenyl ring may additionally be fused via two adjacent carbon atoms, a pyrazolyl group optionally substituted by a $C_{1-4}$-alkyl or furanyl group, which may additionally be substituted by a methyl or trifluoromethyl group, by an ethynyl group substituted by a phenyl, hydroxymethyl or dimethylamino group, whilst additionally the abovementioned mono- or disubstituted phenyl groups may be substituted by another fluorine, chlorine or bromine atom or by one or two other methyl or methoxy groups, particularly those compounds wherein $R_1$ denotes a hydrogen atom or a $C_{1-3}$-alkyl group, $R_2$ denotes a hydrogen atom or $R_1$ and $R_2$ together denote a methylene group, if $R_4$ and $R_5$ each simultaneously denote a hydrogen atom, $R_3$ denotes a hydrogen atom, $R_4$ and $R_5$ together denote another carbon-carbon bond, A denotes a phenyl or naphthyl group mono- or disubstituted by a fluorine, chlorine, bromine or iodine atom or by a $C_{1-6}$-alkyl, $C_{3-7}$-cycloalkyl or trifluoromethyl group, whilst the substituents may be identical or different, with the proviso that A does not denote a phenyl group which may be mono- or di-substituted by halogen atoms or $C_{1-4}$-alkyl groups, wherein the substituents may be identical or different, and does not denote a 4-biphenyl or pentylphenyl group if $R_1$ denotes a hydrogen atom or a $C_{1-3}$-alkyl group, $R_2$ denotes a hydrogen atom, $R_3$ denotes a hydrogen atom, $R_4$ and $R_5$ each denote a hydrogen atom or $R_4$ and $R_5$ together denote another carbon-carbon bond and B denotes a carboxyphenyl or methoxycarbonylphenyl group, a naphthyl group, a chromene group wherein a methylene group is replaced by a carbonyl group, a benzothienyl group and B denotes a phenyl, naphthyl, thienyl or pyridinyl group, each of which is substituted by a carboxy group, whilst the abovementioned phenyl groups may additionally be substituted by a fluorine, chlorine or bromine atom, by a $C_{1-3}$-alkyl, hydroxy, $C_{1-3}$-alkoxy, $C_{1-3}$-alkylsulphonyloxy, pyrrolidino, piperidino, morpholino or N-($C_{1-3}$-alkyl)-piperazino group, by an n-$C_{2-3}$-alkoxy group substituted in the 2 or 3 position by a di-($C_{1-3}$-alkyl)-amino group, by an N-methyl-N-(n-$C_{2-3}$-alkyl)-amino group substituted in the 2 or 3 position by a di-($C_{1-3}$-alkyl)-amino group, by a di-($C_{1-3}$-alkyl)-amino group, by an imidazolyl or pyrazolyl group optionally substituted by a $C_{1-4}$-alkyl group, by a $C_{1-4}$-alkylaminocarbonyl, N-(pyridinylmethyl)-aminocarbonyl, pyrrolidinoaminocarbonyl or piperidinoaminocarbonyl group and may additionally be substituted by another fluorine atom, by another $C_{1-3}$-alkyl or $C_{1-3}$-alkoxy group, the isomers thereof and the salts thereof.

Most particularly preferred compounds of general formula I are those wherein $R_1$ denotes a methyl group, $R_2$ denotes a hydrogen atom, $R_3$ denotes a hydrogen atom, $R_4$ and $R_5$ together denote another carbon-carbon bond, A denotes a phenyl group substituted by two chlorine or bromine atoms or by a chlorine atom and a bromine atom, a naphthyl, 2-oxo-chromene or benzothienyl group, with the proviso that A does not denote a phenyl group disubstituted by halogen atoms if $R_1$ denotes a methyl group, $R_2$ denotes a hydrogen atom, $R_3$ denotes a hydrogen atom, $R_4$ and $R_5$ each denote a hydrogen atom or $R_4$ and $R_5$ together denote another carbon-carbon bond and B denotes a carboxyphenyl or methoxycarbonylphenyl group, and B denotes a 2-carboxy-phenyl, 2-carboxy-thienyl or 2-carboxy-pyridinyl group, whilst the abovementioned 2-carboxy-phenyl group may additionally be substituted in the phenyl nucleus by a fluorine, chlorine or bromine atom, by a $C_{1-3}$-alkyl, hydroxy, $C_{1-3}$-alkoxy, $C_{1-3}$-alkylsulphonyloxy or morpholino group, by an n-$C_{2-3}$-alkoxy group substituted in the 2 or 3 position by a di-($C_{1-3}$-alkyl)-amino group, by an N-methyl-N-(n-$C_{2-3}$-alkyl)-amino group substituted in the 2 or 3 position by a di-($C_{1-3}$-alkyl)-amino group, by an imidazolyl or pyrazolyl group optionally substituted by a $C_{1-4}$-alkyl group, by a $C_{1-4}$-alkylaminocarbonyl, N-(pyridinylmethyl)-aminocarbonyl, pyrrolidinoaminocarbonyl or piperidinoaminocarbonyl group and may additionally be substituted by another fluorine atom or by another methoxy group, the isomers thereof and the salts thereof.

The following are mentioned as examples of particularly preferred compounds:

(1) trans-3-(naphth-2-yl)-but-2-enoic acid-N-(2-carboxy-phenyl)-amide, (2) trans-3-(naphth-2-yl)-but-2-enoic acid-N-(2-carboxy-4,5-dimethoxy-phenyl)-amide, (3) trans-3-(naphth-2-yl)-but-2-enoic acid-N-(2-carboxy-4-fluoro-phenyl)-amide, (4) trans-3-(naphth-2-yl)-but-2-enoic acid-N-(2-carboxy-4,5-difluoro-phenyl)-amide, (5) trans-3-(naphth-2-yl)-but-2-enoic acid-N-(2-carboxy-5-fluoro-phenyl)-amide, (6) trans-3-(naphth-2-yl)-but-2-enoic acid-N-(2-carboxy-4-methoxy-5-methyl-phenyl)-amide, (7) trans-3-(naphth-2-yl)-but-2-enoic acid-N-[2-carboxy-4-(morpholin-4-yl)-phenyl]-amide, (8) trans-3-(naphth-2-yl)-but-2-enoic acid-N-(2-carboxy-4-dimethylamino-phenyl)-amide, (9) trans-3-(naphth-2-yl)-but-2-enoic acid-N-(2-carboxy-4-hydroxy-phenyl)-amide,

(10) trans-3-(naphth-2-yl)-but-2-enoic acid-N-(3-carboxy-thiophen-4-yl)-amide,

(11) trans-3-(naphth-2-yl)-but-2-enoic acid-N-[2-carboxy-4-(imidazol-1-yl)-phenyl]-amide,

(12) trans-3-(2-oxo-2H-chromen-3-yl)-but-2-enoic acid-N-(2-carboxy-phenyl)-amide,

(13) trans-3-(naphth-2-yl)-but-2-enoic acid-N-[2-carboxy-4-(imidazol-1-yl)-5-fluoro-phenyl]-amide,

(14) trans-3-(benzothiophen-2-yl)-but-2-enoic acid-N-(2-carboxy-phenyl)-amide,

(15) trans-3-(naphth-2-yl)-but-2-enoic acid-N-(2-carboxy-4-methanesulphonyloxyphenyl)-amide,

(16) trans-3-(naphth-2-yl)-but-2-enoic acid-N-[2-carboxy-4-(2-N,N-dimethylaminoethyloxy)-phenyl]-amide,

(17) trans-3-(naphth-2-yl)-but-2-enoic acid-N-(4-carboxy-pyridin-3-yl)-amide,

(18) trans-3-(3,4-dichlorphenyl)-but-2-enoic acid-N-(2-carboxy-4,5-dimethoxy-phenyl)-amide,

(19) trans-3-(3-chloro-4-bromophenyl)-but-2-enoic acid-N-(2-carboxy-phenyl)-amide,

(20) trans-3-(naphth-2-yl)-but-2-enoic acid-N-(2-carboxy-6-methyl-phenyl)-amide,

(21) trans-3-(naphth-2-yl)-but-2-enoic acid-N-(2-carboxy-6-fluoro-phenyl)-amide,

(22) trans-3-(naphth-2-yl)-but-2-enoic acid-N-[2-carboxy-5-(propylaminocarbonyl)-phenyl]-amide,

(23) trans-3-(naphth-2-yl)-but-2-enoic acid-N-[2-carboxy-5-(pyrrolidin-1-yl-aminocarbonyl)-phenyl]-amide,

(24) trans-3-(naphth-2-yl)-but-2-enoic acid-N-[2-carboxy-5-(N-(pyridin-3-yl-methyl)-aminocarbonyl)-phenyl]-amide,

(25) trans-3-(naphth-2-yl)-but-2-enoic acid-N-(2-carboxy-6-chloro-phenyl)-amide and the salts thereof.

The carboxylic acid amides of the above general formula I may be obtained, for example, by the following methods which are known per se:

a. acylating an amine of general formula

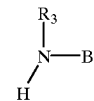

(II)

wherein $R_3$ and B are as hereinbefore defined, with a carboxylic acid of general formula

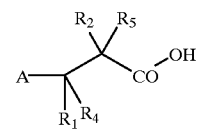

(III)

wherein $R_1$, $R_2$, $R_4$, $R_5$ and A are as hereinbefore defined, or the reactive derivatives thereof.

The acylation is conveniently carried out with a corresponding halide or anhydride in a solvent such as methylene chloride, chloroform, carbon tetrachloride, ether, tetrahydrofuran, dioxane, benzene, toluene, acetonitrile or sulpholane, optionally in the presence of an inorganic or organic base such as triethylamine, N-ethyl-diisopropylamine, N-methyl-morpholine or pyridine at temperatures between −20 and 200° C., but preferably at temperatures between −10 and 160° C.

However, the acylation may also be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexyl-carbodiimide/N-hydroxysuccinimide or 1-hydroxy-benzotriazole, N,N'-carbonyldiimidazole or N,N'-thionyldiimidazole or triphenylphosphine/carbon tetrachloride, at temperatures between −20 and 200° C., but preferably at temperatures between −10 and 160° C.

b. In order to prepare a carboxylic acid amide of general formula I which contains a carboxy group:

converting a compound of general formula

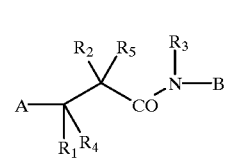

(IV)

wherein $R_1$ to $R_5$, A and B are as hereinbefore defined, with the proviso that A or B or A and B contain a group which can be converted into a carboxy group, into a compound of general formula I which contains a carboxy group. Examples of a group which can be converted into a carboxy group include carboxyl groups protected by protecting groups, such as the functional derivatives thereof, e.g. the unsubstituted or substituted amides, esters, thirsters, trimethylsilylesters, orthoesters or iminoesters thereof, which are conveniently converted into a carboxyl group by hydrolysis, the esters thereof with tertiary alcohols, e.g. the tert. butyl ester, which are conveniently converted into a carboxyl group by treating with an acid or by thermolysis, and the esters thereof with aralkanols, e.g. the benzyl ester, which are conveniently converted into a carboxyl group by hydrolysis.

The hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

The conversion of a tert. butyl or tert. butyloxycarbonyl group into a carboxy group can also be carried out by treating with an acid such as trifluoroacetic acid, formic acid, p-to-luenesulphonic acid, sulphuric acid, hydrochloric acid, phosphoric acid or polyphosphoric acid optionally in an inert solvent such as methylene chloride, chloroform, benzene, toluene, diethylether, tetrahydrofuran or dioxane, preferably at temperatures between -10 and 120° C., e.g. at temperatures between 0 and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C.

The conversion of a benzyloxy or benzyloxycarbonyl group into a carboxy group may also be carried out hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at ambient temperature, and at a hydrogen pressure of 1 to 5 bar.

If according to the invention a compound of general formula I is obtained which contains a hydroxy group, this may be converted into a corresponding sulphonyloxy compound by means of a sulphonyl halide, or if a compound of general formula I is obtained which contains a cyano group, this can be converted by means of hydrazoic acid into a corresponding tetrazolyl compound, or if a compound of general formula I is obtained which contains an amino or imino group with a basic hydrogen atom, this can be converted by acylation or sulphonylation into a correspondingly acylated compound or into a corresponding prodrug compound, or if a compound of general formula I is obtained which contains a carboxy group, this can be converted into a compound which contains a group which may be converted into a carboxy group in vivo, or if a compound of general formula I is obtained which contains one or two carboxy groups, this can be converted by reduction with a complex metal hydride into a compound which contains one or two hydroxymethyl groups.

The subsequent sulphonylation is conveniently carried out with a corresponding halide in a solvent such as methylene chloride, chloroform, carbon tetrachloride, ether, tetrahydrofuran, dioxane, benzene, toluene, acetonitrile or sulpholane, optionally in the presence of an inorganic or organic base such as triethylamine, N-ethyl-diisopropylamine, N-methyl-morpholine or pyridine at temperatures between −20 and 200° C., but preferably at temperatures between −10 and 160° C.

The subsequent preparation of a compound of general formula I which contains a tetrazole group is preferably carried out in a solvent such as benzene, toluene or dimethylformamide at temperatures between 80 and 150° C., preferably between 120 and 130° C. The hydrazoic acid required is conveniently liberated during the reaction from an alkali metal azide, e.g. from sodium azide, in the presence of a weak acid such as ammonium chloride. The reaction may also be carried out with another salt or derivative of hydrazoic acid, preferably with aluminium azide or tributyl tin azide, and the tetrazole compound optionally obtained in this way is then liberated from the salt contained in the reaction mixture by acidification with a dilute acid such as 2N hydrochloric acid or 2N sulphuric acid.

The subsequent acylation or sulphonylation or the subsequent conversion into a corresponding prodrug compound is preferably carried out with a corresponding acid halide in a solvent such as methylene chloride, chloroform, carbon tetrachloride, ether, tetrahydrofuran, dioxane, benzene, toluene, acetonitrile or sulpholane, optionally in the presence of an inorganic or organic base such as triethylamine, N-ethyl-diisopropylamine, N-methyl-morpholine or pyridine at temperatures between −20 and 200° C., but preferably at temperatures between −10 and 160° C.

The subsequent conversion of a carboxy group into a group which may be converted into a carboxy group in vivo is preferably carried out by esterification with a corresponding alcohol or by alkylation of the carboxy group. The esterification is conveniently carried out in a solvent or mixture of solvents such as methylene chloride, benzene, toluene, chlorobenzene, tetrahydrofuran, benzene/tetrahydrofuran or dioxane, but preferably in an excess of the alcohol reactant in the presence of a dehydrating agent, e.g. in the presence of hydrochloric acid, sulphuric acid, isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, 2-(1H-benzotriazol-1-yl)-1,1,3,3-tetramethyluronium-tetrafluoroborate, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyl-diisopropylamine or N,N-dimethylaminopyridine, conveniently at temperatures between 0 and 150° C., preferably at temperatures between 0 and 80° C., and the alkylation is conveniently carried out with a corresponding halide in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously serve as solvent, or optionally in the presence of silver carbonate or silver oxide at temperatures between −30 and 100° C., but preferably at temperatures between −10 and 80° C.

The subsequent reduction is preferably carried out in the presence of a complex metal hydride such as lithium aluminium hydride or lithium triethyl borohydride in a solvent such as tetrahydrofuran, conveniently at the boiling temperature of the solvent used.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, protecting groups for a carboxy group may be a trimethylsilyl, methyl, ethyl, tert.butyl, benzyl or tetrahydropyranyl group and protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxan, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

The compounds of general formulae II to IV used as starting materials are known from the literature in some cases but may also be prepared by methods known from the literature (cf for example Fulton et al. in J.Chem.Soc. 1939, page 200, S. Sano et al. in Chem.Commun. 6, page 539 (1997) and D. H. Klaubert et al. in J.Med.Chem. 24, 742–748 (1981)).

Moreover, the compounds of general formula I obtained may be resolved into their enantiomers and/or diastereomers, as mentioned hereinbefore. Thus, for example, compounds with at least one optically active carbon atom may be separated into their enantiomers.

Thus, for example, the compounds of general formula I obtained which occur as racemates may be separated by methods known per se (cf. Alliner N. L. and Eliel E. L. in "Topics in Stereochemistry", Vol. 6, Wiley Interscience, 1971) into their optical enantiomers and compounds of general formula I with at least 2 stereogenic centres may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain an acidic group such as a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

As already mentioned hereinbefore, the carboxylic acid amides of general formula I and the salts thereof, particularly the physiologically acceptable salts thereof, have an inhibiting effect on telomerase.

The inhibiting effect of the carboxylic acid amides of general formula I on telomerase was investigated as follows:

MATERIALS AND METHODS

1. Preparation of nuclear extracts from HeLa cells: Nuclear extracts were prepared according to Dignam (Dignam et al. in Nucleic Acids Res. 11, 1475–1489 (1983)). All the steps were carried out at 4° C., all the equipment and solutions were pre-cooled to 4° C. At least $1\times10^9$ HeLa-S3 cells growing in suspension culture (ATCC catalogue number CCL-2.2) were harvested by centrifuging for 5 minutes at 1000×g and washed once with PBS buffer (140 mM KCl; 2.7 mM KCl; 8.1 mM $Na_2HPO_4$; 1.5 mM $KH_2PO_4$). After the cell volume had been determined, the cells were suspended in 5 times the volume of hypotonic buffer (10 mM HEPES/KOH, pH 7.8; 10 mM KCl; 1.5 mM $MgCl_2$) and then left for 10 minutes at 4° C. After centrifuging for 5 minutes at 1000×g the cell pellet was suspended in twice the volume of hypotonic buffer in the presence of 1 mM DTE and 1 mM PMSF and broken up with a Dounce homogeniser. The homogenised material was made isotonic with 0.1 volume of 10-fold saline buffer (300 mM HEPES/KOH, pH 7.8; 1.4 M KCl; 30 mM $MgCl_2$). The cell nuclei were separated from the ingredients of the cytoplasm by centrifuging and then suspended in twice the volume of nuclear extraction buffer (20 mM HEPES/KOH, pH 7.9; 420 mM KCl; 1.5 mM $MgCl_2$; 0.2 mM EDTA; 0.5 mM DTE; 25% glycerol). The nuclei were broken up using a Dounce homogeniser and incubated for 30 minutes at 4° C. with gentle stirring. Any insoluble ingredients were removed by centrifuging for 30 minutes at 10.000 rpm (SS-34 Rotor). Then the nuclear extract was dialysed for 4–5 hours against AM-100 buffer (20 mM tris/HCl, pH 7.9; 100 mM KCl; 0.1 mM EDTA; 0.5 mM DTE; 20% glycerol). The nuclear extracts obtained were frozen in liquid nitrogen and stored at −80° C.

2. Telomerase test: The activity of telomerase in nuclear extracts from HeLa cells was determined using the method described by Morin (Morin in Cell 59 521–529 (1989)). The nuclear extract (up to 20 μl per reaction) was incubated for 120 minutes at 30° C. in a volume of 40 μl in the presence of 25 mM Tris/HCl pH 8.2, 1.25 mM dATP, 1.25 mM TTP, 6.35 μM dGTP; 15 μCi α-$^{32}$P-dGTP (3000 Ci/mmol), 1 mM MgCl$_2$, 1 mM EGTA, 1.25 mM spermidine, 0.25 U RNasin, and 2.5 μM of an oligonucleotide primer (for example TEA-fw [CAT ACT GGC GAG CAG AGT T], or TTA GGG TTA GGG TTA GGG) (=telomerase reaction). If the inhibition constant of potential telomerase inhibitors was to be determined, these were also added to the telomerase reaction in a concentration range of from 1 nM to 100 μM.

The reaction was then stopped by the addition of 50 μl of RNase stop buffer (10 mM tris/HCL, pH 8.0; 20 mM EDTA; 0.1 mg/ml of RNase A 100 U/ml of RNase T1; 1000 cpm of an α-$^{32}$P-dGTP labelled, 430 bp DNA fragment) and incubation was continued for a further 15 minutes at 37° C. Proteins present in the reaction mixture were cleaved by the addition of 50 μl of proteinase K buffer (10 mM tris/HCL, pH 8.0; 0.5% SDS; 0.3 mg/ml of proteinase K) and subsequent incubation for 15 min at 37° C. The DNA was purified by extracting twice with phenol-chloroform and precipitated by adding 2.4 M ammonium acetate; 3 μg tRNA and 750 μl ethanol. Then the precipitated DNA was washed with 500 μl of 70% ethanol, dried at ambient temperature, taken up in 4 μl of formamide probe buffer (80% (V/V) formamide; 50 mM of tris-borate, pH 8.3; 1 mM EDTA; 0.1 (w/v) of xylene cyanol; 0.1% (w/v) bromophenol blue) and separated by electrophoresis on a sequence gel (8% polyacrylamide, 7 M urea, 1×TBE buffer). The DNA synthesised by telomerase in the presence or absence of potential inhibitors was identified and quantified by Phospho-Imager Analysis (Molecular Dynamics) and in this way the concentration of inhibitor which inhibits the telomerase activity by 50% (IC$_{50}$) was determined. The radiolabelled DNA fragment to which the RNase stop buffer had been added was used as an internal control for the yield.

The following Table gives the IC$_{50}$ values of some inhibitors by way of example:

| Example No. | IC$_{50}$ [μM] |
| --- | --- |
| 10 | 5.0 |
| 17 | 1.0 |
| 18 | 0.04 |
| 28 | 0.035 |
| 29 | 0.55 |
| 31 | 0.10 |

The following abbreviations were used in the foregoing description:

| | |
| --- | --- |
| bp | base pairs |
| DNA | deoxyribonucleic acid |
| DTE | 1,4-dithioerythritol |
| dATP | deoxyadenosine triphosphate |
| dGTP | deoxyguanosine triphosphate |
| EDTA | ethylendiamine-tetraacetic acid |
| EGTA | ethyleneglycol-bis-(2-aminoethyl)-tetraacetic acid |
| HEPES | 4-(2-hydroxyethyl)-piperazine-1-ethanesulphonic acid |
| PMSF | phenylmethanesulphonylfluoride |
| RNase | ribonuclease |
| RNasin ® | ribonuclease inhibitor (Promega GmbH, Mannheim) |
| tRNA | transfer ribonucleic acid |
| TTP | thymidine triphosphate |
| TRIS | tris-(hydroxymethyl)-aminomethane |
| TBE | TRIS-borate-EDTA |
| rpm | revolutions per minute |

In view of their biological properties, the carboxylic acid amides of general formula I are suitable for treating pathophysiological processes which are characterised by an increased telomerase activity. These are e.g. tumour diseases such as carcinomas, sarcomas and leukaemias including skin cancer (e.g. plate epithelial carcinoma, basalioma, melanoma), small-cell bronchial carcinoma, non-small-cell bronchial carcinoma, salivary gland carcinoma, oesophageal carcinoma, laryngeal carcinoma, pharyngeal carcinoma, thyroid carcinoma, gastric carcinoma, colorectal carcinoma, pancreatic carcinoma, carcinoma of the liver, carcinoma of the breast, uterine carcinoma, vaginal carcinoma, ovarian carcinoma, prostate carcinoma, testicular carcinoma, bladder carcinoma, renal carcinoma, Wilms' tumour, retinoblastoma, astrocytoma, oligodendroglioma, meningioma, neuroblastoma, myeloma, medulloblastoma, neurofibrosarcoma, thymoma, osteosarcoma, chondrosarcoma, Ewing's sarcoma, fibrosarcoma, histiocytoma, dermatofibrosarcoma, synovialoma, leiomyosarcoma, rhabdomyosarcoma, liposarcoma, Hodgkin's lymphoma, non-Hodgkin's lymphoma, chronic myeloid leukaemia, chronic lymphatic leukaemia, acute promyelocytic leukaemia, acute lymphoblastoid leukaemia and acute myeloid leukaemia.

In addition, the compounds may also be used to treat other diseases which have an increased rate of cell division or increased telomerase activity, such as e.g. epidermal hyperproliferation (psoriasis), inflammatory processes (rheumatoid arthritis), diseases of the immune system, etc.

The compounds are also useful for treating parasitic diseases in man and animals, such as e.g. worm or fungal diseases as well as diseases caused by protozoan pathogens, such as e.g. Zooflagellata (Trypanosoma, Leishmania, Giardia), Rhizopoda (Entamoeba spp.), Sporozoa (Plasmodium spp., Toxoplasma spp.), Ciliata, etc.

For this purpose the carboxylic acid amides of general formula I may optionally be used in conjunction with other pharmacologically active compounds and therapeutic preparations which will reduce tumour size and incorporated in conventional galenic preparations. These may be used, for example, in tumour therapy, in monotherapy or in conjunction with irradiation, surgical interventions or other antitumour therapeutics, e.g. in conjunction with topoisomerase inhibitors (e.g. etoposide), mitosis inhibitors (e.g. paclitaxel, vinblastin), cell cycle inhibitors (e.g. flavopyridol), inhibitors of signal transduction (e.g. farnesyltransferase inhibitors), compounds which interact with nucleic acid (e.g. cis-platin, cyclophosphamide, adriamycin), hormone antagonists (e.g. tamoxifen), inhibitors of metabolic processes (e.g. 5-FU etc.), cytokines (e.g. interferons), tumour vaccines, antibodies, etc. These combinations may be given either simultaneously or sequentially.

The daily dose is 20 to 600 mg by oral or intravenous route, divided up into one to four doses a day. For this purpose the compounds of general formula I, optionally in conjunction with the other active substances mentioned above, may be formulated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof to produce conventional galenic preparations such as plain or coated tablets, capsules, powders, suspensions or suppositories.

The following Examples are intended to illustrate the invention in more detail:

EXAMPLE 1

Trans-3-nitrocinnamic acid-N-(2-methoxycarbonyl-phenyl)-amide 965 mg (5.0 mmol) of trans-3-nitrocinnamic acid are refluxed for 20 minutes in 3 ml of thionyl chloride after the addition of one drop of dimethylformamide. Then the mixture is evaporated to dryness in vacuo and the resulting acid chloride is dissolved in 10 ml of dioxane. This solution is slowly added dropwise, with stirring, at ambient temperature, to a solution of 756 mg (5.0 mmol) of methyl anthranilate and 1.5 ml of triethylamine in 10 ml of dioxane. After one hour the solvent is evaporated off in vacuo, the residue is stirred into about 10 ml of water, then filtered off and the resulting crude product is purified by column chromatography over silica gel (eluant: dichloromethane/petroleum ether=2:1).

| | |
|---|---|
| Yield: | 990 mg (61% of theory), $C_{17}H_{14}N_2O_5$ (326.32) |
| $R_f$ value: | 0.20 (silica gel; dichloromethane/petroleum ether = 2:1) |
| $R_f$ value: | 0.88 (silica gel; dichloromethane/ethanol = 9:1) |
| mass spectrum: | $M^+ = 326$ |

EXAMPLE 2

Trans-3-nitrocinnamic acid-N-(2-carboxy-phenyl)-amide 500 mg (1.53 mmol) of trans-3-nitrocinnamic acid-N-(2-methoxycarbonyl-phenyl)-amide are stirred into a mixture of 20 ml of methanol and 8 ml of 2N sodium hydroxide solution for two hours at 50° C. Then the methanol is distilled off in vacuo, the residue is diluted with about 150 ml of water and adjusted to about pH 2.5 with stirring. The product which is then precipitated is suction filtered, washed with about 10 ml of water and dried.

| | |
|---|---|
| Yield: | 420 mg (88% of theory), $C_{16}H_{12}N_2O_5$ (312.29) |
| $R_f$ value: | 0.39 (silica gel; dichloromethane/ethanol = 9:1) |
| mass spectrum: | $(M - H)^- = 311$ |

Rf value: 0.39 (silica gel; dichloromethane/ethanol=9:1) mass spectrum: $(M-H)^- = 311$

EXAMPLE 3

Trans-3-(3,4-dichlorophenyl)-but-2-enoic acid-N-(3-ethoxycarbonyl-phenyl)-amide

Prepared analogously to Example 1 from trans-3-(3,4-dichlorophenyl)-but-2-enoic acid and ethyl 3-aminobenzoate.

| | |
|---|---|
| Yield: | 29% of theory, $C_{19}H_{17}Cl_2NO_3$ (378.27) |
| $R_f$ value: | 0.84 (silica gel; petroleum ether/ethyl acetate = 2:1) |
| mass spectrum: | $M^+ = 377/379/381$ |

EXAMPLE 4

Trans-3-(3,4-dichlorophenyl)-but-2-enoic acid-N-(3-carboxy-phenyl)-amide

Prepared analogously to Example 2 from trans-3-(3,4-dichlorophenyl)-but-2-enoic acid-N-(3-ethoxycarbonyl-phenyl)-amide and sodium hydroxide solution in ethanol.

| | |
|---|---|
| Yield: | 69% of theory, $C_{17}H_{13}Cl_2NO_3$ (350.21) |
| $R_f$ value: | 0.21 (silica gel; dichloromethane/ethanol = 19:1) |
| mass spectrum: | $M^+ = 349/351/353$ |

EXAMPLE 5

Trans-3-(3,4-dichlorophenyl)-but-2-enoic acid-N-(4-ethoxycarbonyl-phenyl)-amide

Prepared analogously to Example 1 from trans-3-(3,4-dichlorophenyl)-but-2-enoic acid and ethyl 4-aminobenzoate.

| | |
|---|---|
| Yield: | 16% of theory, $C_{19}H_{17}Cl_2NO_3$ (378.27) |
| $R_f$ value: | 0.46 (silica gel; petroleum ether/ethyl acetate = 2:1) |
| mass spectrum: | $M^+ = 377/379/381$ |

EXAMPLE 6

Trans-3-(3,4-dichlorophenyl)-but-2-enoic acid-N-(4-carboxy-phenyl)-amide

Prepared analogously to Example 2 from trans-3-(3,4-dichlorophenyl)-but-2-enoic acid-N-(4-ethoxycarbonyl-phenyl)-amide and sodium hydroxide solution in ethanol.

Yield: 78% of theory, $C_{17}H_{13}Cl_2NO_3$ (350.21); $R_f$ value: 0.24 (silica gel; dichloromethane/ethanol=19:1); mass spectrum: $M^+=349/351/353$

EXAMPLE 7

Trans-3-(3,4-dichlorophenyl)-but-2-enoic acid-N-(5-chloro-2-methoxycarbonyl-phenyl)-amide Prepared analogously to Example 1 from trans-3-(3,4-dichlorophenyl)-but-2-enoic acid and methyl 2-amino-4-chloro-benzoate.

| | |
|---|---|
| Yield: | 33% of theory, |
| | $C_{18}H_{14}Cl_3NO_3$ (398.69) |
| $R_f$ value: | 0.43 (silica gel; petroleum ether/ethyl acetate = 2:1) |
| mass spectrum: | $M^+$ = 397/399/401 |

EXAMPLE 8

Trans-3-(3,4-dichlorophenyl)-but-2-enoic acid-N-(2-carboxy-5-chloro-phenyl)-amide Prepared analogously to Example 2 from trans-3-(3,4-dichlorophenyl)-but-2-enoic acid-N-(5-chloro-2-methoxycarbonyl-phenyl)-amide and sodium hydroxide solution in ethanol.

| | |
|---|---|
| Yield: | 69% of theory, |
| | $C_{17}H_{12}Cl_3NO_3$ (384.66) |
| $R_f$ value: | 0.27 (silica gel; dichloromethane/ethanol = 19:1) |
| mass spectrum: | $M^+$ = 383/385/387 |

EXAMPLE 9

Trans-3-(3,4-dichlorophenyl)-but-2-enoic acid-N-(2-methoxycarbonyl-phenyl)-amide Prepared analogously to Example 1 from trans-3-(3,4-dichlorophenyl)-but-2-enoic acid and methyl 2-aminobenzoate.

| | |
|---|---|
| Yield: | 73% of theory, |
| | $C_{18}H_{15}Cl_2NO_3$ (364.23) |
| $R_f$ value: | 0.39 (silica gel; petroleum ether/ethyl acetate = 2:1) |
| mass spectrum: | $M^+$ = 363/365/367 |

EXAMPLE 10

Trans-3-(3,4-dichlorophenyl)-but-2-enoic acid-N-(2-carboxy-phenyl)-amide

Prepared analogously to Example 2 from trans-3-(3,4-dichlorophenyl)-but-2-enoic acid-N-(2-methoxycarbonyl-phenyl)-amide and sodium hydroxide solution in ethanol.

| | |
|---|---|
| Yield: | 76% of theory, |
| | $C_{17}H_{13}Cl_2NO_3$ (350.20) |
| $R_f$ value: | 0.25 (silica gel; dichloromethane/ethanol = 19:1) |
| mass spectrum: | $M^+$ = 349/351/353 |

EXAMPLE 11

Trans-4-n-pentylcinnamic acid-N-(2-carboxy-5-chlorophenyl)-amide

Prepared analogously to Example 2 from trans-4-n-pentylcinnamic acid-N-(5-chloro-2-methoxycarbonyl-phenyl)-amide and sodium hydroxide solution in ethanol.

| | |
|---|---|
| Yield: | 71% of theory, |
| | $C_{21}H_{22}ClNO_3$ (371.86) |
| $R_f$ value: | 0.33 (silica gel; dichloromethane/ethanol = 19:1) |
| mass spectrum: | $M^+$ = 371/373 |

EXAMPLE 12

Trans-4-n-pentylcinnamic acid-N-(2-carboxy-phenyl)-amide

Prepared analogously to Example 2 from trans-4-n-pentylcinnamic acid-N-(2-methoxycarbonyl-phenyl)-amide and sodium hydroxide solution in methanol.

| | |
|---|---|
| Yield: | 77% of theory, |
| | $C_{21}H_{23}NO_3$ (337.42) |
| $R_f$ value: | 0.30 (silica gel; dichloromethane/ethanol = 19:1) |
| mass spectrum: | $M^+$ = 337 |

EXAMPLE 13

Trans-3-(4-trifluoromethylphenyl)-but-2-enoic acid-N-(2-carboxy-phenyl)-amide

Prepared analogously to Example 2 from trans-3-(4-trifluoromethylphenyl)-but-2-enoic acid-N-(2-methoxycarbonyl-phenyl)-amide and sodium hydroxide solution in methanol.

| | |
|---|---|
| Yield: | 31% of theory, |
| | $C_{18}H_{14}F_3NO_3$ (349.32) |
| $R_f$ value: | 0.25 (silica gel; dichloromethane/ethanol = 19:1) |
| mass spectrum: | $M^+$ = 349 |

EXAMPLE 14

Trans-3-(biphenyl-4-yl)-but-2-enoic acid-N-(2-carboxy-phenyl)-amide

Prepared analogously to Example 2 from trans-3-(biphenyl-4-yl)-but-2-enoic acid-N-(2-methoxycarbonyl-phenyl)-amide and sodium hydroxide solution in ethanol.

| | |
|---|---|
| Yield: | 11% of theory, |
| | $C_{23}H_{19}NO_3$ (357.41) |
| $R_f$ value: | 0.38 (silica gel; dichloromethane/ethanol = 19:1) |
| mass spectrum: | $M^+$ = 357 |

EXAMPLE 15

Trans-3-(3,4-dichlorophenyl)-but-2-enoic acid-N-(2-carboxy-4-methyl-phenyl)-amide Prepared analogously to Example 2 from trans-3-(3,4-dichlorophenyl)-but-2-enoic acid-N-(2-methoxycarbonyl-4-methyl-phenyl)-amide and sodium hydroxide solution in ethanol.

| Yield: | 20% of theory, |
| --- | --- |
| | $C_{18}H_{15}Cl_2NO_3$ (364.24) |
| $R_f$ value: | 0.30 (silica gel; dichloromethane/ethanol = 19:1) |
| mass spectrum: | $M^+$ = 363/365/367 |

EXAMPLE 16

Trans-3-(3,4-dichlorophenyl)-but-2-enoic acid-N-(2-carboxy-4,5-dimethoxy-phenyl)-amide Prepared analogously to Example 2 from trans-3-(3,4-dichlorophenyl)-but-2-enoic acid-N-(4,5-dimethoxy-2-methoxycarbonyl-phenyl)-amide and sodium hydroxide solution in ethanol.

| Yield: | 54% of theory, |
| --- | --- |
| | $C_{19}H_{17}Cl_2NO_5$ (410.27) |
| $R_f$ value: | 0.31 (silica gel; dichloromethane/ethanol = 19:1) |
| mass spectrum: | $M^+$ = 409/411/413 |

EXAMPLE 17

Trans-3-(3,4-dichlorophenyl)-but-2-enoic acid-N-(2-carboxy-4-methoxy-5-methyl-phenyl)-amide Prepared analogously to Example 2 from trans-3-(3,4-dichlorophenyl)-but-2-enoic acid-N-(4-methoxy-2-methoxycarbonyl-5-methyl-phenyl)-amide and sodium hydroxide solution in methanol.

| Yield: | 44% of theory, |
| --- | --- |
| | $C_{19}H_{17}Cl_2NO_4$ (394.26) |
| $R_f$ value: | 0.32 (silica gel; dichloromethane/ethanol = 19:1) |
| mass spectrum: | $M^+$ = 393/395/397 |

EXAMPLE 18

Trans-3-(naphth-2-yl)-but-2-enoic acid-N-(2-carboxy-phenyl)-amide

Prepared analogously to Example 2 from trans-3-(naphth-2-yl)-but-2-enoic acid-N-(2-methoxycarbonyl-phenyl)-amide and sodium hydroxide solution in ethanol.

| Yield: | 18% of theory, |
| --- | --- |
| | $C_{21}H_{17}NO_3$ (331.38) |
| $R_f$ value: | 0.30 (silica gel; dichloromethane/ethanol = 19:1) |
| mass spectrum: | $M^+$ = 331 |

EXAMPLE 19

Trans-3-(naphth-2-yl)-but-2-enoic acid-N-[2-carboxy-5-(methoxyaminocarbonyl)-phenyl]-amide Prepared analogously to Example 2 from trans-3-(naphth-2-yl)-but-2-enoic acid-N-[2-methoxycarbonyl-5-(methoxyaminocarbonyl)-phenyl]-amide and lithium hydroxide in methanol/water.

| Yield: | 52% of theory, |
| --- | --- |
| | $C_{23}H_{20}N_2O_5$ (404.42) |
| mass spectrum: | $(M - H)^-$ = 403 |
| | $(M + Na)^+$ = 427 |

EXAMPLE 20

Trans-3-(3,4-dichlorophenyl)-but-2-enoic acid-N-(4-bromo-2-carboxy-6-methyl-phenyl)-amide Prepared analogously to Example 2 from trans-3-(3,4-dichlorophenyl)-but-2-enoic acid-N-(4-bromo-2-methoxycarbonyl-6-methyl-phenyl)-amide and sodium hydroxide solution in methanol.

| Yield: | 43% of theory, |
| --- | --- |
| | $C_{18}H_{14}BrCl_2NO_3$ (443.15) |
| $R_f$ value: | 0.31 (silica gel; dichloromethane/ethanol = 19:1) |
| mass spectrum: | $M^+$ = 441/443/445 |

EXAMPLE 21

Trans-3-(naphth-2-yl)-but-2-enoic acid-N-[2-carboxy-5-(2-acetyl-hydrazino-carbonyl)-phenyl]-amide Prepared analogously to Example 2 from trans-3-(naphth-2-yl)-but-2-enoic acid-N-[2-methoxycarbonyl-5-(2-acetylhydrazino-carbonyl)-phenyl]-amide and lithium hydroxide in methanol/water.

| Yield: | 35% of theory, |
| --- | --- |
| | $C_{24}H_{21}N_3O_5$ (431.45) |
| $R_f$ value: | 0.18 (silica gel; dichloromethane/ethanol = 3:1) |
| mass spectrum: | $(M - H)^-$ = 430 |
| | $(M + Na)^+$ = 454 |

EXAMPLE 22

Trans-3-(naphth-2-yl)-but-2-enoic acid-N-[2-carboxy-5-(N-pyridin-3-yl-aminocarbonyl)-phenyl]-amide Prepared analogously to Example 2 from trans-3-(naphth-2-yl)-but-2-enoic acid-N-[2-methoxycarbonyl-5-(N-pyridin-3-yl-aminocarbonyl)-phenyl]-amide and lithium hydroxide in methanol/water.

| Yield: | 62% of theory, |
| --- | --- |
| | $C_{27}H_{21}N_3O_4$ (451.48) |
| mass spectrum: | $(M - H)^-$ = 450 |

EXAMPLE 23

Trans-3-(3,4-dichlorophenyl)-but-2-enoic acid-N-(2-carboxy-5-nitro-phenyl)-amide Prepared analogously to Example 2 from trans-3-(3,4-dichlorophenyl)-but-2-enoic acid-N-(2-methoxycarbonyl-5- nitro-phenyl)-amide and sodium hydroxide solution in methanol.

| | |
|---|---|
| Yield: | 16% of theory, $C_{17}H_{12}Cl_2N_2O_5$ (395.21) |
| $R_f$ value: | 0.24 (silica gel; dichloromethane/ethanol = 9:1) |
| mass spectrum: | $M^+$ = 394/396/398 |

EXAMPLE 24

Trans-3-(3,4-dichlorophenyl)-but-2-enoic acid-N-(3-carboxy-naphth-2-yl)-amide

Prepared analogously to Example 2 from trans-3-(3,4-dichlorophenyl)-but-2-enoic acid-N-(3-methoxycarbonyl-naphth-2-yl)-amide and sodium hydroxide solution in methanol.

| | |
|---|---|
| Yield: | 14% of theory, $C_{21}H_{15}Cl_2NO_3$ (400.27) |
| $R_f$ value: | 0.29 (silica gel; dichloromethane/ethanol = 19:1) |
| mass spectrum: | $M^+$ = 399/401/403 |

EXAMPLE 25

Trans-4-chlorocinnamic acid-N-(2-carboxy-phenyl)-amide

Prepared analogously to Example 2 from trans-4-chlorocinnamic acid-N-(2-methoxycarbonyl-phenyl)-amide and sodium hydroxide solution in methanol.

| | |
|---|---|
| Yield: | 53% of theory, $C_{16}H_{12}ClNO_3$ (301.73) |
| $R_f$ value: | 0.26 (silica gel; dichloromethane/ethanol = 19:1) |
| mass spectrum: | $M^+$ = 301/303 |

EXAMPLE 26

Trans-3-(3,4-dichlorophenyl)-but-2-enoic acid-N-(2-carboxy-4-iodo-phenyl)-amide

Prepared analogously to Example 2 from trans-3-(3,4-dichlorophenyl)-but-2-enoic acid-N-(2-methoxycarbonyl-4-iodo-phenyl)-amide and sodium hydroxide solution in methanol.

| | |
|---|---|
| Yield: | 23% of theory, $C_{17}H_{12}Cl_2INO_3$ (476.11) |
| $R_f$ value: | 0.23 (silica gel; dichloromethane/ethanol = 19:1) |
| mass spectrum: | $M^+$ = 475/477/479 |

EXAMPLE 27

Trans-3-(3,4-dichlorophenyl)-but-2-enoic acid-N-(2-carboxy-4-chlorophenyl)-amide Prepared analogously to Example 2 from trans-3-(3,4-dichlorophenyl)-but-2-enoic acid-N-(2-methoxycarbonyl-4-chlorophenyl)-amide and sodium hydroxide solution in methanol.

| | |
|---|---|
| Yield: | 18% of theory, $C_{17}H_{12}Cl_3NO_3$ (384.66) |
| $R_f$ value: | 0.31 (silica gel; dichloromethane/ethanol = 9:1) |
| mass spectrum: | $M^+$ = 383/385/387 |

EXAMPLE 28

Trans-3-(naphth-2-yl)-but-2-enoic acid-N-(2-carboxy-4,5-dimethoxy-phenyl)-amide

Prepared analogously to Example 2 from trans-3-(naphth-2-yl)-but-2-enoic acid-N-(2-methoxycarbonyl-4,5-dimethoxy-phenyl)-amide and sodium hydroxide solution in methanol.

| | |
|---|---|
| Yield: | 59% of theory, $C_{23}H_{21}NO_5$ (391.43) |
| $R_f$ value: | 0.30 (silica gel; dichloromethane/ethanol = 19:1) |
| mass spectrum: | $M^+$ = 391 |

EXAMPLE 29

Trans-3-(naphth-2-yl)-but-2-enoic acid-N-(2-carboxy-5-chloro-phenyl)-amide

Prepared analogously to Example 2 from trans-3-(naphth-2-yl)-but-2-enoic acid-N-(2-methoxycarbonyl-5-chloro-phenyl)-amide and sodium hydroxide solution in ethanol.

| | |
|---|---|
| Yield: | 13% of theory, $C_{21}H_{16}ClNO_3$ (365.82) |
| $R_f$ value: | 0.26 (silica gel; dichloromethane/ethanol = 19:1) |
| mass spectrum: | $M^+$ = 365/367 |

EXAMPLE 30

Trans-3-(naphth-2-yl)-but-2-enoic acid-N-(2-carboxy-4-methoxy-phenyl)-amide

Prepared analogously to Example 2 from trans-3-(naphth-2-yl)-but-2-enoic acid-N-(2-methoxycarbonyl-4-methoxy-phenyl)-amide and sodium hydroxide solution in methanol.

| | |
|---|---|
| Yield: | 56% of theory, $C_{22}H_{19}NO_4$ (361.40) |
| $R_f$ value: | 0.25 (silica gel; dichloromethane/ethanol = 19:1) |
| mass spectrum: | $M^+$ = 361 |

EXAMPLE 31

Trans-3-(naphth-2-yl)-but-2-enoic acid-N-(2-carboxy-4-fluoro-phenyl)-amide 577 mg (2.5 mmol) of trans-3-(naphth-2-yl)-but-2-enoic acid chloride, dissolved in 10 ml of tetrahydrofuran, are slowly added dropwise at ambient temperature with stirring to a solution of 388 mg (2.5 mmol) of 2-amino-5-fluoro-benzoic acid and 303 mg of triethylamine in 20 ml of tetrahydrofuran. The mixture is stirred for a further 17 hours at ambient temperature, then the solvent is evaporated in vacuo and the resulting crude product is purified by column chromatography over silica gel (eluant: dichloromethane with 1 to 2% ethanol).

| Yield: | 180 mg (21% of theory), $C_{21}H_{16}FNO_3$ (349.37) |
|---|---|
| $R_f$ value: | 0.21 (silica gel; dichloromethane/ethanol = 19:1) |
| mass spectrum: | $M^+$ = 349 |

EXAMPLE 32

Trans-3-(naphth-2-yl)-but-2-enoic acid-N-(3-carboxy-naphth-2-yl)-amide

Prepared analogously to Example 2 from trans-3-(naphth-2-yl)-but-2-enoic acid-N-(3-methoxycarbonyl-naphth-2-yl)-amide and sodium hydroxide solution in methanol.

| Yield: | 50% of theory, $C_{25}H_{19}NO_3$ (381.44) |
|---|---|
| $R_f$ value: | 0.31 (silica gel; dichloromethane/ethanol = 19:1) |
| mass spectrum: | $M^+$ = 381 |

EXAMPLE 33

Trans-3-(naphth-2-yl)-but-2-enoic acid-N-(2-carboxy-4-chloro-phenyl)-amide

Prepared analogously to Example 2 from trans-3-(naphth-2-yl)-but-2-enoic acid-N-(2-methoxycarbonyl-4-chloro-phenyl)-amide and sodium hydroxide solution in methanol.

| Yield: | 27% of theory, $C_{21}H_{16}ClNO_3$ (365.82) |
|---|---|
| $R_f$ value: | 0.24 (silica gel; dichloromethane/ethanol = 19:1) |
| mass spectrum: | $M^+$ = 365/367 |

EXAMPLE 34

Trans-3-(naphth-2-yl)-but-2-enoic acid-N-(2-carboxy-4-methyl-phenyl)-amide

Prepared analogously to Example 31 from trans-3-(naphth-2-yl)-but-2-enoic acid chloride and 2-amino-5-methyl-benzoic acid in tetrahydrofuran with the addition of triethylamine.

| Yield: | 34% of theory, $C_{22}H_{19}NO_3$ (345.40) |
|---|---|
| $R_f$ value: | 0.34 (silica gel; dichloromethane/ethanol = 19:1) |
| mass spectrum: | $M^+$ = 345 |

EXAMPLE 35

Trans-3-(naphth-2-yl)-but-2-enoic acid-N-(2-carboxy-4-acetylamino-phenyl)-amide

Prepared analogously to Example 31 from trans-3-(naphth-2-yl)-but-2-enoic acid chloride and 2-amino-5-acetylamino-benzoic acid in tetrahydrofuran with the addition of triethylamine.

| Yield: | 29% of theory, $C_{23}H_{20}N_2O_4$ (388.43) |
|---|---|
| $R_f$ value: | 0.14 (silica gel; dichloromethane/ethanol = 19:1) |
| mass spectrum: | $M^+$ = 388 |

EXAMPLE 36

Trans-3-(naphth-2-yl)-but-2-enoic acid-N-(2-carboxy-4-bromo-phenyl)-amide

Prepared analogously to Example 2 from trans-3-(naphth-2-yl)-but-2-enoic acid-N-(2-methoxycarbonyl-4-bromo-phenyl)-amide and sodium hydroxide solution in methanol.

| Yield: | 10% of theory, $C_{21}H_{16}BrNO_3$ (410.28) |
|---|---|
| $R_f$ value: | 0.27 (silica gel; dichloromethane/ethanol = 19:1) |
| mass spectrum: | $M^+$ = 409/411 $(M - H)^-$ = 408/410 |

EXAMPLE 37

Trans-3-(naphth-2-yl)-but-2-enoic acid-N-(3-carboxy-pyridin-2-yl)-amide

Prepared analogously to Example 31 from trans-3-(naphth-2-yl)-but-2-enoic acid chloride and 2-aminonicotinic acid in a mixture of tetrahydrofuran and N,N'-dimethyl-imidazolidinone with the addition of triethylamine.

| Yield: | 18% of theory; $C_{20}H_{16}N_2O_3$ (332.36) |
|---|---|
| $R_f$ value: | 0.17 (silica gel; dichloromethane/ethanol = 9:1) |
| mass spectrum: | $M^+$ = 332 |

EXAMPLE 38

Trans-3-(3,4-dichlorophenyl)-pent-2-enoic acid-N-(2-carboxy-4,5-dimethoxy-phenyl)-amide Prepared analogously to Example 2 from trans-3-(3,4-dichlorophenyl)-pent-2-enoic acid-N-(4,5-dimethoxy-2-methoxycarbonyl-phenyl)-amide and sodium hydroxide solution in ethanol.

| Yield: | 12% of theory; $C_{20}H_{19}Cl_2NO_5$ (424.29) |
|---|---|
| $R_f$ value: | 0.33 (silica gel; dichloromethane/ethanol = 19.1) |
| mass spectrum: | $M^+$ = 423/425/427 |

EXAMPLE 39

Trans-3-(naphth-2-yl)-but-2-enoic acid-N-(2-carboxy-4,5-difluoro-phenyl)-amide

Prepared analogously to Example 31 from trans-3-(naphth-2-yl)-but-2-enoic acid chloride and 2-amino-4,5- difluoro-benzoic acid in tetrahydrofuran with the addition of triethylamine.

| Yield: | 11% of theory; $C_{21}H_{15}F_2NO_3$ (367.36) |
|---|---|
| $R_f$ value: | 0.24 (silica gel; dichloromethane/ethanol = 19:1) |
| mass spectrum: | $M^+ = 367$ |

EXAMPLE 40

Trans-3-(naphth-2-yl)-but-2-enoic acid-N-(2-carboxy-3-fluoro-phenyl)-amide

Prepared analogously to Example 31 from trans-3-(naphth-2-yl)-but-2-enoic acid chloride and 2-amino-6-fluoro-benzoic acid in tetrahydrofuran with the addition of triethylamine.

| Yield: | 16% of theory; $C_{21}H_{16}FNO_3$ (349.37) |
|---|---|
| $R_f$ value: | 0.23 (silica gel; ethyl acetate) |
| mass spectrum: | $M^+ = 349$ |

EXAMPLE 41

Trans-3-(6-methoxy-naphth-2-yl)-but-2-enoic acid-N-(2-carboxy-4-fluoro-phenyl)-amide Prepared analogously to Example 31 from trans-3-(6-methoxy-naphth-2-yl)-but-2-enoic acid chloride and 2-amino-5-fluoro-benzoic acid in tetrahydrofuran with the addition of triethylamine.

| Yield: | 8% of theory; $C_{22}H_{18}FNO_4$ (379.39) |
|---|---|
| $R_f$ value: | 0.25 (silica gel; dichloromethane/ethanol = 19:1) |
| mass spectrum: | $M^+ = 379$ |

EXAMPLE 42

Trans-3-(6-methoxy-naphth-2-yl)-but-2-enoic acid-N-(2-carboxy-4,5-dimethoxy-phenyl)-amide Prepared analogously to Example 2 from trans-3-(6-methoxy-naphth-2-yl)-but-2-enoic acid-N-(4,5-dimethoxy-2-methoxycarbonyl-phenyl)-amide and sodium hydroxide solution in methanol.

| Yield: | 10% of theory; $C_{24}H_{23}NO_6$ (421.46) |
|---|---|
| $R_f$ value: | 0.27 (silica gel; dichloromethane/ethanol = 19:1) |
| mass spectrum: | $M^+ = 421$ |

EXAMPLE 43

Trans-3-(benzofuran-2-yl)-but-2-enoic acid-N-(2-carboxy-4-fluoro-phenyl)-amide

Prepared analogously to Example 31 from trans-3-(benzofuran-2-yl)-but-2-enoic acid chloride and 2-amino-5-fluoro-benzoic acid in tetrahydrofuran with the addition of triethylamine.

| Yield: | 19% of theory; $C_{19}H_{14}FNO_4$ (339.33) |
|---|---|
| $R_f$ value: | 0.21 (silica gel; dichloromethane/ethanol = 19:1) |
| mass spectrum: | $M^+ = 339$ |

EXAMPLE 44

Trans-3-(benzofuran-2-yl)-but-2-enoic acid-N-(2-carboxy-4,5-dimethoxy-phenyl)-amide Prepared analogously to Example 2 from trans-3-(benzofuran-2-yl)-but-2-enoic acid-N-(4,5-dimethoxy-phenyl-2-methoxycarbonyl)-amide and sodium hydroxide solution in methanol.

| Yield: | 27% of theory, $C_{21}H_{19}NO_6$ (381.39) |
|---|---|
| $R_f$ value: | 0.29 (silica gel; dichloromethane/ethanol = 19:1) |
| mass spectrum: | $M^+ = 381$ |

EXAMPLE 45

Trans-3-(naphth-2-yl)-but-2-enoic acid-N-[2-(tetrazol-5-yl)-phenyl]-amide a) trans-3-(naphth-2-yl)-but-2-enoic acid-N-(2-cyanophenyl)-amide Prepared analogously to Example 31 from trans-3-(naphth-2-yl)-but-2-enoic acid chloride and 2-aminobenzonitrile in tetrahydrofuran with the addition of triethylamine.

| Yield: | 21% of theory, $C_{21}H_{16}N_2O$ (312.38) |
|---|---|
| $R_f$ value: | 0.49 (silica gel; petroleum ether/ethyl acetate = 4:1) | b) trans-3-(naphth-2-yl)-but-2-enoic acid-N-[2-(tetrazol-5-yl)-phenyl]-amide 312 mg (1.0 mmol) of trans-3-(naphth-2-yl)-but-2-enoic acid-N-(2-cyanophenyl)-amide are stirred together with 0.98 g (15 mmol) of sodium azide and 0.8 ammonium chloride in 20 ml of dimethylformamide for 16 hours at 120° C. After cooling, the reaction mixture is stirred into about 300 ml of water and this solution is saturated with sodium chloride. The product which crystallises out is suction filtered, washed with about 10 ml of water and dried.

| Yield: | 300 mg (84% of theory), $C_{21}H_{17}N_5O$ (355.41) |
|---|---|
| $R_f$ value: | 0.18 (silica gel; dichloromethane/ethanol = 19:1) |
| mass spectrum: | $M^+ = 355$ |

EXAMPLE 46

Trans-3-(6,7,8,9-tetrahydro-naphth-2-yl)-but-2-enoic acid-N-(2-carboxy-4-fluoro-phenyl)-amide Prepared analogously to Example 31 from trans-3-(6,7,8,9-tetrahydro-naphth-2-yl)-but-2-enoic acid chloride and 2-amino-5-fluoro-benzoic acid in tetrahydrofuran with the addition of triethylamine.

| | |
|---|---|
| Yield: | 16% of theory, $C_{21}H_{20}FNO_3$ (353.40) |
| $R_f$ value: | 0.26 (silica gel; dichloromethane/ethanol = 19:1) |
| mass spectrum: | $M^+$ = 353 |

EXAMPLE 47

Trans-2-methyl-3-(naphth-2-yl)-acrylic acid-N-(2-carboxy-4-fluoro-phenyl)-amide Prepared analogously to Example 31 from trans-2-methyl-3-(naphth-2-yl)-acrylic acid chloride and 2-amino-5-fluoro-benzoic acid in tetrahydrofuran with the addition of triethylamine.

| | |
|---|---|
| Yield: | 17% of theory, $C_{21}H_{16}FNO_3$ (349.37) |
| $R_f$ value: | 0.26 (silica gel; dichloromethane/ethanol = 19:1) |
| mass spectrum: | $M^+$ = 349 |

EXAMPLE 48

Trans-3-(3-bromophenyl)-but-2-enoic acid-N-(2-carboxy-4-fluoro-phenyl)-amide Prepared analogously to Example 31 from trans-3-(3-bromophenyl)-but-2-enoic acid chloride and 2-amino-5-fluoro-benzoic acid in tetrahydrofuran with the addition of triethylamine.

| | |
|---|---|
| Yield: | 35% of theory, $C_{17}H_{13}BrFNO_3$ (378.20) |
| $R_f$ value: | 0.20 (silica gel; dichloromethane/ethanol = 19:1) |
| mass spectrum: | $M^+$ = 377/379 |

EXAMPLE 49

Trans-3-(3,4-dimethyl-phenyl)-but-2-enoic acid-N-(2-carboxy-4-fluoro-phenyl)-amide Prepared analogously to Example 31 from trans-3-(3,4-dimethyl-phenyl)-but-2-enoic acid chloride and 2-amino-5-fluoro-benzoic acid in tetrahydrofuran with the addition of triethylamine.

| | |
|---|---|
| Yield: | 52% of theory, $C_{19}H_{18}FNO_3$ (327.36) |
| $R_f$ value: | 0.25 (silica gel; dichloromethane/ethanol = 19:1) |
| mass spectrum: | $M^+$ = 327 |

EXAMPLE 50

Trans-3-(3-pyridyl)-but-2-enoic acid-N-(2-carboxy-4-fluoro-phenyl)-amide

Prepared analogously to Example 31 from trans-3-(3-pyridyl)-but-2-enoic acid chloride and 2-amino-5-fluoro-benzoic acid in tetrahydrofuran with the addition of triethylamine.

| | |
|---|---|
| Yield: | 8% of theory, $C_{16}H_{13}FN_2O_3$ (300.29) |
| $R_f$ value: | 0.12 (silica gel; dichloromethane/ethanol = 9:1) |
| mass spectrum: | $(M - H)^-$ = 299 |

EXAMPLE 51

Trans-3-(4-bromophenyl)-but-2-enoic acid-N-(2-carboxy-4-fluoro-phenyl)-amide Prepared analogously to Example 31 from trans-3-(4-bromophenyl)-but-2-enoic acid chloride and 2-amino-5-fluoro-benzoic acid in tetrahydrofuran with the addition of triethylamine.

| | |
|---|---|
| Yield: | 35% of theory, $C_{17}H_{13}BrFNO_3$ (378.20) |
| $R_f$ value: | 0.45 (silica gel; dichloromethane/ethanol = 9:1) |
| mass spectrum: | $M^+$ = 377/379 |

EXAMPLE 52

Trans-3-(2,4-dimethyl-phenyl)-but-2-enoic acid-N-(2-carboxy-4-fluoro-phenyl)-amide Prepared analogously to Example 31 from trans-3-(2,4-dimethyl-phenyl)-but-2-enoic acid chloride and 2-amino-5-fluoro-benzoic acid in tetrahydrofuran with the addition of triethylamine.

| | |
|---|---|
| Yield: | 22% of theory, $C_{19}H_{18}FNO_3$ (327.36) |
| $R_f$ value: | 0.40 (silica gel; dichloromethane/ethanol = 9:1) |
| mass spectrum: | $M^+$ = 327 |

EXAMPLE 53

Trans-3-(naphth-1-yl)-but-2-enoic acid-N-(2-carboxy-4-fluoro-phenyl)-amide

Prepared analogously to Example 31 from trans-3-(naphth-1-yl)-but-2-enoic acid chloride and 2-amino-5-fluoro-benzoic acid in tetrahydrofuran with the addition of triethylamine.

| | |
|---|---|
| Yield: | 24% of theory, $C_{21}H_{16}FNO_3$ (349.37) |
| $R_f$ value: | 0.15 (silica gel; dichloromethane/ethanol = 19:1) |
| mass spectrum: | $M^+$ = 349 |

EXAMPLE 54

Trans-2-methyl-3-(naphth-2-yl)-acrylic acid-N-(2-carboxy-4,5-dimethoxy-phenyl)-amide Prepared analogously to Example 2 from trans-2-methyl-3-(naphth-2-yl)-acrylic acid-N-(4,5-dimethoxy-2- methoxycarbonyl-phenyl)-amide and sodium hydroxide solution in methanol.

| Yield: | 47% of theory, $C_{23}H_{21}NO_5$ (391.43) |
|---|---|
| $R_f$ value: | 0.21 (silica gel; dichloromethane/ethanol = 19:1) |
| mass spectrum: | $M^+ = 391$ |

EXAMPLE 55

Trans-3-(4-cyclohexyl-phenyl)-but-2-enoic acid-N-(2-carboxy-4-fluoro-phenyl)-amide Prepared analogously to Example 31 from trans-3-(4-cyclohexyl-phenyl)-but-2-enoic acid chloride and 2-amino-5-fluoro-benzoic acid in tetrahydrofuran with the addition of triethylamine.

| Yield: | 22% of theory, $C_{23}H_{24}FNO_3$ (381.45) |
|---|---|
| $R_f$ value: | 0.19 (silica gel; dichloromethane/ethanol = 19:1) |
| mass spectrum: | $M^+ = 381$ |

EXAMPLE 56

Trans-3-(4-cyclohexyl-phenyl)-but-2-enoic acid-N-(2-carboxy-4,5-dimethoxy-phenyl)-amide Prepared analogously to Example 2 from trans-3-(4-cyclohexyl-phenyl)-but-2-enoic acid-N-(4,5-dimethoxy-phenyl-2-methoxycarbonyl)-amide and sodium hydroxide solution in methanol.

| Yield: | 38% of theory, $C_{25}H_{29}NO_5$ (423.50) |
|---|---|
| $R_f$ value: | 0.42 (silica gel; dichloromethane/ethanol = 19:1) |
| mass spectrum: | $M^+ = 423$ |

EXAMPLE 57

Trans-3-(naphth-2-yl)-but-2-enoic acid-N-methyl-N-(2-carboxy-phenyl)-amide

Prepared analogously to Example 31 from trans-3-(naphth-2-yl)-but-2-enoic acid chloride and N-methyl-anthranilic acid in tetrahydrofuran with the addition of triethylamine.

| Yield: | 14% of theory, $C_{22}H_{19}NO_3$ (345.40) |
|---|---|
| $R_f$ value: | 0.20 (silica gel; dichloromethane/ethanol = 19:1) |
| mass spectrum: | $M^+ = 345$ |

EXAMPLE 58

Trans-3-(naphth-2-yl)-acrylic acid-N-(2-carboxy-4-fluoro-phenyl)-amide

Prepared analogously to Example 31 from trans-3-(naphth-2-yl)-acrylic acid chloride and 2-amino-5-fluoro-benzoic acid in tetrahydrofuran with the addition of triethylamine.

| Yield: | 26% of theory, $C_{20}H_{14}FNO_3$ (335.34) |
|---|---|
| $R_f$ value: | 0.18 (silica gel; dichloromethane/ethanol = 19:1) |
| mass spectrum: | $M^+ = 335$ |

EXAMPLE 59

Trans-3-(naphth-2-yl)-acrylic acid-N-(2-carboxy-4,5-dimethoxy-phenyl)-amide

Prepared analogously to Example 2 from trans-3-(naphth-2-yl)-acrylic acid-N-(4,5-dimethoxy-2-methoxycarbonyl-phenyl)-amide and sodium hydroxide solution in methanol.

| Yield: | 34% of theory, $C_{22}H_{19}NO_5$ (377.40) |
|---|---|
| $R_f$ value: | 0.23 (silica gel; dichloromethane/ethanol = 19:1) |
| mass spectrum: | $M^+ = 377$ |

EXAMPLE 60

Trans-(4-methyl-indan-1-ylidene)-acetic acid-N-(2-carboxy-4-fluoro-phenyl)-amide a) ethyl trans-(4-methyl-indan-1-yliden)-acetate 6.73 g (30 mmol) of triethyl phosphonoacetate are dissolved in 60 ml of dimethylformamide, then 3.37 g (30 mmol) of potassium-tert.butoxide is added and the mixture is stirred for 15 minutes at ambient temperature. Then 4.39 g (30 mmol) of 4-methylindane are added and stirring is continued for another two days at ambient temperature. The reaction mixture is poured onto about 200 ml of water, saturated with sodium chloride and extracted three times with ethyl acetate. The extract is washed with water, dried over sodium sulphate and evaporated down. The crude product thus obtained is purified by column chromatography over silica gel (eluant: petroleum ether with 2% ethyl acetate).

| Yield: | 1.7 g (26% of theory), $C_{14}H_{16}O_2$ (216.28) |
|---|---|
| $R_f$ value: | 0.78 (silica gel; petroleum ether/ethyl acetate = 4:1) | b) trans-(4-methyl-indan-1-ylidene)-acetic acid

Prepared analogously to Example 2 from ethyl trans-(4-methyl-indan-1-ylidene)-acetate and sodium hydroxide solution in methanol.

| Yield: | 91% of theory, $C_{12}H_{12}O_2$ (188.23) |
|---|---|
| $R_f$ value: | 0.22 (silica gel; dichloromethane/ethanol = 19:1) | c) trans-(4-methyl-indan-1-ylidene)-acetic acid chloride 941 mg (5 mmol) of trans-(4-methyl-indan-1-ylidene)-acetic acid are refluxed for 15 minutes in 10 ml of thionyl chloride after the addition of one drop of dimethylformamide. Then the mixture is evaporated to dryness and the resulting acid chloride is further reacted in crude form.

d) trans-(4-methyl-indan-1-ylidene)-acetic acid-N-(2-carboxy-4-fluoro-phenyl)-amide Prepared analogously to Example 31 from trans-(4-methyl-indan-1-ylidene)acetic acid chloride and 2-amino-5-fluoro-benzoic acid in tetrahydrofuran with the addition of triethylamine.

| Yield: | 28% of theory, $C_{19}H_{16}FNO_3$ (325.35) |
|---|---|
| $R_f$ value: | 0.24 (silica gel; dichloromethane/ethanol = 19:1) |
| mass spectrum: | $M^+ = 325$ |

EXAMPLE 61

Trans-(4-methyl-indan-1-ylidene)-acetic acid-N-(2-carboxy-4,5-dimethoxy-phenyl)-amide Prepared analogously to Example 2 from trans-(4-methyl-indan-1-ylidene)-acetic acid-N-(4,5-dimethoxy-phenyl-2-methoxycarbonyl)-amide and sodium hydroxide solution in methanol.

| Yield: | 64% of theory, $C_{21}H_{21}NO_5$ (367.41) |
|---|---|
| $R_f$ value: | 0.27 (silica gel; petroleum ether/ethyl acetate = 19:1) |
| mass spectrum: | $M^+ = 367$ |

EXAMPLE 62

Trans-3-(naphth-2-yl)-but-2-enoic acid-N-(2-carboxy-5-fluoro-phenyl)-amide

Prepared analogously to Example 31 from trans-3-(naphth-2-yl)-but-2-enoic acid chloride and 2-amino-4-fluoro-benzoic acid in tetrahydrofuran with the addition of triethylamine.

| Yield: | 11% of theory, $C_{21}H_{16}FNO_3$ (349.37) |
|---|---|
| $R_f$ value: | 0.22 (silica gel; dichloromethane/ethanol = 19:1) |
| mass spectrum: | $M^+ = 349$ |

EXAMPLE 63

Trans-3-(3,4-dimethoxy-phenyl)-but-2-enoic acid-N-(2-carboxy-4-fluoro-phenyl)-amide Prepared analogously to Example 31 from trans-3-(3,4-dimethoxy-phenyl)-but-2-enoic acid chloride and 2-amino-5-fluoro-benzoic acid in tetrahydrofuran with the addition of triethylamine.

| Yield: | 27% of theory, $C_{19}H_{18}FNO_5$ (359.36) |
|---|---|
| $R_f$ value: | 0.20 (silica gel; dichloromethane/ethanol = 19:1) |
| mass spectrum: | $M^+ = 359$ |

EXAMPLE 64

Trans-3-(4-isobutyl-phenyl)-but-2-enoic acid-N-(2-carboxy-4-fluoro-phenyl)-amide Prepared analogously to Example 31 from trans-3-(4-isobutyl-phenyl)-but-2-enoic acid chloride and 2-amino-5-fluoro-benzoic acid in tetrahydrofuran with the addition of triethylamine.

| Yield: | 38% of theory, $C_{21}H_{22}FNO_3$ (355.42) |
|---|---|
| $R_f$ value: | 0.31 (silica gel; dichloromethane/ethanol = 19:1) |
| mass spectrum: | $M^+ = 355$ |

EXAMPLE 65

Trans-3-(4-isobutyl-phenyl)-but-2-enoic acid-N-(2-carboxy-4,5-dimethoxy-phenyl)-amide Prepared analogously to Example 2 from trans-3-(4-isobutyl-phenyl)-but-2-enoic acid-N-(4,5-dimethoxy-2-methoxycarbonyl-phenyl)-amide and sodium hydroxide solution in methanol.

| Yield: | 22% of theory, $C_{23}H_{27}NO_5$ (397.48) |
|---|---|
| $R_f$ value: | 0.30 (silica gel; dichloromethane/ethanol = 19:1) |
| mass spectrum: | $M^+ = 397$ |

EXAMPLE 66

Trans-3-(benzothiophen-3-yl)-but-2-enoic acid-N-(2-carboxy-4-fluoro-phenyl)-amide Prepared analogously to Example 31 from trans-3-(benzothiophen-3-yl)-but-2-enoic acid chloride and 2-amino-5-fluoro-benzoic acid in tetrahydrofuran with the addition of triethylamine.

| Yield: | 19% of theory, $C_{19}H_{14}FNO_3S$ (355.40) |
|---|---|
| $R_f$ value: | 0.24 (silica gel; dichloromethane/ethanol = 19:1) |
| mass spectrum: | $M^+ = 355$ |

EXAMPLE 67

Trans-3-(benzothiophen-3-yl)-but-2-enoic acid-N-(2-carboxy-4,5-dimethoxy-phenyl)-amide Prepared analogously to Example 2 from trans-3-(benzothiophen-3-yl)-but-2-enoic acid-N-(4,5-dimethoxy-2-methoxycarbonyl-phenyl)-amide and sodium hydroxide solution in methanol.

| Yield: | 27% of theory, $C_{21}H_{19}NO_5S$ (397.46) |
|---|---|
| $R_f$ value: | 0.24 (silica gel; dichloromethane/ethanol = 19:1) |
| mass spectrum: | $M^+ = 397$ |

EXAMPLE 68

Trans-3-(naphth-2-yl)-but-2-enoic acid-N-(2-carboxy-4-methoxy-5-methyl-phenyl)-amide Prepared analogously to Example 2 from trans-3-(naphth-2-yl)-but-2-enoic acid-N-(2-methoxycarbonyl-4-methoxy- 5-methyl-phenyl)-amide and sodium hydroxide solution in methanol.

| | |
|---|---|
| Yield: | 40% of theory, $C_{23}H_{21}NO_4$ (375.43) |
| $R_f$ value: | 0.37 (silica gel; dichloromethane/ethanol = 9:1) |
| mass spectrum: | $M^+ = 375$ |

EXAMPLE 69

Trans-(5,7-dimethyl-3,4-dihydro-2H-naphthalin-1-ylidene)-acetic acid-N-(2-carboxy-4-fluoro-phenyl)-amide a) trans-(5,7-dimethyl-3,4-dihydro-2H-naphthalin-1-ylidene)-ethyl acetate Prepared analogously to Example 60a from triethyl phosphonoacetate and 5,7-dimethyl-1-tetralone.

| | |
|---|---|
| Yield: | 22% of theory, $C_{16}H_{20}O_2$ (244.34) |
| $R_f$ value: | 0.70 (silica gel; petroleum ether/ethyl acetate = 19:1) | b) trans-(5,7-dimethyl-3,4-dihydro-2H-naphthalin-1-ylidene)-acetic acid

Prepared analogously to Example 2 from ethyl trans-(5,7-dimethyl-3,4-dihydro-2H-naphthalin-1-ylidene)-acetate and sodium hydroxide solution in methanol.

| | |
|---|---|
| Yield: | 96% of theory, $C_{14}H_{16}O_2$ (216.28) |
| $R_f$ value: | 0.30 (silica gel; dichloromethane/ethanol = 19:1) | c) trans-(5,7-dimethyl-3,4-dihydro-2H-naphthalin-1-ylidene)-acetic acid chloride Prepared analogously to Example 60c from trans-(5,7-dimethyl-3,4-dihydro-2H-naphthalin-1-ylidene)-acetic acid and thionyl chloride.

$C_{14}H_{15}ClO$ (234.73).

d) trans-(5,7-dimethyl-3,4-dihydro-2H-naphthalin-1-ylidene)-acetic acid-N-(2-carboxy-4-fluoro-phenyl)-amide Prepared analogously to Example 31 from trans-(5,7-dimethyl-3,4-dihydro-2H-naphthalin-1-ylidene)-acetic acid chloride and 2-amino-5-fluoro-benzoic acid in tetrahydrofuran with the addition of triethylamine.

| | |
|---|---|
| Yield: | 12% of theory, $C_{21}H_{20}FNO_3$ (353.40) |
| $R_f$ value: | 0.28 (silica gel; dichloromethane/ethanol = 19:1) |
| mass spectrum: | $M^+ = 353$ |

EXAMPLE 70

Trans-3-(quinolin-2-yl)-but-2-enoic acid-N-(2-carboxy-4-fluoro-phenyl)-amide

Prepared analogously to Example 31 from trans-3-(quinolin-2-yl)-but-2-enoic acid chloride and 2-amino-5-fluoro-benzoic acid in tetrahydrofuran with the addition of triethylamine.

| | |
|---|---|
| Yield: | 13% of theory, $C_{20}H_{15}FN_2O_3$ (350.35) |
| $R_f$ value: | 0.14 (silica gel; dichloromethane/ethanol = 19:1) |
| mass spectrum: | $M^+ = 350$ <br> $(M + H)^+ = 351$ <br> $(M - H)^- = 349$ |

EXAMPLE 71

Trans-3-(naphth-2-yl)-but-2-enoic acid-N-[2-carboxy-4-(morpholin-4-yl)-phenyl]-amide Prepared analogously to Example 2 from trans-3-(naphth-2-yl)-but-2-enoic acid-N-[2-ethoxycarbonyl-4-(morpholin-4-yl)-phenyl]-amide and sodium hydroxide solution in ethanol.

| | |
|---|---|
| Yield: | 64% of theory, $C_{25}H_{24}N_2O_4$ (416.48) |
| $R_f$ value: | 0.32 (silica gel; dichloromethane/ethanol 9:1) |
| mass spectrum: | $M^+ = 416$ |

EXAMPLE 72

Trans-3-(3,4-dichloro-phenyl)-but-2-enoic acid-N-[2-carboxy-4-(morpholin-4-yl)-phenyl]-amide Prepared analogously to Example 2 from trans-3-(3,4-dichloro-phenyl)-but-2-enoic acid-N-[2-ethoxycarbonyl-4-(morpholin-4-yl)-phenyl]-amide and sodium hydroxide solution in ethanol.

| | |
|---|---|
| Yield: | 73% of theory, $C_{21}H_{20}Cl_2N_2O_4$ (435.31) |
| $R_f$ value: | 0.46 (silica gel; dichloromethane/ethanol = 9:1) |
| mass spectrum: | $M^+ = 434/436$ <br> $(M + H)^+ = 435/437$ <br> $(M - H)^- = 433/435$ |

EXAMPLE 73

Trans-3-(6-methyl-naphth-2-yl)-but-2-enoic acid-N-(2-carboxy-phenyl)-amide

Prepared analogously to Example 31 from trans-3-(6-methyl-naphth-2-yl)-but-2-enoic acid chloride and anthranilic acid in tetrahydrofuran with the addition of triethylamine.

| | |
|---|---|
| Yield: | 23% of theory, $C_{22}H_{19}NO_3$ (345.40) |
| $R_f$ value: | 0.18 (silica gel; dichloromethane/ethanol = 19:1) |
| mass spectrum: | $M^+ = 345$ <br> $(M + H)^+ = 346$ <br> $(M - H)^- = 344$ |

EXAMPLE 74

Trans-3-(6-methyl-naphth-2-yl)-but-2-enoic acid-N-(2-carboxy-4-fluoro-phenyl)-amide Prepared analogously to Example 31 from trans-3-(6-methyl-naphth-2-yl)-but-2-enoic acid chloride and 2-amino- 5-fluoro-benzoic acid in tetrahydrofuran with the addition of triethylamine.

| Yield: | 18% of theory, $C_{22}H_{18}FNO_3$ (363.39) |
|---|---|
| $R_f$ value: | 0.20 (silica gel; dichloromethane/ethanol = 19:1) |
| mass spectrum: | $M^+ = 363$ |

EXAMPLE 75

Trans-3-(6-methyl-naphth-2-yl)-but-2-enoic acid-N-(2-carboxy-5-fluoro-phenyl)-amide Prepared analogously to Example 31 from trans-3-(6-methyl-naphth-2-yl)-but-2-enoic acid chloride and 2-amino-4-fluoro-benzoic acid in tetrahydrofuran with the addition of triethylamine.

| Yield: | 32% of theory, $C_{22}H_{18}FNO_3$ (363.39) |
|---|---|
| $R_f$ value: | 0.22 (silica gel; dichloromethane/ethanol = 19:1) |
| mass spectrum: | $M^+ = 363$ |

EXAMPLE 76

Trans-3-(6-methyl-naphth-2-yl)-but-2-enoic acid-N-(2-carboxy-4,5-dimethoxy-phenyl)-amide Prepared analogously to Example 2 from trans-3-(6-methyl-naphth-2-yl)-but-2-enoic acid-N-(4,5-dimethoxy-methoxycarbonyl-phenyl)-amide and sodium hydroxide solution in methanol.

| Yield: | 67% of theory, $C_{24}H_{23}NO_5$ (405.45) |
|---|---|
| $R_f$ value: | 0.21 (silica gel; dichloromethane/ethanol = 19:1) |
| mass spectrum: | $M^+ = 405$ |
| | $(M + Na)^+ = 428$ |
| | $(M - H)^- = 404$ |

EXAMPLE 77

Trans-3-(3,4-dichloro-phenyl)-but-2-enoic acid-N-(2-carboxy-4-dimethylamino-phenyl)-amide Prepared analogously to Example 2 from trans-3-(3,4-dichloro-phenyl)-but-2-enoic acid-N-(2-ethoxycarbonyl-4-dimethylamino-phenyl)-amide and sodium hydroxide solution in ethanol.

| Yield: | 47% of theory, $C_{19}H_{18}Cl_2N_2O_3$ (393.27) |
|---|---|
| $R_f$ value: | 0.55 (silica gel; dichloromethane/ethanol = 9:1) |
| mass spectrum: | $M^+ = 392/394$ |
| | $(M + H)^+ = 393/395$ |
| | $(M - H)^- = 391/393$ |

EXAMPLE 78

Trans-3-(naphth-2-yl)-but-2-enoic acid-N-(2-carboxy-4-dimethylamino-phenyl)-amide Prepared analogously to Example 2 from trans-3-(naphth-2-yl)-but-2-enoic aid-N-(2-ethoxycarbonyl-4-dimethylamino-phenyl)-amide and sodium hydroxide solution in ethanol.

| Yield: | 84% of theory, $C_{23}H_{22}N_2O_3$ (374.44) |
|---|---|
| $R_f$ value: | 0.59 (silica gel; dichloromethane/ethanol = 9:1) |
| mass spectrum: | $M^+ = 374$ |
| | $(M - H)^- = 373$ |

EXAMPLE 79

Trans-3-(naphth-2-yl)-but-2-enoic acid-N-(n-pentyl)-N-(3-carboxy-4-amino-phenyl)-amide Prepared analogously to Example 2 from trans-3-(naphth-2-yl)-but-2-enoic acid-N-(n-pentyl)-N-(3-ethoxycarbonyl-4-amino-phenyl)-amide and sodium hydroxide solution in ethanol.

| Yield: | 65% of theory, $C_{26}H_{28}N_2O_3$ (416.52) |
|---|---|
| $R_f$ value: | 0.51 (silica gel; dichloromethane/ethanol = 9:1) |
| mass spectrum: | $M^+ = 416$ |
| | $(M + H)^+ = 417$ |
| | $(M - H)^- = 415$ |

EXAMPLE 80

Trans-3-(2,4-dichlorophenyl)-but-2-enoic acid-N-(2-carboxy-4-fluoro-phenyl)-amide Prepared analogously to Example 31 from trans-3-(2,4-dichlorophen-yl)-but-2-enoic acid chloride and 2-amino-5-fluoro-benzoic acid in tetrahydrofuran with the addition of triethylamine.

| Yield: | 16% of theory, $C_{17}H_{12}Cl_2FNO_3$ (368.19) |
|---|---|
| $R_f$ value: | 0.21 (silica gel; dichloromethane/ethanol = 19:1) |
| mass spectrum: | $M^+ = 367/369/371$ |

EXAMPLE 81

Trans-3-(2,4-dichlorophenyl)-but-2-enoic acid-N-(2-carboxy-4,5-dimethoxy-phenyl)-amide Prepared analogously to Example 2 from trans-3-(2,4-dichlorophenyl)-but-2-enoic acid-N-(2-methoxycarbonyl-4,5-dimethoxy-phenyl)-amide and sodium hydroxide solution in methanol.

| Yield: | 97% of theory, $C_{19}H_{17}Cl_2NO_5$ (410.26) |
|---|---|
| $R_f$ value: | 0.25 (silica gel; dichloromethane/ethanol = 19:1) |
| mass spectrum: | $M^+ = 409/411/413$ |

EXAMPLE 82

Trans-2-methyl-3-(naphth-2-yl)-but-2-enoic acid-N-(2-carboxy-4-fluoro-phenyl)-amide Prepared analogously to Example 31 from trans-2-methyl-3-(naphth-2-yl)-but-2-enoic acid chloride and 2-amino-5-fluoro-benzoic acid in tetrahydrofuran with the addition of triethylamine.

| | |
|---|---|
| Yield: | 12% of theory, $C_{22}H_{18}FNO_3$ (363.39) |
| $R_f$ value: | 0.21 (silica gel; dichloromethane/ethanol = 19:1) |
| mass spectrum: | $M^+ = 363$ |
| | $(M - H)^- = 362$ |

EXAMPLE 83 cis-2-fluoro-3-(naphth-2-yl)-but-2-enoic acid-N-(2-carboxy-4-fluoro-phenyl)-amide Prepared analogously to Example 31 from cis-2-fluoro-3-(naphth-2-yl)-but-2-enoic acid chloride and 2-amino-5-fluoro-benzoic acid in tetrahydrofuran with the addition of triethylamine.

| | |
|---|---|
| Yield: | 9% of theory, $C_{21}H_{15}F_2NO_3$ (367.36) |
| $R_f$ value: | 0.18 (silica gel; dichloromethane/ethanol = 19:1) |
| mass spectrum: | $M^+ = 367$ |
| | $(M + H)^+ = 368$ |
| | $(M - H)^- = 366$ |

EXAMPLE 84

Trans-2-methyl-3-(naphth-2-yl)-but-2-enoic acid-N-(2-carboxy-4,5-dimethoxy-phenyl)-amide Prepared analogously to Example 2 from trans-2-methyl-3-(naphth-2-yl)-but-2-enoic acid-N-(2-methoxycarbonyl-4,5-dimethoxy-phenyl)-amide and sodium hydroxide solution in ethanol.

| | |
|---|---|
| Yield: | 48% of theory, $C_{24}H_{23}NO_5$ (405.45) |
| $R_f$ value: | 0.32 (silica gel; dichloromethane/ethanol = 19:1) |
| mass spectrum: | $(M + H)^+ = 406$ |
| | $(M + Na)^+ = 428$ |
| | $(M - H)^- = 404$ |

EXAMPLE 85

Trans-2-methoxy-3-(naphth-2-yl)-acrylic acid-N-(2-carboxy-4-fluoro-phenyl)-amide Prepared analogously to Example 31 from trans-2-methoxy-3-(naphth-2-yl)-acrylic acid chloride and 2-amino-5-fluoro-benzoic acid in tetrahydrofuran with the addition of triethylamine.

| | |
|---|---|
| Yield: | 29% of theory, $C_{21}H_{16}FNO_4$ (365.36) |
| $R_f$ value: | 0.19 (silica gel; dichloromethane/ethanol = 1 |
| mass spectrum: | $M^+ = 365$ |
| | $M - H)^- = 364$ |

EXAMPLE 86

Trans-2-methoxy-3-(naphth-2-yl)-acrylic acid-N-(2-carboxy-4,5-dimethoxy-phenyl)-amide Prepared analogously to Example 2 from trans-2-methoxy-3-(naphth-2-yl)-acrylic acid-N-(2-methoxycarbonyl-4,5-dimethoxy-phenyl)-amide and sodium hydroxide solution in methanol.

| | |
|---|---|
| Yield: | 75% of theory, $C_{22}H_{21}NO_6$ (407.43) |
| $R_f$ value: | 0.46 (silica gel; dichloromethane/ethanol = 19:1) |
| mass spectrum: | $M^+ = 407$ |
| | $(M - H)^- = 406$ |

EXAMPLE 87

Trans-3-(naphth-2-yl)-but-2-enoic acid-N-(cis-2-carboxy-cyclohexyl)-amide

Prepared analogously to Example 2 from trans-3-(naphth-2-yl)-but-2-enoic acid-N-(cis-2-ethoxycarbonyl-cyclohexyl)-amide and sodium hydroxide solution in methanol.

| | |
|---|---|
| Yield: | 96% of theory, $C_{21}H_{23}NO_3$ (337.42) |
| $R_f$ value: | 0.31 (silica gel; dichloromethane/ethanol = 9:1) |
| mass spectrum: | $M^+ = 337$ |
| | $(M + Na)^+ = 360$ |
| | $(M - H)^- = 336$ |

EXAMPLE 88

Trans-3-(naphth-2-yl)-but-2-enoic acid-N-[2-carboxy-4-(N'-methyl-N'-benzyl-amino)-phenyl]-amide Prepared analogously to Example 2 from trans-3-(naphth-2-yl)-but-2-enoic acid-N-[2-ethoxycarbonyl-4-(N'-methyl-N'-benzyl-amino)-phenyl]-amide and sodium hydroxide solution in ethanol.

| | |
|---|---|
| Yield: | 74% of theory, $C_{29}H_{26}N_2O_3$ (450.54) |
| $R_f$ value: | 0.32 (silica gel; dichloromethane/ethanol = 19:1) |
| mass spectrum: | $M^+ = 450$ |
| | $(M - H)^- = 449$ |

EXAMPLE 89

Trans-3-(naphth-2-yl)-but-2-enoic acid-N-{2-carboxy-4-[N-methyl-N-(2-(N',N'-dimethylamino)-ethyl)-amino]-phenyl}-amide Prepared analogously to Example 2 from trans-3-(naphth-2-yl)-but-2-enoic acid-N-{2-ethoxycarbonyl-4-[N-methyl-N-(2-(N',N'-dimethylamino)-ethyl)-amino]-phenyl}-amide and sodium hydroxide solution in ethanol.

| | |
|---|---|
| Yield: | 69% of theory, $C_{26}H_{29}N_3O_3$ (431.54) |
| $R_f$ value: | 0.13 (silica gel; dichloromethane/ethanol = 4:1) |

-continued

| | |
|---|---|
| mass spectrum: | M$^+$ = 431 |
| | (M + H)$^+$ = 432 |
| | (M + Na)$^+$ = 454 |
| | (M − H)$^-$ = 430 |

EXAMPLE 90

Trans-3-(naphth-2-yl)-but-2-enoic acid-N-[2-carboxy-4-(N'-methyl-N'-(2-phenylethyl)-amino)-phenyl]-amide Prepared analogously to Example 2 from trans-3-(naphth-2-yl)-but-2-enoic acid-N-[2-ethoxycarbonyl-4-(N'-methyl-N'-(2-phenylethyl)-amino)-phenyl]-amide and sodium hydroxide solution in ethanol.

| | |
|---|---|
| Yield: | 49% of theory, |
| | C$_{30}$H$_{28}$N$_2$O$_3$ (464.57) |
| R$_f$ value: | 0.31 (silica gel; dichloromethane/ethanol = 19:1) |
| mass spectrum: | M$^+$ = 464 |
| | (M − H)$^-$ = 463 |

EXAMPLE 91

Trans-3-(naphth-2-yl)-but-2-enoic acid-N-[2-carboxy-4-(N'-methyl-N'-n-heptyl-amino)-phenyl]-amide Prepared analogously to Example 2 from trans-3-(naphth-2-yl)-but-2-enoic acid-N-[2-ethoxycarbonyl-4-(N'-methyl-N'-n-heptyl-amino)-phenyl]-amide and sodium hydroxide solution in ethanol.

| | |
|---|---|
| Yield: | 39% of theory, |
| | C$_{29}$H$_{34}$N$_2$O$_3$ (458.61) |
| R$_f$ value: | 0.39 (silica gel; dichloromethane/ethanol = 19:1) |
| mass spectrum: | M$^+$ = 458 |
| | (M + H)$^+$ = 459 |
| | (M + Na)$^+$ = 481 |
| | (M − H)$^-$ = 457 |

EXAMPLE 92

Trans-3-(naphth-2-yl)-but-2-enoic acid-N-[2-carboxy-4-(N'-methyl-N'-(3-pyridylmethyl)-amino)-phenyl]-amide Prepared analogously to Example 2 from trans-3-(naphth-2-yl)-but-2-enoic acid-N-[2-ethoxycarbonyl-4-(N'-methyl-N'-(3-pyridylmethyl-amino)-phenyl]-amide and sodium hydroxide solution in ethanol.

| | |
|---|---|
| Yield: | 41% of theory, |
| | C$_{28}$H$_{25}$N$_3$O$_3$ (451.53) |
| R$_f$ value: | 0.58 (silica gel; dichloromethane/ethanol = 9:1) |
| mass spectrum: | M$^+$ = 451 |
| | (M + H)$^+$ = 452 |
| | (M − H)$^-$ = 450 |

EXAMPLE 93

Trans-3-(naphth-2-yl)-but-2-enoic acid-N-[2-carboxy-4-(N'-methyl-N'-(2-(pyrid-2-yl)-ethyl)-amino)-phenyl]-amide Prepared analogously to Example 2 from trans-3-(naphth-2-yl)-but-2-enoic acid-N-[2-ethoxycarbonyl-4-(N'-methyl-N'-(2-(pyrid-2-yl)-ethyl)-amino)-phenyl]-amide and sodium hydroxide solution in ethanol.

| | |
|---|---|
| Yield: | 75% of theory, |
| | C$_{29}$H$_{27}$N$_3$O$_3$ (465.56) |
| R$_f$ value: | 0.52 (silica gel; dichloromethane/ethanol = 9:1) |
| mass spectrum: | M$^+$ = 465 |
| | (M + H)$^+$ = 466 |
| | (M − H)$^-$ = 464 |

EXAMPLE 94

Trans-3-(naphth-2-yl)-but-2-enoic acid-N-[2-carboxy-4-(N-methyl-N-(3-(N',N'-dimethylamino)-propyl)-amino)-phenyl]-amide Prepared analogously to Example 2 from trans-3-(naphth-2-yl)-but-2-enoic acid-N-[2-ethoxycarbonyl-4-(N-methyl-N-(3-(N',N'-dimethylamino)-propyl)-amino)-phenyl]-amide and sodium hydroxide solution in ethanol.

| | |
|---|---|
| Yield: | 56% of theory, |
| | C$_{27}$H$_{31}$N$_3$O$_3$ (445.57) |
| R$_f$ value: | 0.11 (silica gel; dichloromethane/ethanol = 9:1) |
| mass spectrum: | M$^+$ = 445 |
| | (M + H)$^+$ = 446 |
| | (M + Na)$^+$ = 468 |

EXAMPLE 95

Trans-3-(naphth-2-yl)-but-2-enoic acid-N-(2-carboxy-5-nitro-phenyl)-amide

Prepared analogously to Example 2 from trans-3-(naphth-2-yl)-but-2-enoic acid-N-(2-methoxycarbonyl-5-nitro-phenyl)-amide and sodium hydroxide solution in ethanol.

| | |
|---|---|
| Yield: | 48% of theory, |
| | C$_{21}$H$_{16}$N$_2$O$_5$ (376.37) |
| R$_f$ value: | 0.19 (silica gel; dichloromethane/ethanol = 19:1) |
| mass spectrum: | M$^+$ = 376 |
| | (M − H)$^-$ = 375 |

EXAMPLE 96

Trans-3-(naphth-2-yl)-but-2-enoic acid-N-(2-carboxy-5-methanesulphonylamino-phenyl)-amide Prepared analogously to Example 2 from trans-3-(naphth-2-yl)-but-2-enoic acid-N-(2-methoxycarbonyl-5-methanesulphonylamino-phenyl)-amide and sodium hydroxide solution in methanol.

| | |
|---|---|
| Yield: | 87% of theory, $C_{22}H_{20}N_2O_5S$ (424.48) |
| $R_f$ value: | 0.22 (silica gel; dichloromethane/ethanol = 19:1) |
| mass spectrum: | $M^+$ = 424 |
| | $(M - H)^-$ = 423 |

EXAMPLE 97

5-phenyl-penta-2,4-dienoic acid-N-(2-carboxy-4-fluoro-phenyl)-amide

Prepared analogously to Example 31 from 5-phenyl-penta-2,4-dienoic acid chloride and 2-amino-5-fluoro-benzoic acid in tetrahydrofuran with the addition of triethylamine.

| | |
|---|---|
| Yield: | 27% of theory, $C_{18}H_{14}FNO_3$ (311.32) |
| $R_f$ value: | 0.24 (silica gel; dichloromethane/ethanol = 19:1) |
| mass spectrum: | $M^+$ = 311 |
| | $(M - H)^-$ = 310 |

EXAMPLE 98

Trans-3-(3,4-dichloro-phenyl)-but-2-enoic acid-N-(2-carboxy-4-fluoro-phenyl)-amide Prepared analogously to Example 31 from trans-3-(3,4-dichloro-phenyl)-but-2-enoic acid chloride and 2-amino-5-fluoro-benzoic acid in tetrahydrofuran with the addition of triethylamine.

| | |
|---|---|
| Yield: | 16% of theory, $C_{17}H_{12}Cl_2FNO_3$ (368.19) |
| $R_f$ value: | 0.21 (silica gel; dichloromethane/ethanol = 19:1) |
| mass spectrum: | $(M - H)^-$ = 366/368/370 |

EXAMPLE 99

Trans-3-(naphth-2-yl)-but-2-enoic acid-N-[2-carboxy-4-(N'-methyl-N'-(2-methoxyethyl)-amino)-phenyl]-amide Prepared analogously to Example 2 from trans-3-(naphth-2-yl)-but-2-enoic acid-N-[2-ethoxycarbonyl-4-(N'-methyl-N'-(2-methoxyethyl)-amino)-phenyl]-amide and sodium hydroxide solution in ethanol.

| | |
|---|---|
| Yield: | 80% of theory, $C_{25}H_{26}N_2O_4$ (418.50) |
| $R_f$ value: | 0.51 (silica gel; dichloromethane/ethanol = 9:1) |
| mass spectrum: | $M^+$ = 418 |
| | $(M + H)^+$ = 419 |
| | $(M + Na)^+$ = 441 |
| | $(M - H)^-$ = 417 |

EXAMPLE 100

Trans-3-(naphth-2-yl)-but-2-enoic acid-N-(2-carboxy-5-benzenesulphonylamino-phenyl)-amide Prepared analogously to Example 2 from trans-3-(naphth-2-yl)-but-2-enoic acid-N-(2-methoxycarbonyl-5-benzenesulphonylamino-phenyl)-amide and sodium hydroxide solution in methanol.

| | |
|---|---|
| Yield: | 92% of theory, $C_{27}H_{22}N_2O_5S$ (486.55) |
| $R_f$ value: | 0.31 (silica gel; dichloromethane/ethanol = 19:1) |
| mass spectrum: | $M^+$ = 486 |
| | $(M - H)^-$ = 485 |

EXAMPLE 101

Trans-3-(naphth-2-yl)-but-2-enoic acid-N-(2-carboxy-5-aminosulphonyl-phenyl)-amide Prepared analogously to Example 2 from trans-3-(naphth-2-yl)-but-2-enoic acid-N-(2-methoxycarbonyl-5-aminosulphonyl-phenyl)-amide and sodium hydroxide solution in methanol.

| | |
|---|---|
| Yield: | 15% of theory, $C_{21}H_{18}N_2O_5S$ (410.45) |
| $R_f$ value: | 0.11 (silica gel; ethyl acetate/petroleum ether = 1:1) |
| mass spectrum: | $M^+$ = 410 |
| | $(M - H)^-$ = 409 |

EXAMPLE 102

3-(naphth-2-yl)-butanoic acid-N-(2-carboxy-5-acetylamino-phenyl)-amide

Prepared analogously to Example 2 from 3-(naphth-2-yl)-butanoic acid-N-(2-methoxycarbonyl-5-acetylamino-phenyl)-amide and sodium hydroxide solution in methanol.

| | |
|---|---|
| Yield: | 46% of theory, $C_{23}H_{22}N_2O_4$ (390.44) |
| $R_f$ value: | 0.20 (silica gel; dichloromethane/ethanol = 50:1) |
| mass spectrum: | $M^+$ = 390 |
| | $(M + Na)^+$ = 413 |
| | $(M - H)^-$ = 389 |

EXAMPLE 103

3-(naphth-2-yl)-butanoic acid-N-(2-carboxy-5-benzoylamino-phenyl)-amide

Prepared analogously to Example 2 from 3-(naphth-2-yl)-butanoic acid-N-(2-methoxycarbonyl-5-benzoylamino-phenyl)-amide and sodium hydroxide solution in methanol.

| | |
|---|---|
| Yield: | 96% of theory, $C_{28}H_{24}N_2O_4$ (452.51) |
| $R_f$ value: | 0.24 (silica gel; dichloromethane/ethanol = 19:1) |
| mass spectrum: | $M^+$ = 452 |
| | $(M + Na)^+$ = 475 |
| | $(M - H)^-$ = 451 |

EXAMPLE 104

Trans-3-(quinolin-3-yl)-but-2-enoic acid-N-(2-carboxy-4-fluoro-phenyl)-amide

Prepared analogously to Example 31 from trans-3-(quinolin-3-yl)-but-2-enoic acid chloride and 2-amino-5- fluorobenzoic acid in tetrahydrofuran with the addition of triethylamine.

| | |
|---|---|
| Yield: | 19% of theory, $C_{20}H_{15}FN_2O_3$ (350.35) |
| $R_f$ value: | 0.22 (silica gel; dichloromethane/ethanol = 19:1) |
| mass spectrum: | $(M + Na)^+ = 373$ $(M - H)^- = 349$ |

EXAMPLE 105

Trans-3-(naphth-2-yl)-but-2-enoic acid-N-(2,5-dicarboxy-phenyl)-amide

Prepared analogously to Example 2 from trans-3-(naphth-2-yl)-but-2-enoic acid-N-(2,5-dimethoxycarbonyl-phenyl)-amide and sodium hydroxide solution in ethanol.

| | |
|---|---|
| Yield: | 88% of theory, $C_{22}H_{17}NO_5$ (375.38) |
| $R_f$ value: | 0.11 (silica gel; dichloromethane/ethanol = 9:1) |
| mass spectrum: | $M^+ = 375$ $(M - H)^- = 374$ |

EXAMPLE 106

Trans-3-(1-methoxy-naphth-2-yl)-but-2-enoic acid-N-(2-carboxy-phenyl)-amide

Prepared analogously to Example 2 from trans-3-(1-methoxy-naphth-2-yl)-but-2-enoic acid-N-(2-methoxycarbonyl-phenyl)-amide and sodium hydroxide solution in ethanol.

| | |
|---|---|
| Yield: | 96% of theory, $C_{22}H_{19}NO_4$ (361.40) |
| $R_f$ value: | 0.56 (silica gel; dichloromethane/ethanol = 9:1) |
| mass spectrum: | $M^+ = 361$ $(M + Na)^+ = 384$ $(M - H)^- = 360$ |

EXAMPLE 107

Trans-3-(naphth-2-yl)-but-2-enoic acid-N-(2-carboxy-thiophen-3-yl)-amide

Prepared analogously to Example 2 from trans-3-(naphth-2-yl)-but-2-enoic acid-N-(2-methoxycarbonyl-thiophen-3-yl)-amide and sodium hydroxide solution in ethanol.

| | |
|---|---|
| Yield: | 93% of theory, $C_{19}H_{15}NO_3S$ (337.40) |
| $R_f$ value: | 0.53 (silica gel; dichloromethane/ethanol = 9:1) |
| mass spectrum: | $M^+ = 337$ $(M + Na)^+ = 360$ $(M - H)^- = 336$ |

EXAMPLE 108

Trans-3-(naphth-2-yl)-but-2-enoic acid-N-[2-carboxy-4-(N'-methyl-N'-(2-cyanoethyl)-amino)-phenyl]-amide Prepared analogously to Example 31 from trans-3-(naphth-2-yl)-but-2-enoic acid chloride and 2-amino-5-(N-methyl-N-(2-cyanoethyl)-amino)-benzoic acid in tetrahydrofuran with the addition of triethylamine.

| | |
|---|---|
| Yield: | 16% of theory, $C_{25}H_{23}N_3O_3$ (413.48) |
| $R_f$ value: | 0.50 (silica gel; dichloromethane/ethanol = 9:1) |
| mass spectrum: | $M^+ = 413$ $(M + Na)^+ = 436$ $(M - H)^- = 412$ |

EXAMPLE 109

Trans-3-(naphth-2-yl)-but-2-enoic acid-N-(2-carboxy-4-hydroxy-phenyl)-amide

Prepared analogously to Example 31 from trans-3-(naphth-2-yl)-but-2-enoic acid chloride and 5-hydroxy-anthranilic acid in tetrahydrofuran with the addition of triethylamine.

| | |
|---|---|
| Yield: | 34% of theory, $C_{21}H_{17}NO_4$ (347.37) |
| $R_f$ value: | 0.19 (silica gel; dichloromethane/ethanol = 19:1) |
| mass spectrum: | $M^+ = 347$ $(M + Na)^+ = 370$ $(M - H)^-\ 346$ |

EXAMPLE 110

Trans-3-(naphth-2-yl)-but-2-enoic acid-N-(2-sulpho-phenyl)-amide

Prepared analogously to Example 31 from trans-3-(naphth-2-yl)-but-2-enoic acid chloride and 2-amino-benzenesulphonic acid in tetrahydrofuran with the addition of triethylamine.

| | |
|---|---|
| Yield: | 43% of theory, $C_{20}H_{17}NO_4S$ (367.43) |
| $R_f$ value: | 0.28 (silica gel; dichloromethane/ethanol = 19:1) |
| mass spectrum: | $M^+ = 367$ $(M - H)^- = 366$ |

EXAMPLE 111

Trans-3-(naphth-2-yl)-but-2-enoic acid-N-(3-carboxy-thiophen-4-yl)-amide

Prepared analogously to Example 2 from trans-3-(naphth-2-yl)-but-2-enoic acid-N-(3-methoxycarbonyl-thiophen-4-yl)-amide and sodium hydroxide solution in ethanol.

| | |
|---|---|
| Yield: | 88% of theory, $C_{19}H_{15}NO_3S$ (337.40) |
| $R_f$ value: | 0.41 (silica gel; dichloromethane/ethanol = 19:1) |
| mass spectrum: | $M^+ = 337$ $(M + Na)^+ = 360$ $(M - H)^- = 336$ |

EXAMPLE 112

Trans-3-(naphth-2-yl)-but-2-enoic acid-N-[2-carboxy-4-(N'-methyl-N'-(4-cyanobutyl)-amino)-phenyl]-amide Prepared analogously to Example 2 from trans-3-(naphth-2-yl)-but-2-enoic acid-N-[2-ethoxycarbonyl-4-(N'-methyl- N'-(4-cyanobutyl)-amino)-phenyl]-amide and sodium hydroxide solution in ethanol.

| | |
|---|---|
| Yield: | 90% of theory, $C_{27}H_{27}N_3O_3$ (441.54) |
| $R_f$ value: | 0.68 (silica gel; dichloromethane/ethanol = 9:1) |
| mass spectrum: | $M^+ = 441$ |
| | $(M - H)^- = 440$ |

EXAMPLE 113

Trans-3-(naphth-2-yl)-but-2-enoic acid-N-(2-carboxy-5-amino-phenyl)-amide

Prepared analogously to Example 2 from trans-3-(naphth-2-yl)-but-2-enoic acid-N-(2-methoxycarbonyl-5-amino-phenyl)-amide and sodium hydroxide solution in methanol.

| | |
|---|---|
| Yield: | 76% of theory, $C_{21}H_{18}N_2O_3$ (346.39) |
| $R_f$ value: | 0.37 (silica gel; dichloromethane/ethanol = 19:1) |
| mass spectrum: | $M^+ = 346$ |
| | $(M - H)^- = 345$ |

EXAMPLE 114

Trans-3-(naphth-2-yl)-but-2-enoic acid-N-[2-carboxy-4-(N'-methyl-N'-(4-(tetrazol-5-yl)-butyl)-amino)-phenyl]-amide a) trans-3-(naphth-2-yl)-but-2-enoic acid-N-[2-ethoxycarbonyl-4-(N'-methyl-N'-(4-(tetrazol-5-yl)-butyl)-amino)-phenyl]-amide A solution of 3.90 g (8.3 mmol) of trans-3-(naphth-2-yl)-but-2-enoic acid-N-[2-ethoxycarbonyl-4-(N'-methyl-N'-(4-cyanobutyl)-amino)-phenyl]-amide, 9.75 g (150 mmol) of sodium azide and 8.02 g (150 mmol) of ammonium chloride in 70 ml of dimethylformamide is stirred for six hours at 130° C. After cooling, the reaction mixture is diluted with about 150 ml of water, then extracted with ethyl acetate. The crude product obtained from the extract is purified by column chromatography over silica gel (eluant: dichloromethane with 1 to 5% ethanol).

| | |
|---|---|
| Yield: | 2.30 g (54% of theory), $C_{29}H_{32}N_6O_3$ (512.62) |
| $R_f$ value: | 0.48 (silica gel; dichloromethane/ethanol = 9:1) |
| mass spectrum: | $M^+ = 512$ |
| | $(M - H)^- = 511$ | b) trans-3-(naphth-2-yl)-but-2-enoic acid-N-[2-carboxy-4-(N'-methyl-N'-(4-(tetrazol-5-yl)-butyl)-amino)-phenyl]-amide Prepared analogously to Example 2 from trans-3-(naphth-2-yl)-but-2-enoic acid-N-[2-ethoxycarbonyl-4-(N'-methyl-N'-(4-(tetrazol-5-yl)-butyl)-amino)-phenyl]-amide and sodium hydroxide solution in ethanol.

| | |
|---|---|
| Yield: | 87% of theory, $C_{27}H_{28}N_6O_3$ (484.56) |
| $R_f$ value: | 0.22 (silica gel; dichloromethane/ethanol = 9:1) |
| mass spectrum: | $(M - H)^- = 483$ |

EXAMPLE 115

Trans-3-(1-bromo-naphth-2-yl)-acrylic acid-N-(2-carboxy-phenyl)-amide

Prepared analogously to Example 2 from trans-3-(1-bromo-naphth-2-yl)-acrylic acid-N-(2-methoxycarbonyl-phenyl)-amide and sodium hydroxide solution in methanol.

| | |
|---|---|
| Yield: | 87% of theory, $C_{20}H_{14}BrNO_3$ (396.24) |
| $R_f$ value: | 0.18 (silica gel; dichloromethane/ethanol = 50:1) |
| mass spectrum: | $M^+ = 395/397$ |
| | $(M - H)^- = 394/396$ |

EXAMPLE 116

Trans-3-(3,4-difluorophenyl)-but-2-enoic acid-N-(2-carboxy-phenyl)-amide

Prepared analogously to Example 2 from trans-3-(3,4-difluorophenyl)-but-2-enoic acid-N-(2-methoxycarbonyl-phenyl)-amide and sodium hydroxide solution in methanol.

| | |
|---|---|
| Yield: | 54% of theory, $C_{17}H_{13}F_2NO_3$ (317.30) |
| $R_f$ value: | 0.41 (silica gel; dichloromethane/ethanol = 9:1) |
| mass spectrum: | $M^+ = 317$ |
| | $(M - H)^- = 316$ |

EXAMPLE 117

Trans-3-(naphth-2-yl)-but-2-enoic acid-N-[2-carboxy-4-(2-ethyl-4-methyl-imidazol-1-yl)-phenyl]-amide Prepared analogously to Example 2 from trans-3-(naphth-2-yl)-but-2-enoic acid-N-[2-methoxycarbonyl-4-(2-ethyl-4-methyl-imidazol-1-yl)-phenyl]-amide and sodium hydroxide solution in methanol.

| | |
|---|---|
| Yield: | 89% of theory, $C_{27}H_{25}N_3O_3$ (439.52) |
| $R_f$ value: | 0.13 (silica gel; dichloromethane/ethanol = 9:1) |
| mass spectrum: | $M^+ = 439$ |
| | $(M - H)^- = 438$ |

EXAMPLE 118

Trans-3-(naphth-2-yl)-but-2-enoic acid-N-[2-carboxy-4-(imidazol-1-yl)-phenyl]-amide Prepared analogously to Example 2 from trans-3-(naphth-2-yl)-but-2-enoic acid-N-[2-methoxycarbonyl-4-(imidazol-1-yl)-phenyl]-amide and sodium hydroxide solution in methanol.

| | |
|---|---|
| Yield: | 69% of theory, $C_{24}H_{19}N_3O_3$ (397.44) |
| $R_f$ value: | 0.12 (silica gel; dichloromethane/ethanol = 9:1) |
| mass spectrum: | $M^+$ = 397 |
| | $(M + H)^+$ = 398 |
| | $(M - H)^-$ = 396 |

EXAMPLE 119

Trans-3-(naphth-2-yl)-but-2-enoic acid-N-[2-carboxy-4-(3,5-dimethyl-pyrazol-1-yl)-phenyl]-amide a) methyl 2-nitro-5-(3,5-dimethyl-pyrazol-1-yl)-benzoate A solution of 2.84 g (10 mmol) of 3-methoxycarbonyl-4-nitro-phenylhydrazine, 1.0 g (10 mmol) of acetylacetone and 3.0 ml of triethylamine in 40 ml of methanol is stirred overnight at ambient temperature. Then it is evaporated to dryness, the residue is dissolved in about 50 ml of dichloromethane, the solution is washed with 5% sodium hydrogen carbonate solution, dried and evaporated down again. The crude product thus obtained is purified by column chromatography over silica gel (eluant: dichloromethane).

| | |
|---|---|
| Yield: | 1.50 g (55% of theory), $C_{13}H_{13}N_3O_4$ (275.27) |
| $R_f$ value: | 0.68 (silica gel; dichloromethane/ethanol = 19:1) |
| mass spectrum: | $(M + Na)^+$ = 298 | b) methyl 2-amino-5-(3,5-dimethyl-pyrazol-1-yl)-benzoate

Prepared by catalytic reduction (palladium, 10% on charcoal) of methyl 2-nitro-5-(3,5-dimethyl-pyrazol-1-yl)-benzoate in methanol.

| | |
|---|---|
| Yield: | 80% of theory, $C_{13}H_{15}N_3O_2$ (245.28) |
| $R_f$ value: | 0.48 (silica gel; dichloromethane/ethanol = 19:1) | c) trans-3-(naphth-2-yl)-but-2-enoic acid-N-[2-methoxycarbonyl-4-(3,5-dimethyl-pyrazol-1-yl)-phenyl]-amide Prepared analogously to Example 1 from trans-3-(naphth-2-yl)-but-2-enoic acid chloride and methyl 2-amino-5-(3,5-dimethyl-pyrazol-1-yl)-benzoate.

| | |
|---|---|
| Yield: | 62% of theory, $C_{27}H_{25}N_3O_3$ (439.52) |
| $R_f$ value: | 0.55 (silica gel; dichloromethane/ethanol = 19:1) |
| mass spectrum: | $M^+$ = 439 | d) trans-3-(naphth-2-yl)-but-2-enoic acid-N-[2-carboxy-4-(3,5-dimethyl-pyrazol-1-yl)-phenyl]-amide Prepared analogously to Example 2 from trans-3-(naphth-2-yl)-but-2-enoic acid-N-[2-methoxycarbonyl-4-(3,5-dimethyl-pyrazol-1-yl)-phenyl]-amide and sodium hydroxide solution in methanol.

| | |
|---|---|
| Yield: | 80% of theory, $C_{26}H_{23}N_3O_3$ (425.49) |
| $R_f$ value: | 0.19 (silica gel; dichloromethane/ethanol = 19:1) |
| mass spectrum: | $M^+$ = 425 |
| | $(M - H)^-$ = 424 |

EXAMPLE 120

Trans-3-(naphth-2-yl)-but-2-enoic acid-N-[2-carboxy-4-(3-methyl-5-phenyl-pyrazol-1-yl)-phenyl]-amide Prepared analogously to Example 119 from trans-3-(naphth-2-yl)-but-2-enoic acid-N-[2-methoxycarbonyl-4-(3-methyl-5-phenyl-pyrazol-1-yl)-phenyl]-amide and sodium hydroxide solution in methanol.

| | |
|---|---|
| Yield: | 84% of theory, $C_{31}H_{25}N_3O_3$ (487.56) |
| $R_f$ value: | 0.20 (silica gel; dichloromethane/ethanol = 19:1) |
| mass spectrum: | $M^+$ = 487 |
| | $(M - H)^-$ = 486 |

EXAMPLE 121

Trans-3-(naphth-2-yl)-but-2-enoic acid-N-[2-carboxy-4-(3-trifluormethyl-5-(furan-1-yl)-pyrazol-1-yl)-phenyl]-amide Prepared analogously to Example 119 from trans-3-(naphth-2-yl)-but-2-enoic acid-N-[2-methoxycarbonyl-4-(3-trifluormethyl-5-(furan-1-yl)-pyrazol-1-yl)-phenyl]-amide and sodium hydroxide solution in methanol.

| | |
|---|---|
| Yield: | 81% of theory, $C_{29}H_{20}F_3N_3O_4$ (531.50) |
| $R_f$ value: | 0.21 (silica gel; dichloromethane/ethanol = 19:1) |
| mass spectrum: | $M^+$ = 531 |
| | $(M - H)^-$ = 530 |

EXAMPLE 122

Trans-3-(2-oxo-2H-chromen-3-yl)-acrylic acid-N-(2-carboxy-phenyl)-amide

Prepared analogously to Example 31 from trans-3-(2-oxo-2H-chromen-3-yl)-acrylic acid chloride and anthranilic acid in tetrahydrofuran with the addition of triethylamine.

| | |
|---|---|
| Yield: | 30% of theory, $C_{19}H_{13}NO_5$ (335.31) |
| $R_f$ value: | 0.33 (silica gel; dichloromethane/ethanol = 9:1) |
| mass spectrum: | $M^+$ = 335 |
| | $(M - H)^-$ = 334 |

EXAMPLE 123

Trans-3-(2-oxo-2H-chromen-3-yl)-but-2-enoic acid-N-(2-carboxy-phenyl)-amide

Prepared analogously to Example 31 from trans-3-(2-oxo-2H-chromen-3-yl)-but-2-enoic acid chloride and anthranilic acid in tetrahydrofuran with the addition of triethylamine.

| Yield: | 13% of theory, $C_{20}H_{15}NO_5$ (349.35) |
| --- | --- |
| $R_f$ value: | 0.35 (silica gel; dichloromethane/ethanol = 9:1) |
| mass spectrum: | $M^+ = 349$ |
| | $(M + Na)^+ = 372$ |
| | $(M - H)^- = 348$ |

EXAMPLE 124

Trans-3-(naphth-2-yl)-but-2-enoic acid-N-[2-carboxy-4-(3-methyl-5-tert.butyl-pyrazol-1-yl)-phenyl]-amide Prepared analogously to Example 119 from trans-3-(naphth-2-yl)-but-2-enoic acid-N-[2-methoxycarbonyl-4-(3-methyl-5-tert.butyl-pyrazol-1-yl)-phenyl]-amide and sodium hydroxide solution in methanol.

| Yield: | 66% of theory, $C_{29}H_{29}N_3O_3$ (467.57) |
| --- | --- |
| $R_f$ value: | 0.20 (silica gel; dichloromethane/ethanol = 19:1) |
| mass spectrum: | $(M - H)^- = 466$ |

EXAMPLE 125

Trans-3-(naphth-2-yl)-but-2-enoic acid-N-(3-carboxy-1H-pyrazol-4-yl)-amide

Prepared analogously to Example 31 from trans-3-(naphth-2-yl)-but-2-enoic acid chloride and 4-amino-1H-pyrazol-3-carboxylic acid in dimethylformamide with the addition of pyridine.

| Yield: | 19% of theory, $C_{18}H_{15}N_3O_3$ (321.34) |
| --- | --- |
| $R_f$ value: | 0.21 (silica gel; dichloromethane/ethanol = 19:1) |
| mass spectrum: | $M^+ = 321$ |
| | $(M - H)^- = 320$ |

EXAMPLE 126

Trans-3-(naphth-2-yl)-but-2-enoic acid-N-(2-benzenesulphonylamino-carbonyl-phenyl)-amide Prepared analogously to Example 31 from trans-3-(naphth-2-yl)-but-2-enoic acid chloride and 2-benzenesulphonylaminocarbonyl-anilin in tetrahydrofuran with the addition of pyridine.

| Yield: | 85% of theory, $C_{27}H_{22}N_2O_4S$ (470.55) |
| --- | --- |
| $R_f$ value: | 0.22 (silica gel; dichloromethane/ethanol = 19:1) |
| mass spectrum: | $M^+ = 470$ |
| | $(M - H)^- = 469$ |

EXAMPLE 127

Trans-3-(3-methyl-benzothiophen-2-yl)-but-2-enoic acid-N-(2-carboxy-phenyl)-amide Prepared analogously to Example 2 from trans-3-(3-methyl-benzothio-phen-2-yl)-but-2-enoic acid-N-(2-methoxycarbonyl-phenyl)-amide and sodium hydroxide solution in methanol.

| Yield: | 71% of theory, $C_{20}H_{17}NO_3S$ (351.43) |
| --- | --- |
| $R_f$ value: | 0.34 (silica gel; dichloromethane/ethanol = 9:1) |
| mass spectrum: | $M^+ = 351$ |
| | $(M - H)^- = 350$ |

EXAMPLE 128

Trans-3-(naphth-2-yl)-but-2-enoic acid-N-(2-methanesulphonylamino-carbonyl-phenyl)-amide Prepared analogously to Example 126 from trans-3-(naphth-2-yl)-but-2-enoic acid chloride and 2-methanesulphonyl-aminocarbonyl-aniline in tetrahydrofuran with the addition of pyridine.

| Yield: | 68% of theory, $C_{22}H_{20}N_2O_4S$ (408.48) |
| --- | --- |
| $R_f$ value: | 0.20 (silica gel; dichloromethane/ethanol = 19:1) |
| mass spectrum: | $M^+ = 408$ |
| | $(M + Na)^+ = 431$ |
| | $(M - H)^- = 407$ |

EXAMPLE 129

Trans-3-(naphth-2-yl)-but-2-enoic acid-N-[2-carboxy-4-(2-phenyl-imidazol-1-yl)-phenyl]-amide Prepared analogously to Example 2 from trans-3-(naphth-2-yl)-but-2-enoic acid-N-[2-methoxycarbonyl-4-(2-phenyl-imidazol-1-yl)-phenyl]-amide and sodium hydroxide solution in methanol.

| Yield: | 89% of theory, $C_{30}H_{23}N_3O_3$ (473.54) |
| --- | --- |
| $R_f$ value: | 0.23 (silica gel; dichloromethane/ethanol = 9:1) |
| mass spectrum: | $(M + H)^+ = 474$ |
| | $(M + Na)^+ = 496$ |
| | $(M - H)^- = 472$ |

EXAMPLE 130

Trans-3-(naphth-2-yl)-but-2-enoic acid-N-[2-carboxy-4-(2-methyl-benzimidazol-1-yl)-phenyl]-amide Prepared analogously to Example 2 from trans-3-(naphth-2-yl)-but-2-enoic acid-N-[2-methoxycarbonyl-4-(2-methyl-benzimidazol-1-yl)-phenyl]-amide and sodium hydroxide solution in methanol.

| Yield: | 87% of theory, $C_{29}H_{23}N_3O_3$ (461.52) |
| --- | --- |
| $R_f$ value: | 0.22 (silica gel; dichloromethane/ethanol = 9:1) |
| mass spectrum: | $(M + H)^+ = 462$ |
| | $(M + Na)^+ = 484$ |
| | $(M - H)^- = 460$ |

EXAMPLE 131

Trans-3-(naphth-2-yl)-but-2-enoic acid-N-(2,3-dicarboxy-phenyl)-amide

Prepared analogously to Example 2 from trans-3-(naphth-2-yl)-but-2-enoic acid-N-(2,3-dimethoxycarbonyl-phenyl)-amide and sodium hydroxide solution in methanol.

| Yield: | 80% of theory, $C_{22}H_{17}NO_5$ (375.38) |
|---|---|
| $R_f$ value: | 0.09 (silica gel; dichloromethane/ethanol = 9:1) |
| mass spectrum: | $(M + Na)^+ = 398$ |
| | $(M - H)^- = 374$ |

EXAMPLE 132

Trans-3-(naphth-2-yl)-but-2-enoic acid-N-[2-carboxy-4-(imidazol-1-yl)-5-fluoro-phenyl]-amide Prepared analogously to Example 2 from trans-3-(naphth-2-yl)-but-2-enoic acid-N-[2-methoxycarbonyl-4-(imidazol-1-yl)-5-fluoro-phenyl]-amide and sodium hydroxide solution in methanol.

| Yield: | 62% of theory, $C_{24}H_{18}FN_3O_3$ (415.43) |
|---|---|
| $R_f$ value: | 0.17 (silica gel; dichloromethane/ethanol = 9:1) |
| mass spectrum: | $M^+ = 415$ |
| | $(M - H)^- = 414$ |

EXAMPLE 133

Trans-3-(benzothiophen-2-yl)-but-2-enoic acid-N-(2-carboxy-phenyl)-amide

Prepared analogously to Example 2 from trans-3-(benzothiophen-2-yl)-but-2-enoic acid-N-(2-methoxycarbonyl-phenyl)-amide and sodium hydroxide solution in methanol.

| Yield: | 89% of theory, $C_{19}H_{15}NO_3S$ (337.40) |
|---|---|
| $R_f$ value: | 0.43 (silica gel; dichloromethane/ethanol = 9:1) |
| mass spectrum: | $(M + Na)^+ = 360$ |
| | $(M - H)^- = 336$ |

EXAMPLE 134

Trans-3-(naphth-2-yl)-but-2-enoic acid-N-(2-carboxy-4-methane-sulphonyloxy-phenyl)-amide 0.5 ml of (4.37 mmol) of methanesulphonyl chloride are slowly added dropwise to a solution of 0.21 g (0.605 mmol) of trans-3-(naphth-2-yl)-but-2-enoic acid-N-(2-carboxy-4-hydroxy-phenyl)-amide in 15 ml of 1N sodium hydroxide solution, with stirring, at ambient temperature, whilst the solution is kept constantly alkaline by the addition of sodium hydroxide solution. After the reaction has ended the mixture is acidified with 2N hydrochloric acid, then extracted three times with 20 ml of ethyl acetate, the extracts are dried over sodium sulphate and evaporated to dryness in vacuo. The crude product thus obtained was purified by column chromatography (silica gel; eluant: dichloromethane with 2 to 3% ethanol).

| Yield: | 35% of theory, $C_{22}H_{19}NO_6S$ (425.46) |
|---|---|
| $R_f$ value: | 0.27 (silica gel; dichloromethane/ethanol = 19:1) |
| mass spectrum: | $M^+ = 425$ |
| | $(M - H)^- = 424$ |

EXAMPLE 135

Trans-3-(6-fluoro-naphth-2-yl)-acrylic acid-N-(2-carboxy-phenyl)-amide

Prepared analogously to Example 2 from trans-3-(6-fluoro-naphth-2-yl)-acrylic acid-N-(2-methoxycarbonyl-phenyl)-amide and sodium hydroxide solution in methanol.

| Yield: | 91% of theory, $C_{20}H_{14}FNO_3$ (335.34) |
|---|---|
| $R_f$ value: | 0.19 (silica gel; dichloromethane/ethanol = 19:1) |
| mass spectrum: | $(M + H)^+ = 336$ |
| | $(M + Na)^+ = 358$ |
| | $(M - H)^- = 334$ |

EXAMPLE 136

Trans-2-methyl-3-(6-fluoro-naphth-2-yl)-acrylic acid-N-(2-carboxy-phenyl)-amide

Prepared analogously to Example 2 from trans-2-methyl-3-(6-fluoro-naphth-2-yl)-acrylic acid-N-(2-methoxycarbonyl-phenyl)-amide and sodium hydroxide solution in methanol.

| Yield: | 82% of theory, $C_{21}H_{16}FNO_3$ (349.37) |
|---|---|
| $R_f$ value: | 0.24 (silica gel; dichloromethane/ethanol = 19:1) |
| mass spectrum: | $M^+ = 349$ |
| | $(M - H)^- = 348$ |

EXAMPLE 137

Trans-3-(6-fluoro-naphth-2-yl)-acrylic acid-N-(2-carboxy-4-fluoro-phenyl)-amide

Prepared analogously to Example 31 from trans-3-(6-fluoro-naphth-2-yl)-acrylic acid chloride and 4-fluoroanthranilic acid in tetrahydrofuran with the addition of pyridine.

| Yield: | 14% of theory, $C_{20}H_{13}F_2NO_3$ (353.32) |
|---|---|
| $R_f$ value: | 0.19 (silica gel; dichloromethane/ethanol = 19:1) |
| mass spectrum: | $M^+ = 353$ |
| | $M - H)^- = 352$ |

EXAMPLE 138

Trans-2-methyl-3-(6-fluoro-naphth-2-yl)-acrylic acid-N-(2-carboxy-4-fluoro-phenyl)-amide Prepared analogously to Example 31 from trans-2-methyl-3-(6-fluoronaphth-2-yl)-acrylic acid chloride and 4-fluoroanthranilic acid in tetrahydrofuran with the addition of pyridine.

| Yield: | 20% of theory, |
| --- | --- |
| | $C_{21}H_{15}F_2NO_3$ (367.36) |
| $R_f$ value: | 0.20 (silica gel; dichloromethane/ethanol = 19:1) |
| mass spectrum: | $M^+ = 367$ |
| | $(M - H)^- = 366$ |

EXAMPLE 139

Trans-3-(naphth-2-yl)-but-2-enoic acid-N-[2-carboxy-4-(2-N,N-dimethylamino-ethyloxy)-phenyl]-amide Prepared analogously to Example 2 from trans-3-(naphth-2-yl)-but-2-enoic acid-N-[2-ethoxycarbonyl-4-(2-N,N-dimethylamino-ethyl-oxy)-phenyl]-amide and sodium hydroxide solution in methanol.

| Yield: | 20% of theory, |
| --- | --- |
| | $C_{25}H_{26}N_2O_4$ (418.50) |
| mass spectrum: | $M^+ = 418$ |
| | $(M - H)^- = 417$ |

EXAMPLE 140

3-(naphth-2-yl)-butanoic acid-N-(2-carboxy-phenyl)-amide

Prepared analogously to Example 2 from 3-(naphth-2-yl)-butanoic acid-N-(2-methoxycarbonyl-phenyl)-amide and sodium hydroxide solution in methanol.

| Yield: | 83% of theory, |
| --- | --- |
| | $C_{21}H_{19}NO_3$ (333.39) |
| $R_f$ value: | 0.24 (silica gel; dichloromethane/ethanol = 19:1) |
| mass spectrum: | $(M + H)^+ = 334$ |
| | $(M + Na)^+ = 456$ |
| | $(M - H)^- = 332$ |

EXAMPLE 141

Trans-3-(naphth-2-yl)-but-2-enoic acid-N-(2-carboxy-4,5-methylenedioxy-phenyl)-amide Prepared analogously to Example 2 from trans-3-(naphth-2-yl)-but-2-enoic acid-N-(2-methoxycarbonyl-4,5-methylenedioxy-phenyl)-amide and sodium hydroxide solution in methanol.

| Yield: | 95% of theory, |
| --- | --- |
| | $C_{22}H_{17}NO_5$ (375.38) |
| $R_f$ value: | 0.21 (silica gel; dichloromethane/ethanol = 19:1) |
| mass spectrum: | $(M - H)^- = 374$ |

EXAMPLE 142

Trans-3-(naphth-2-yl)-cyclopropanecarboxylic acid-N-(2-carboxy-phenyl)-amide

Prepared analogously to Example 2 from trans-3-(naphth-2-yl)-cyclopropanecarboxylic acid-N-(2-methoxycarbonyl-phenyl)-amide and sodium hydroxide solution in methanol.

| Yield: | 59% of theory |
| --- | --- |
| | $C_{21}H_{17}NO_3$ (331.38) |
| $R_f$ value: | 0.18 (silica gel; dichloromethane/ethanol = 19:1) |
| mass spectrum: | $(M - H)^- = 330$ |

EXAMPLE 143

Trans-3-(naphth-2-yl)-but-2-enoic acid-N-(2-carboxy-4-iodo-phenyl)-amide

Prepared analogously to Example 31 from trans-3-(naphth-2-yl)-but-2-enoic acid chloride and 4-iodo-anthranilic acid in tetrahydrofuran with the addition of triethylamine.

| Yield: | 32% of theory, |
| --- | --- |
| | $C_{21}H_{16}INO_3$ (457.27) |
| $R_f$ value: | 0.19 (silica gel; dichloromethane/ethanol = 50:1) |
| mass spectrum: | $(M - H)^- = 456$ |

EXAMPLE 144

Trans-3-(naphth-2-yl)-but-2-enoic acid-N-(4-carboxy-pyridin-3-yl)-amide

Prepared analogously to Example 2 from trans-3-(naphth-2-yl)-but-2-enoic acid-N-(4-methoxycarbonyl-pyridin-3-yl)-amide and sodium hydroxide solution in methanol.

| Yield: | 26% of theory, |
| --- | --- |
| | $C_{20}H_{16}N_2O_3$ (332.36) |
| $R_f$ value: | 0.18 (silica gel; dichloromethane/ethanol = 9:1) |
| mass spectrum: | $(M + Na)^+ = 355$ |
| | $(M - H)^- = 331$ |

EXAMPLE 145

Trans-3-(naphth-2-yl)-but-2-enoic acid-N-[2-carboxy-5-(morpholin-1-yl-carbonyl)-phenyl]-amide Prepared analogously to Example 2 from trans-3-(naphth-2-yl)-but-2-enoic acid-N-[2-methoxycarbonyl-5-(morpholin-1-yl-carbonyl)-phenyl]-amide and sodium hydroxide solution in methanol.

| Yield: | 90% of theory, |
| --- | --- |
| | $C_{26}H_{24}N_2O_5$ (444.49) |
| $R_f$ value: | 0.27 (silica gel; dichloromethane/ethanol = 9:1) |
| mass spectrum: | $M^+ = 444$ |
| | $(M - H)^- = 443$ |
| | $(M + Na)^+ = 467$ |

EXAMPLE 146

Trans-3-(naphth-2-yl)-but-2-enoic acid-N-[2-carboxy-5-(N-ethyl-N-methyl-aminocarbonyl)-phenyl]-amide Prepared analogously to Example 2 from trans-3-(naphth-2-yl)-but-2-enoic acid-N-[2-methoxycarbonyl-5-(N-ethyl- N-methyl-aminocarbonyl)-phenyl]-amide and sodium hydroxide solution in methanol.

| Yield: | 71% of theory, $C_{25}H_{24}N_2O_4$ (416.48) |
|---|---|
| $R_f$ value: | 0.22 (silica gel; dichloromethane/ethanol = 19:1) |
| mass spectrum: | $M^+$ = 416 |
| | $(M - H)^-$ = 415 |

EXAMPLE 147

Trans-3-(naphth-2-yl)-but-2-enoic acid-N-[2-carboxy-5-(piperidin-1-yl-carbonyl)-phenyl]-amide Prepared analogously to Example 2 from trans-3-(naphth-2-yl)-but-2-enoic acid-N-[2-methoxycarbonyl-5-(piperidin-1-yl-carbonyl)-phenyl]-amide and sodium hydroxide solution in methanol.

| Yield: | 77% of theory $C_{27}H_{26}N_2O_4$ (442.51) |
|---|---|
| $R_f$ value: | 0.22 (silica gel; dichloromethane/ethanol = 19:1) |
| mass spectrum: | $M^+$ = 442 |
| | $(M - H)^-$ = 441 |

EXAMPLE 148

Trans-3-(naphth-2-yl)-but-2-enoic acid-N-[2-carboxy-5-(pyrrolidin-1-yl-carbonyl)-phenyl]-amide Prepared analogously to Example 2 from trans-3-(naphth-2-yl)-but-2-enoic acid-N-[2-methoxycarbonyl-5-(pyrrolidin-1-yl-carbonyl)-phenyl]-amide and sodium hydroxide solution in methanol.

| Yield: | 80% of theory, $C_{26}H_{24}N_2O_4$ (428.49) |
|---|---|
| $R_f$ value: | 0.22 (silica gel; dichloromethane/ethanol = 19:1) |
| mass spectrum: | $(M - H)^-$ = 427 |
| | $(M + Na)^+$ = 451 |

EXAMPLE 149

Trans-3-(naphth-2-yl)-but-2-enoic acid-N-[2-carboxy-5-(N-isopropyl-N-methyl-carbonyl)-phenyl]-amide Prepared analogously to Example 2 from trans-3-(naphth-2-yl)-but-2-enoic acid-N-[2-methoxycarbonyl-5-(N-isopropyl-N-methyl-carbonyl)-phenyl]-amide and sodium hydroxide solution in methanol.

| Yield: | 69% of theory $C_{26}H_{26}N_2O_4$ (430.50) |
|---|---|
| $R_f$ value: | 0.24 (silica gel; dichloromethane/ethanol = 19:1) |
| mass spectrum: | $(M - H)^-$ = 429 |
| | $(M + Na)^+$ = 453 |

EXAMPLE 150

Trans-3-(naphth-2-yl)-but-2-enoic acid-N-[2-carboxy-5-(4-methyl-piperazin-1-yl-carbonyl)-phenyl]-amide Prepared analogously to Example 2 from trans-3-(naphth-2-yl)-but-2-enoic acid-N-[2-methoxycarbonyl-5-(4-methyl-piperazin-1-yl-carbonyl)-phenyl]-amide and sodium hydroxide solution in methanol.

| Yield: | 40% of theory, $C_{27}H_{27}N_3O_4$ (457.53) |
|---|---|
| $R_f$ value: | 0.19 (silica gel; dichloromethane/ethanol = 19:1) |
| mass spectrum: | $M^+$ = 457 |
| | $(M - H)^-$ = 456 |
| | $(M + Na)^+$ = 480 |

EXAMPLE 151

Trans-3-(naphth-2-yl)-4,4,4-trifluoro-but-2-enoic acid-N-(2-carboxy-phenyl)-amide Prepared analogously to Example 2 from trans-3-(naphth-2-yl)-4,4,4-trifluoro-but-2-enoic acid-N-(2-methoxycarbonyl-phenyl)-amide and sodium hydroxide solution in methanol.

| Yield: | 76% of theory, $C_{21}H_{14}F_3NO_3$ (358.34) |
|---|---|
| $R_f$ value: | 0.22 (silica gel; dichloromethane/ethanol = 19:1) |
| mass spectrum: | $(M - H)^-$ = 384 |
| | $(M + Na)^+$ = 408 |

EXAMPLE 152

Trans-3-(3,4-dibromophenyl)-but-2-enoic acid-N-(2-carboxy-phenyl)-amide

Prepared analogously to Example 31 from trans-3-(3,4-dibromophenyl)-but-2-enoic acid chloride and 2-aminobenzoic acid in dimethylformamide.

| Yield: | 16% of theory, $C_{17}H_{13}Br_2NO_3$ (439.10) |
|---|---|
| $R_f$ value: | 0.15 (silica gel; dichloromethane/ethanol = 50:1) |
| mass spectrum: | $(M—H)^-$ = 438 |

EXAMPLE 153

Trans-3-(4-ethynylphenyl)-but-2-enoic acid-N-(2-carboxy-phenyl)-amide

Prepared analogously to Example 2 from trans-3-(4-trimethylsilanylethynylphenyl)-but-2-enoic acid-N-(2-methoxycarbonyl-phenyl)-amide and potassium hydroxide solution in methanol.

| Yield: | 53% of theory, $C_{19}H_{15}NO_3$ (305.34) |
|---|---|
| $R_f$ value: | 0.6 (silica gel; dichloromethane/ethanol = 9:1) |
| mass spectrum: | $(M - H)^-$ = 304 |

EXAMPLE 154

Trans-3-(3-ethynylphenyl)-but-2-enoic acid-N-(2-carboxy-phenyl)-amide

Prepared analogously to Example 2 from trans-3-(3-trimethylsilanylethynylphenyl)-but-2-enoic acid-N-(2- methoxycarbonyl-phenyl)-amide and potassium hydroxide solution in methanol.

| | |
|---|---|
| Yield: | 60% of theory, $C_{19}H_{15}NO_3$ (305.34) |
| $R_f$ value: | 0.5 (silica gel; dichloromethane/ethanol = 9:1) |
| mass spectrum: | $(M - H)^- = 304$ |

EXAMPLE 155

Trans-3-(3,4-dibromophenyl)-but-2-enoic acid-N-(2-carboxy-4,5-dimethoxy-phenyl)-amide Prepared analogously to Example 2 from trans-3-(3,4-dibromophenyl)-but-2-enoic acid-N-(2-methoxycarbonyl-4,5-dimethoxy-phenyl)-amide and sodium hydroxide solution in methanol/dichloromethane.

| | |
|---|---|
| Yield: | 40% of theory, $C_{19}H_{17}Br_2NO_5$ (499.16) |
| $R_f$ value: | 0.3 (silica gel; dichloromethane/ethanol = 19:1) |
| mass spectrum: | $M^+ = 497/499/501$ (bromine isotopes) |

EXAMPLE 156

Trans-3-(3,4-dibromophenyl)-but-2-enoic acid-N-(2-carboxy-4-methoxy-5-methyl-phenyl)-amide Prepared analogously to Example 2 from trans-3-(3,4-dibromophenyl)-but-2-enoic acid-N-(2-methoxycarbonyl-4-methoxy-5-methyl-phenyl)-amide and sodium hydroxide solution in methanol/dichloromethane.

| | |
|---|---|
| Yield: | 59% of theory, $C_{19}H_{17}Br_2NO_4$ (483.15) |
| $R_f$ value: | 0.3 (silica gel; dichloromethane/ethanol = 19:1) |
| mass spectrum: | $M^+ = 481/83/85$ (bromine isotopes) |

EXAMPLE 157

Trans-3-(3,5-dibromo-4-ethylphenyl)-but-2-enoic acid-N-(2-carboxy-phenyl)-amide

Prepared analogously to Example 2 from trans-3-(3,5-dibromo-4-ethylphenyl)-but-2-enoic acid-N-(2-methoxycarbonyl-phenyl)-amide and sodium hydroxide solution in methanol.

| | |
|---|---|
| Yield: | 49% of theory, $C_{19}H_{17}Br_2NO_3$ (467.16) |
| $R_f$ value: | 0.5 (silica gel; dichloromethane/ethanol = 19:1) |
| mass spectrum: | $M^+ = 465/67/69$ (bromine isotopes) |

EXAMPLE 158

Trans-3-(3-bromo-4-chlorophenyl)-but-2-enoic acid-N-(2-carboxy-phenyl)-amide

Prepared analogously to Example 2 from trans-3-(3-bromo-4-chlorophenyl)-but-2-enoic acid-N-(2-methoxycarbonyl-phenyl)-amide and sodium hydroxide solution in methanol.

| | |
|---|---|
| Yield: | 36% of theory, $C_{17}H_{13}BrClNO_3$ (394.65) |
| $R_f$ value: | 0.3 (silica gel; dichloromethane/ethanol = 19:1) |
| mass spectrum: | $(M - H)^- = 392/94/96$ (chlorine-bromine isotopes) |

EXAMPLE 159

Trans-3-(3-chloro-4-bromophenyl)-but-2-enoic acid-N-(2-carboxy-phenyl)-amide

Prepared analogously to Example 2 from trans-3-(3-chloro-4-bromophenyl)-but-2-enoic acid-N-(2-methoxycarbonyl-phenyl)-amide and sodium hydroxide solution in methanol.

| | |
|---|---|
| Yield: | 36% of theory, $C_{17}H_{13}BrClNO_3$ (394.65) |
| $R_f$ value: | 0.4 (silica gel; dichloromethane/ethanol = 19:1) |
| mass spectrum: | $(M - H)^- = 392/94/96$ (chlorine-bromine isotopes) |

EXAMPLE 160

Trans-3-(naphth-2-yl)-but-2-enoic acid-N-(2-carboxy-6-methyl-phenyl)-amide

Prepared analogously to Example 2 from trans-3-(naphth-2-yl)-but-2-enoic acid-N-(2-methoxycarbonyl-6-methyl-phenyl)-amide and sodium hydroxide solution in methanol.

| | |
|---|---|
| Yield: | 76% of theory, $C_{22}H_{19}NO_3$ (345.41) |
| $R_f$ value: | 0.4 (silica gel; dichloromethane/ethanol = 19:1) |
| mass spectrum: | $(M - H)^- = 344$ |
| | $(M + Na)^+ = 368$ |

EXAMPLE 161

Trans-3-(naphth-2-yl)-but-2-enoic acid-N-(2-carboxy-6-methoxy-phenyl)-amide

Prepared analogously to Example 2 from trans-3-(naphth-2-yl)-but-2-enoic acid-N-(2-methoxycarbonyl-6-methoxy-phenyl)-amide and sodium hydroxide solution in methanol.

| | |
|---|---|
| Yield: | 80% of theory, $C_{22}H_{19}NO_4$ (361.40) |
| $R_f$ value: | 0.3 (silica gel; dichloromethane/ethanol = 19:1) |
| mass spectrum: | $(M - H)^- = 360$ |
| | $(M + Na)^+ = 384$ |

EXAMPLE 162

Trans-3-(naphth-2-yl)-but-2-enoic acid-N-(2-carboxy-6-chloro-phenyl)-amide

Prepared analogously to Example 2 from trans-3-(naphth-2-yl)-but-2-enoic acid-N-(2-methoxycarbonyl-6-chloro-phenyl)-amide and sodium hydroxide solution in methanol.

| Yield: | 67% of theory, |
| --- | --- |
| | $C_{21}H_{16}ClNO_3$ (365.81) |
| $R_f$ value: | 0.15 (silica gel; dichloromethane/ethanol = 19:1) |
| mass spectrum: | $(M - H)^- = 364/366$ (chlorine isotopes) |

EXAMPLE 163

Trans-3-(naphth-2-yl)-but-2-enoic acid-N-(2-carboxy-4-methylamino-phenyl)-amide-trifluoroacetate 650 mg (1.4 mmol) of trans-3-(naphth-2-yl)-but-2-enoic acid-N-[2-carboxy-4-(N-methyl-N-tert.butoxycarbonyl-amino-phenyl]-amide are stirred in 10 ml of dichloromethane and 2 ml of trifluoroacetic acid for 18 hours. The solvent is distilled off and the residue is purified by column chromatography over silica gel (eluant: dichloromethane with 1 to 5% ethanol).

| Yield: | 79% of theory, |
| --- | --- |
| | $C_{22}H_{20}N_2O_3 \times CF_3COOH$ (360.42/474.44) |
| $R_f$ value: | 0.7 (silica gel; dichloromethane/ethanol = 9:1) |
| mass spectrum: | $(M - H)^- = 359$ |
| | $M^+ = 360$ |

EXAMPLE 164

Trans-3-(naphth-2-yl)-but-2-enoic acid-N-[2-carboxy-4-(bis-2-methoxy-ethyl-amino)-phenyl]-amide Prepared analogously to Example 2 from trans-3-(naphth-2-yl)-but-2-enoic acid-N-[2-methoxycarbonyl-4-(bis-2-methoxy-ethyl-amino)-phenyl]-amide and sodium hydroxide solution in methanol.

| Yield: | 79% of theory, |
| --- | --- |
| | $C_{27}H_{30}N_2O_5$ (462.55) |
| $R_f$ value: | 0.3 (silica gel; dichloromethane/ethanol = 19:1) |
| mass spectrum: | $(M + H)^+ = 463$ |

EXAMPLE 165

Trans-3-(naphth-2-yl)-but-2-enoic acid-N-(2-carboxy-4,5,6-trimethoxy-phenyl)-amide Prepared analogously to Example 2 from trans-3-(naphth-2-yl)-but-2-enoic acid-N-(2-methoxycarbonyl-4,5,6-trimethoxy-phenyl)-amide and sodium hydroxide solution in methanol.

| Yield: | 46% of theory, |
| --- | --- |
| | $C_{24}H_{23}NO_6$ (421.45) |
| $R_f$ value: | 0.2 (silica gel; dichloromethane/ethanol = 19:1) |
| mass spectrum: | $(M - H)^- = 420$ |

EXAMPLE 166

Trans-3-(naphth-2-yl)-but-2-enoic acid-N-(2-carboxy-4-amino-phenyl)-amide-trifluoroacetate Prepared analogously to Example 163 from trans-3-(naphth-2-yl)-but-2-enoic acid-N-(2-carboxy-4-tert.butoxycarbonylamino-phenyl)-amide and trifluoroacetic acid in dichloromethane.

| Yield: | 81% of theory, |
| --- | --- |
| | $C_{21}H_{18}N_2O_3 \times CF_3COOH$ (346.39/460.413) |
| $R_f$ value: | 0.3 (silica gel; dichloromethane/ethanol = 9:1) |
| mass spectrum: | $(M - H)^- = 345$ |

EXAMPLE 167

Trans-3-(naphth-2-yl)-but-2-enoic acid-N-(2-carboxy-4-benzenesulphonylamino-phenyl)-amide Prepared analogously to Example 2 from trans-3-(naphth-2-yl)-but-2-enoic acid-N-(2-ethoxycarbonyl-4-benzenesulphonylamino-phenyl)-amide and sodium hydroxide solution in methanol.

| Yield: | 82% of theory, |
| --- | --- |
| | $C_{27}H_{22}N_2O_5S$ (486.55) |
| $R_f$ value: | 0.4 (silica gel; dichloromethane/ethanol = 9:1) |
| mass spectrum: | $(M - H)^- = 485$ |

EXAMPLE 168

Trans-3-(naphth-2-yl)-but-2-enoic acid-N-(2-carboxy-6-fluoro-phenyl)-amide

Prepared analogously to Example 31 from trans-(naphth-2-yl)-but-2-enoic acid chloride and 2-amino-3-fluorobenzoic acid in tetrahydrofuran with the addition of triethylamine.

| Yield: | 33% of theory, |
| --- | --- |
| | $C_{21}H_{16}FNO_3$ (349.36) |
| $R_f$ value: | 0.2 (silica gel; dichloromethane/ethanol = 19:1) |
| mass spectrum: | $(M - H)^- = 348$ |

EXAMPLE 169

Trans-3-(naphth-2-yl)-but-2-enoic acid-N-(2-carboxy-4-methanesulphonylamino-phenyl)-amide Prepared analogously to Example 2 from trans-3-(naphth-2-yl)-but-2-enoic acid-N-(2-ethoxycarbonyl-4-methanesulphonylamino-phenyl)-amide and sodium hydroxide solution in methanol.

| Yield: | 80% of theory, |
| --- | --- |
| | $C_{22}H_{20}N_2O_5S$ (424.48) |
| $R_f$ value: | 0.15 (silica gel; dichloromethane/ethanol = 9:1) |
| mass spectrum: | $(M - H)^- = 423$ |
| | $(M + Na)^+ = 447$ |

EXAMPLE 170

Trans-3-(3-bromo-4-chlorophenyl)-but-2-enoic acid-N-(2-carboxy-4,5-dimethoxy-phenyl)-amide Prepared analogously to Example 2 from trans-3-(3-bromo-4-chlorophenyl)-but-2-enoic acid-N-(2- methoxycarbonyl-4,5-dimethoxy-phenyl)-amide and potassium hydroxide solution in methanol/dichloromethane.

| Yield: | 15% of theory, $C_{19}H_{17}BrClNO_5$ (454.70) |
|---|---|
| $R_f$ value: | 0.2 (silica gel; dichloromethane/ethanol = 19:1) |
| mass spectrum: | $(M - H)^- = 452/54/56$ (bromine-chloride isotopes) |

EXAMPLE 171

Trans-3-(3-chloro-4-bromophenyl)-but-2-enoic acid-N-(2-carboxy-4,5-dimethoxy-phenyl)-amide Prepared analogously to Example 2 from trans-3-(3-chloro-4-bromophenyl)-but-2-enoic acid-N-(2-methoxycarbonyl-4,5-dimethoxy-phenyl)-amide and potassium hydroxide solution in methanol.

| Yield: | 45% of theory, $C_{19}H_{17}BrClNO_5$ (454.70) |
|---|---|
| $R_f$ value: | 0.2 (silica gel; dichloromethane/ethanol = 19:1) |
| mass spectrum: | $(M - H)^- = 452/54/56$ (bromine-chloride isotopes) |

EXAMPLE 172

Trans-3-(4-iodophenyl)-but-2-enoic acid-N-(2-carboxyphenyl)-amide

Prepared analogously to Example 2 from trans-3-(4-iodophenyl)-but-2-enoic acid-N-(2-methoxycarbonylphenyl)-amide and sodium hydroxide solution in methanol/water.

| Yield: | 16% of theory, $C_{17}H_{14}INO_3$ (407.21) |
|---|---|
| mass spectrum: | $(M - H)^- = 406$ |

EXAMPLE 173

Trans-3-(naphth-2-yl)-but-2-enoic acid-N-(2-carboxy-5-methyl-phenyl)-amide

Prepared analogously to Example 31 from trans-(naphth-2-yl)-but-2-enoic acid chloride and 2-amino-4-methyl-benzoic acid in tetrahydrofuran with the addition of triethylamine.

| Yield: | 4% of theory, $C_{22}H_{19}NO_3$ (345.40) |
|---|---|
| $R_f$ value: | 0.2 (silica gel; dichloromethane/ethanol = 19:1) |
| mass spectrum: | $(M - H)^- = 344$ |

EXAMPLE 174

Trans-3-(naphth-2-yl)-but-2-enoic acid-N-(2-carboxy-4,6-difluoro-phenyl)-amide

Prepared analogously to Example 31 from trans-(naphth-2-yl)-but-2-enoic acid chloride and 2-amino-3,5-difluoro-benzoic acid in tetrahydrofuran with the addition of triethylamine.

| Yield: | 8% of theory, $C_{21}H_{15}F_2NO_3$ (367.35) |
|---|---|
| $R_f$ value: | 0.1 (silica gel; dichloromethane/ethanol = 19:1) |
| mass spectrum: | $(M - H)^- = 366$ |

EXAMPLE 175

Trans-3-(naphth-2-yl)-but-2-enoic acid-N-[2-carboxy-5-(isopropylaminocarbonyl)-phenyl]-amide Prepared analogously to Example 2 from trans-3-(naphth-2-yl)-but-2-enoic acid-N-[2-methoxycarbonyl-5-(isopropylaminocarbonyl)-phenyl]-amide and potassium hydroxide solution in methanol.

| Yield: | 5% of theory, $C_{25}H_{24}N_2O_4$ (416.48) |
|---|---|
| $R_f$ value: | 0.3 (silica gel; petroleum ether/ethyl acetate = 1:9) |
| mass spectrum: | $(M - H)^- = 415$ |
| | $(M + H)^+ = 417$ |
| | $(M - Na)^+ = 439$ |
| | $M^+ = 416$ |

EXAMPLE 176

Trans-3-(naphth-2-yl)-but-2-enoic acid-N-[2-carboxy-5-(ethylaminocarbonyl)-phenyl]-amide Prepared analogously to Example 2 from trans-3-(naphth-2-yl)-but-2-enoic acid-N-[2-methoxycarbonyl-5-(ethylaminocarbonyl)-phenyl]-amide and potassium hydroxide solution in ethanol.

| Yield: | 33% of theory, $C_{24}H_{22}N_2O_4$ (402.45) |
|---|---|
| $R_f$ value: | 0.4 (silica gel; dichloromethane/ethanol = 4:1) |
| mass spectrum: | $(M - H)^- = 401$ |
| | $(M + Na)^+ = 425$ |

EXAMPLE 177

Trans-3-(naphth-2-yl)-but-2-enoic acid-N-(2-carboxy-4-nitro-phenyl)-amide

Prepared analogously to Example 2 from trans-3-(naphth-2-yl)-but-2-enoic acid-N-(2-methoxycarbonyl-4-nitro-phenyl)-amide and lithium hydroxide in water/tetrahydrofuran.

| Yield: | 93% of theory, $C_{21}H_{16}N_2O_5$ (376.37) |
|---|---|
| $R_f$ value: | 0.2 (silica gel; dichloromethane/ethanol = 9:1) |
| mass spectrum: | $(M - H)^- = 375$ |

EXAMPLE 178

Trans-3-(naphth-2-yl)-but-2-enoic acid-N-[2-carboxy-5-(propylaminocarbonyl)-phenyl]-amide Prepared analogously to Example 2 from trans-3-(naphth-2-yl)-but-2-enoic acid-N-[2-methoxycarbonyl-5-

(propylaminocarbonyl)-phenyl]-amide and potassium hydroxide solution in ethanol.

| Yield: | 58% of theory, $C_{25}H_{24}N_2O_4$ (416.41) |
|---|---|
| $R_f$ value: | 0.15 (silica gel; dichloromethane/ethanol = 9:1) |
| mass spectrum: | $(M - H)^- = 415$ |

EXAMPLE 179

Trans-3-(naphth-2-yl)-but-2-enoic acid-N-(2,5-bis-hydroxymethyl-phenyl)-amide 1.0 g (2.5 mmol) of trans-3-(naphth-2-yl)-but-2-enoic acid-N-(2,5-bis-methoxycarbonyl-phenyl)-amide are dissolved in 70 ml of tetrahydrofuran, 10 ml (10 mmol) of lithium triethyl borohydride (1 molar in tetrahydrofuran) are added at −70° C. and slowly warmed to ambient temperature. Then 100 ml of water are added dropwise and extracted with ethyl acetate. The combined organic extracts are dried and evaporated down. The residue is purified by column chromatography over silica gel (eluant: petroleum ether/ethyl acetate=7:3).

| Yield: | 25% of theory, $C_{22}H_{21}NO_3$ (347.41) |
|---|---|
| $R_f$ value: | 0.2 (silica gel; petroleum ether/ethyl acetate = 4:6) |
| mass spectrum: | $(M - H)^- = 346$ |
| | $(M + Na)^+ = 370$ |

EXAMPLE 180

Trans-3-(naphth-2-yl)-but-2-enoic acid-N-[2-carboxy-5-(methylaminocarbonyl)-phenyl]-amide Prepared analogously to EXAMPLE 2 from trans-3-(naphth-2-yl)-but-2-enoic acid-N-[2-methoxycarbonyl-5-(methylaminocarbonyl)-phenyl]-amide and lithium hydroxide in methanol/water.

| Yield: | 30% of theory, $C_{23}H_{20}N_2O_4$ (388.42) |
|---|---|
| $R_f$ value: | 0.36 (silica gel; dichloromethane/ethanol = 3:1) |
| mass spectrum: | $(M - H)^- = 387$ |
| | $(M + Na)^+ = 411$ |

EXAMPLE 181

Trans-3-(naphth-2-yl)-but-2-enoic acid-N-[2-carboxy-5-(dimethylaminocarbonyl)-phenyl]-amide Prepared analogously to Example 2 from trans-3-(naphth-2-yl)-but-2-enoic acid-N-[2-methoxycarbonyl-5-(dimethylaminocarbonyl)-phenyl]-amide and lithium hydroxide in methanol/water.

| Yield: | 41% of theory, $C_{24}H_{22}N_2O_4$ (402.45) |
|---|---|
| $R_f$ value: | 0.43 (silica gel; dichloromethane/ethanol = 3:1) |
| mass spectrum: | $(M - H)^- = 401$ |
| | $(M + Na)^+ = 425$ |

EXAMPLE 182

Trans-3-(naphth-2-yl)-but-2-enoic acid-N-(2-carboxy-5-bromo-phenyl)-amide

Prepared analogously to Example 31 from trans-(naphth-2-yl)-but-2-enoic acid chloride and 2-amino-4-bromo-benzoic acid in pyridine.

| Yield: | 58% of theory, $C_{21}H_{16}BrNO_3$ (410.27) |
|---|---|
| $R_f$ value: | 0.65 (silica gel; dichloromethane/ethanol = 3:1) |
| mass spectrum: | $(M - H)^- = 408/410$ |

EXAMPLE 183

Trans-3-(naphth-2-yl)-but-2-enoic acid-N-(2-hydroxymethyl-phenyl)-amide 1.0 g (1.8 mmol) of trans-3-(naphth-2-yl)-but-2-enoic acid-N-[2-(tert.butyl-diphenylsilanyloxymethyl)-phenyl]-amide are stirred into 30 ml of tetrahydrofuran and 2 ml (2 mmol) of tetrabutylammonium fluoride (1 molar in tetrahydrofuran) for 6 hours. The solvent is distilled off, the residue is distributed in ethyl acetate/water, the combined organic extracts are dried and evaporated down. The crude product is purified by column chromatography over silica gel (eluant: dichloromethane/ethanol 0 to 2%).

| Yield: | 67% of theory, $C_{21}H_{19}NO_2$ (317.39) |
|---|---|
| $R_f$ value: | 0.7 (silica gel; toluene/ethyl acetate/glacial acetic acid = 50:45:5) |
| mass spectrum: | $(M - H)^- = 316$ |
| | $(M + Na)^+ = 340$ |

EXAMPLE 184

Trans-3-(naphth-2-yl)-but-2-enoic acid-N-(2-carboxy-5-hydroxymethyl-phenyl)-amide Prepared analogously to Example 2 from trans-3-(naphth-2-yl)-but-2-enoic acid-N-(2-methoxycarbonyl-5-hydroxymethyl-phenyl)-amide and potassium hydroxide solution in ethanol.

| Yield: | 33% of theory, $C_{22}H_{19}NO_4$ (361.39) |
|---|---|
| $R_f$ value: | 0.5 (silica gel; dichloromethane/ethanol = 9:1) |
| mass spectrum: | $(M - H)^- = 360$ |
| | $(M + Na)^+ = 384$ |

EXAMPLE 185

Trans-3-(naphth-2-yl)-but-2-enoic acid-N-[2-carboxy-4-(N-methyl-N-tert.butoxycarbonylamino)-phenyl]-amide Prepared analogously to Example 2 from trans-3-(naphth-2-yl)-but-2-enoic acid-N-[2-ethoxycarbonyl-4-(N-methyl- N-tert.butoxycarbonylamino)-phenyl]-amide and sodium hydroxide solution in methanol.

| | |
|---|---|
| Yield: | 77% of theory, $C_{27}H_{28}N_2O_5$ (460.53) |
| $R_f$ value: | 0.7 (silica gel; dichloromethane/ethanol = 9:1) |
| mass spectrum: | $(M - H)^- = 459$ |
| | $(M + Na)^+ = 483$ |

EXAMPLE 186

Trans-3-(naphth-2-yl)-but-2-enoic acid-N-[2-carboxy-4-(N-tert.butoxycarbonylamino)-phenyl]-amide Prepared analogously to Example 2 from trans-3-(naphth-2-yl)-but-2-enoic acid-N-[2-ethoxycarbonyl-4-(N-tert.butoxycarbonylamino)-phenyl]-amide and sodium hydroxide solution in methanol.

| | |
|---|---|
| Yield: | 96% of theory, $C_{26}H_{26}N_2O_5$ (446.50) |
| $R_f$ value: | 0.6 (silica gel; dichloromethane/ethanol = 9:1) |
| mass spectrum: | $(M - H)^- = 445$ |
| | $(M + Na)^+ = 469$ |

EXAMPLE 187

Trans-3-(naphth-2-yl)-but-2-enoic acid-N-[2-carboxy-4-(phenylaminocarbonylamino)-phenyl]-amide Prepared analogously to Example 2 from trans-3-(naphth-2-yl)-but-2-enoic acid-N-[2-ethoxycarbonyl-4-(phenylaminocarbonylamino)-phenyl]-amide and sodium hydroxide solution in methanol.

| | |
|---|---|
| Yield: | 97% of theory, $C_{28}H_{23}N_3O_4$ (465.51) |
| $R_f$ value: | 0.3 (silica gel; dichloromethane/ethanol = 9:1) |
| mass spectrum: | $(M - H)^- = 464$ |
| | $(M + Na)^+ = 488$ |

EXAMPLE 188

Trans-3-(naphth-2-yl)-but-2-enoic acid-N-[2-carboxy-4-(methylaminocarbonylamino)-phenyl]-amide Prepared analogously to Example 2 from trans-3-(naphth-2-yl)-but-2-enoic acid-N-[2-ethoxycarbonyl-4-(methylaminocarbonylamino)-phenyl]-amide and sodium hydroxide solution in methanol.

| | |
|---|---|
| Yield: | 91% of theory, $C_{23}H_{21}N_3O_4$ (403.44) |
| $R_f$ value: | 0.15 (silica gel; dichloromethane/ethanol = 9:1) |
| mass spectrum: | $(M - H)^- = 402$ |
| | $(M + Na)^+ = 426$ |

EXAMPLE 189

Trans-3-(naphth-2-yl)-but-2-enoic acid-N-(2-carboxy-5-trifluoromethyl-phenyl)-amide Prepared analogously to Example 31 from trans-(naphth-2-yl)-but-2-enoic acid chloride and 2-amino-5-trifluoromethyl-benzoic acid in tetrahydrofuran with the addition of triethylamine.

| | |
|---|---|
| Yield: | 13% of theory, $C_{22}H_{16}F_3NO_3$ (399.37) |
| $R_f$ value: | 0.2 (silica gel; dichloromethane/ethanol = 19:1) |
| mass spectrum: | $(M - H)^- = 398$ |

EXAMPLE 190

Trans-3-(naphth-2-yl)-but-2-enoic acid-N-[2-carboxy-4-(phenylethylaminocarbonylamino)-phenyl]-amide Prepared analogously to Example 2 from trans-3-(naphth-2-yl)-but-2-enoic acid-N-[2-ethoxycarbonyl-4-(phenylethylaminocarbonylamino)-phenyl]-amide and sodium hydroxide solution in methanol.

| | |
|---|---|
| Yield: | 95% of theory, $C_{30}H_{27}N_3O_4$ (493.56) |
| $R_f$ value: | 0.2 (silica gel; dichloromethane/ethanol = 9:1) |
| mass spectrum: | $(M - H)^- = 492$ |

EXAMPLE 191

Trans-3-(naphth-2-yl)-but-2-enoic acid-N-[2-carboxy-4-(4-phenoxy-phenylaminocarbonylamino)-phenyl]-amide Prepared analogously to Example 2 from trans-3-(naphth-2-yl)-but-2-enoic acid-N-[2-ethoxycarbonyl-4-(4-phenoxyphenylaminocarbonylamino)-phenyl]-amide and sodium hydroxide solution in methanol.

| | |
|---|---|
| Yield: | 98% of theory, $C_{34}H_{27}N_3O_5$ (557.61) |
| $R_f$ value: | 0.2 (silica gel; dichloromethane/ethanol = 9:1) |
| mass spectrum: | $(M - H)^- = 556$ |

EXAMPLE 192

Trans-3-(naphth-2-yl)-but-2-enoic acid-N-[2-carboxy-4-(benzylsulphonylamino)-phenyl]-amide Prepared analogously to Example 2 from trans-3-(naphth-2-yl)-but-2-enoic acid-N-[2-ethoxycarbonyl-4-(benzylsulphonylamino)-phenyl]-amide and sodium hydroxide solution in methanol.

| | |
|---|---|
| Yield: | 100% of theory, $C_{28}H_{24}N_2O_5S$ (500.58) |
| $R_f$ value: | 0.4 (silica gel; dichloromethane/ethanol = 9:1) |
| mass spectrum: | $(M - H)^- = 499$ |

EXAMPLE 193

Trans-3-(naphth-2-yl)-but-2-enoic acid-N-[2-carboxy-4-(pyridin-3-yl-aminocarbonylamino)-phenyl]-amide Prepared analogously to Example 2 from trans-3-(naphth-2-yl)-but-2-enoic acid-N-[2-ethoxycarbonyl-4-(pyridin-3- yl-aminocarbonylamino)-phenyl]-amide and sodium hydroxide solution in methanol.

| | |
|---|---|
| Yield: | 53% of theory, $C_{27}H_{22}N_4O_4$ (466.50) |
| $R_f$ value: | 0.25 (silica gel; dichloromethane/ethanol = 4:1) |
| mass spectrum: | $(M - H)^- = 465$ |

EXAMPLE 194

Trans-3-(naphth-2-yl)-but-2-enoic acid-N-[2-carboxy-5-(carboxymethyl-aminocarbonyl)-phenyl]-amide Prepared analogously to Example 2 from trans-3-(naphth-2-yl)-but-2-enoic acid-N-[2-methoxycarbonyl-5-(methoxycarbonylmethyl-aminocarbonyl)-phenyl]-amide and potassium hydroxide solution in ethanol.

| | |
|---|---|
| Yield: | 37% of theory, $C_{24}H_{20}N_2O_6$ (432.43) |
| $R_f$ value: | 0.4 (silica gel; dichloromethane/ethanol = 1:4) |
| mass spectrum: | $(M - H)^- = 431$ |

EXAMPLE 195

Trans-3-(naphth-2-yl)-but-2-enoic acid-N-[2-carboxy-5-(N-methyl-N-carboxymethyl-aminocarbonyl)-phenyl]-amide Prepared analogously to Example 2 from trans-3-(naphth-2-yl)-but-2-enoic acid-N-[2-methoxycarbonyl-5-(N-methyl-N-methoxycarbonylmethyl-aminocarbonyl)-phenyl]-amide and potassium hydroxide solution in ethanol.

| | |
|---|---|
| Yield: | 6% of theory, $C_{25}H_{22}N_2O_6$ (446.46) |
| $R_f$ value: | 0.35 (silica gel; dichloromethane/ethanol = 1:4) |
| mass spectrum: | $(M - H)^- = 445$ |

EXAMPLE 196

Trans-3-(naphth-2-yl)-but-2-enoic acid-N-[2-carboxy-5-(N-benzyl-aminocarbonyl)-phenyl]-amide Prepared analogously to Example 2 from trans-3-(naphth-2-yl)-but-2-enoic acid-N-[2-methoxycarbonyl-5-(N-benzyl-aminocarbonyl)-phenyl]-amide and potassium hydroxide solution in ethanol.

| | |
|---|---|
| Yield: | 100% of theory, $C_{29}H_{24}N_2O_4$ (464.52) |
| $R_f$ value: | 0.3 (silica gel; dichloromethane/ethanol = 9:1) |
| mass spectrum: | $(M - H)^- = 463$ $(M + Na)^+ = 487$ |

EXAMPLE 197

Trans-3-(naphth-2-yl)-but-2-enoic acid-N-[2-carboxy-5-(pyrrolidin-1-yl-aminocarbonyl)-phenyl]-amide Prepared analogously to Example 2 from trans-3-(naphth-2-yl)-but-2-enoic acid-N-[2-methoxycarbonyl-5-(pyrrolidin-1-yl-aminocarbonyl)-phenyl]-amide and potassium hydroxide solution in ethanol.

| | |
|---|---|
| Yield: | 58% of theory, $C_{26}H_{25}N_3O_4$ (443.50) |
| $R_f$ value: | 0.3 (silica gel; dichloromethane/ethanol = 4:1) |
| mass spectrum: | $(M - H)^- = 442$ $(M + Na)^+ = 466$ |

EXAMPLE 198

Trans-3-(naphth-2-yl)-but-2-enoic acid-N-[2-carboxy-5-(2-aminoethyl-aminocarbonyl)-phenyl]-amide Prepared analogously to Example 2 from trans-3-(naphth-2-yl)-but-2-enoic acid-N-[2-methoxycarbonyl-5-(2-aminoethyl-aminocarbonyl)-phenyl]-amide and potassium hydroxide solution in ethanol.

| | |
|---|---|
| Yield: | 58% of theory, $C_{24}H_{23}N_3O_4$ (417.46) |
| $R_f$ value: | 0.15 (silica gel; dichloromethane/ethanol/ammonia = 50:45:5) |
| mass spectrum: | $(M - H)^- = 416$ $(M + Na)^+ = 440$ |

EXAMPLE 199

Trans-3-(naphth-2-yl)-but-2-enoic acid-N-[2-carboxy-5-(2-tert.butoxycarbonylaminoethyl-aminocarbonyl)-phenyl]-amide 60 mg (0.27 mmol) of di-tert.butyldicarbonate are added to a solution of 0.1 g (0.24 mmol) of trans-3-(naphth-2-yl)-but-2-enoic acid-N-[2-carboxy-5-(2-aminoethyl-aminocarbonyl)-phenyl]-amide, 0.25 ml of 1 molar sodium hydroxide solution and 1 ml of tetrahydrofuran and stirred for 2 hours. The tetrahydrofuran is distilled off in vacuo. The residue is diluted with water, acidified with citric acid and extracted with ethyl acetate. The combined organic extracts are dried and evaporated down.

| | |
|---|---|
| Yield: | 64% of theory, $C_{29}H_{31}N_3O_6$ (517.58) |
| $R_f$ value: | 0.8 (silica gel; dichloromethane/ethanol/ammonia = 50:45:5) |
| mass spectrum: | $(M - H)^- = 516$ $(M + Na)^+ = 540$ |

EXAMPLE 200

Trans-3-(naphth-2-yl)-but-2-enoic acid-N-(2-carboxy-5-phenylaminocarbonyl-phenyl)-amide Prepared analogously to Example 2 from trans-3-(naphth-2-yl)-but-2-enoic acid-N-(2-methoxycarbonyl-5-phenylaminocarbonyl-phenyl)-amide and potassium hydroxide solution in ethanol.

EXAMPLE 201

Trans-3-(naphth-2-yl)-but-2-enoic acid-N-{2-carboxy-5-[N-(2-methoxy-1-methyl-ethyl)-aminocarbonyl]-phenyl}-amide Prepared analogously to Example 2 from trans-3-(naphth-2-yl)-but-2-enoic acid-N-{2-methoxycarbonyl-5-[N-(2-methoxy-1-methyl-ethyl)-aminocarbonyl]-phenyl}-amide and potassium hydroxide solution in ethanol.

| Yield: | 83% of theory, $C_{28}H_{22}N_2O_4$ (450.49) |
|---|---|
| $R_f$ value: | 0.15 (silica gel; dichloromethane/ethanol = 9:1) |
| mass spectrum: | $(M - H)^- = 449$ |

| Yield: | 69% of theory, $C_{26}H_{26}N_2O_5$ (446.50) |
|---|---|
| $R_f$ value: | 0.15 (silica gel; dichloromethane/ethanol = 9:1) |
| mass spectrum: | $(M - H)^- = 445$ |

EXAMPLE 202

Trans-3-(naphth-2-yl)-but-2-enoic acid-N-[2-carboxy-5-(N-piperidin-1-yl-aminocarbonyl)-phenyl]-amide Prepared analogously to Example 2 from trans-3-(naphth-2-yl)-but-2-enoic acid-N-[2-methoxycarbonyl-5-(N-piperidin-1-yl-aminocarbonyl)-phenyl]-amide and potassium hydroxide solution in ethanol.

| Yield: | 51% of theory, $C_{27}H_{27}N_3O_4$ (457.53) |
|---|---|
| $R_f$ value: | 0.2 (silica gel; toluene/ethyl acetate/glacial acetic acid = 50:45:5) |
| mass spectrum: | $(M - H)^- = 456$ |
| | $M^+ = 457$ |

EXAMPLE 203

Trans-3-(naphth-2-yl)-but-2-enoic acid-N-[2-carboxy-5-(N-cyclopentyl-aminocarbonyl)-phenyl]-amide Prepared analogously to Example 2 from trans-3-(naphth-2-yl)-but-2-enoic acid-N-[2-methoxycarbonyl-5-(N-cyclopentyl-aminocarbonyl)-phenyl]-amide and potassium hydroxide solution in ethanol.

| Yield: | 58% of theory, $C_{27}H_{26}N_2O_4$ (442.52) |
|---|---|
| $R_f$ value: | 0.6 (silica gel; toluene/ethyl acetate/glacial acetic acid = 50:45:5) |
| mass spectrum: | $(M - H)^- = 441$ |
| | $M^+ = 457$ |

EXAMPLE 204

Trans-3-(naphth-2-yl)-but-2-enoic acid-N-[2-carboxy-5-(N-cyclohexyl-aminocarbonyl)-phenyl]-amide Prepared analogously to Example 2 from trans-3-(naphth-2-yl)-but-2-enoic acid-N-[2-methoxycarbonyl-5-(N-cyclohexyl-aminocarbonyl)-phenyl]-amide and potassium hydroxide solution in ethanol.

| Yield: | 81% of theory, $C_{28}H_{28}N_2O_4$ (456.54) |
|---|---|
| $R_f$ value: | 0.42 (silica gel; dichloromethane/ethanol = 4:1) |
| mass spectrum: | $(M - H)^- = 455$ |

EXAMPLE 205

Trans-3-(naphth-2-yl)-but-2-enoic acid-N-[2-carboxy-5-(N-cyclopropyl-aminocarbonyl)-phenyl]-amide Prepared analogously to Example 2 from trans-3-(naphth-2-yl)-but-2-enoic acid-N-[2-methoxycarbonyl-5-(N-cyclopropyl-aminocarbonyl)-phenyl]-amide and potassium hydroxide solution in ethanol.

| Yield: | 59% of theory, $C_{25}H_{22}N_2O_4$ (414.46) |
|---|---|
| $R_f$ value: | 0.35 (silica gel; dichloromethane/ethanol = 4:1) |
| mass spectrum: | $(M - H)^- = 413$ |

EXAMPLE 206

Trans-3-(naphth-2-yl)-but-2-enoic acid-N-{2-carboxy-5-[N-(2,2,2-trifluorethyl)-aminocarbonyl]-phenyl}-amide Prepared analogously to Example 2 from trans-3-(naphth-2-yl)-but-2-enoic acid-N-{2-methoxycarbonyl-5-[N-(2,2,2-trifluorethyl)-aminocarbonyl]-phenyl}-amide and potassium hydroxide solution in ethanol.

| Yield: | 65% of theory, $C_{24}H_{19}F_3N_2O_4$ (456.42) |
|---|---|
| $R_f$ value: | 0.35 (silica gel; dichloromethane/ethanol = 4:1) |
| mass spectrum: | $(M - H)^- = 455$ |

EXAMPLE 207

Trans-3-(naphth-2-yl)-but-2-enoic acid-N-{2-carboxy-5-[N-(2-dimethylaminoethyl)-aminocarbonyl]-phenyl}-amide Prepared analogously to Example 2 from trans-3-(naphth-2-yl)-but-2-enoic acid-N-{2-methoxycarbonyl-5-[N-(2-dimethylaminoethyl)-aminocarbonyl]-phenyl}-amide and potassium hydroxide solution in ethanol.

| Yield: | 37% of theory, $C_{26}H_{27}N_3O_4$ (445.52) |
|---|---|
| $R_f$ value: | 0.1 (silica gel; dichloromethane/ethanol = 4:1) |
| mass spectrum: | $(M - H)^- = 444$ |

EXAMPLE 208

Trans-3-(naphth-2-yl)-but-2-enoic acid-N-{2-carboxy-5-[N-(3-dimethylaminopropyl)-aminocarbonyl]-phenyl}-amide Prepared analogously to Example 2 from trans-3-(naphth-2-yl)-but-2-enoic acid-N-{2-methoxycarbonyl-5-[N-(3- dimethylaminopropyl)-aminocarbonyl]-phenyl}-amide and potassium hydroxide solution in ethanol.

| Yield: | 29% of theory, $C_{27}H_{29}N_3O_4$ (459.55) |
|---|---|
| $R_f$ value: | 0.1 (silica gel; dichloromethane/ethanol = 4:1) |
| mass spectrum: | $(M - H)^- = 458$ |

EXAMPLE 209

Trans-3-(naphth-2-yl)-but-2-enoic acid-N-{2-carboxy-5-[N-(2-methoxyethyl)-aminocarbonyl]-phenyl}-amide Prepared analogously to Example 2 from trans-3-(naphth-2-yl)-but-2-enoic acid-N-{2-methoxycarbonyl-5-[N-(2-methoxyethyl)-aminocarbonyl]-phenyl}-amide and potassium hydroxide solution in ethanol.

| Yield: | 71% of theory, $C_{25}H_{24}N_2O_5$ (432.48) |
|---|---|
| $R_f$ value: | 0.35 (silica gel; dichloromethane/ethanol = 4:1) |
| mass spectrum: | $(M - H)^- = 431$ |

EXAMPLE 210

Trans-3-(naphth-2-yl)-but-2-enoic acid-N-[2-carboxy-5-(N-morpholin-4-yl-aminocarbonyl)-phenyl]-amide Prepared analogously to Example 2 from trans-3-(naphth-2-yl)-but-2-enoic acid-N-[2-methoxycarbonyl-5-(N-morpholin-4-yl-aminocarbonyl)-phenyl]-amide and potassium hydroxide solution in ethanol.

| Yield: | 69% of theory, $C_{26}H_{25}N_3O_5$ (459.50) |
|---|---|
| $R_f$ value: | 0.2 (silica gel; dichloromethane/ethanol = 4:1) |
| mass spectrum: | $(M - H)^- = 458$ |
| | $(M + Na)^+ = 482$ |

EXAMPLE 211

Trans-3-(naphth-2-yl)-but-2-enoic acid-N-[2-carboxy-5-(N-cyclobutyl-aminocarbonyl)-phenyl]-amide Prepared analogously to Example 2 from trans-3-(naphth-2-yl)-but-2-enoic acid-N-[2-methoxycarbonyl-5-(N-cyclobutyl-aminocarbonyl)-phenyl]-amide and potassium hydroxide solution in ethanol.

| Yield: | 87% of theory, $C_{26}H_{24}N_2O_4$ (428.49) |
|---|---|
| $R_f$ value: | 0.47 (silica gel; dichloromethane/ethanol = 4:1) |
| mass spectrum: | $(M - H)^- = 427$ |

EXAMPLE 212

Trans-3-(naphth-2-yl)-but-2-enoic acid-N-{2-carboxy-5-[N-(4-methylpiperazin-1-yl)-aminocarbonyl]-phenyl}-amide Prepared analogously to Example 2 from trans-3-(naphth-2-yl)-but-2-enoic acid-N-{2-methoxycarbonyl-5-[N-(4-methylpiperazin-1-yl)-aminocarbonyl]-phenyl}-amide and potassium hydroxide solution in ethanol.

| Yield: | 36% of theory, $C_{27}H_{28}N_4O_4$ (472.55) |
|---|---|
| $R_f$ value: | 0.3 (silica gel; dichloromethane/ethanol = 3:7) |
| mass spectrum: | $(M - H)^- = 471$ |
| | $(M + Na)^+ = 495$ |
| | $(M + H)^+ = 473$ |

EXAMPLE 213

Trans-3-(naphth-2-yl)-but-2-enoic acid-N-[2-carboxy-5-(2-methyl-hydrazino-carbonyl)-phenyl]-amide Prepared analogously to Example 2 from trans-3-(naphth-2-yl)-but-2-enoic acid-N-[2-methoxycarbonyl-5-(2-methylhydrazino-carbonyl)-phenyl]-amide and lithium hydroxide in tetrahydrofuran/water.

| Yield: | 62% of theory, $C_{23}H_{21}N_3O_4$ (403.44) |
|---|---|
| mass spectrum: | $(M - H)^- = 402$ |
| | $(M + Na)^+ = 426$ |

EXAMPLE 214

Trans-3-(naphth-2-yl)-but-2-enoic acid-N-[2-carboxy-5-(2-benoyl-hydrazino-carbonyl)-phenyl]-amide Prepared analogously to Example 2 from trans-3-(naphth-2-yl)-but-2-enoic acid-N-[2-methoxycarbonyl-5-(2-benzoylhydrazino-carbonyl)-phenyl]-amide and potassium hydroxide solution in ethanol.

| Yield: | 21% of theory, $C_{29}H_{23}N_3O_5$ (493.52) |
|---|---|
| $R_f$ value: | 0.55 (silica gel; dichloromethane/ethanol = 3:1) |
| mass spectrum: | $(M - H)^- = 492$ |

EXAMPLE 215

Trans-3-(naphth-2-yl)-but-2-enoic acid-N-[2-carboxy-5-(2,2-dimethyl-hydrazinocarbonyl)-phenyl]-amide Prepared analogously to Example 2 from trans-3-(naphth-2-yl)-but-2-enoic acid-N-[2-methoxycarbonyl-5-(N,N-dimethyl-hydrazino-carbonyl)-phenyl]-amide and lithium hydroxide in tetrahydrofuran/water.

| Yield: | 77% of theory, $C_{24}H_{23}N_3O_4$ (417.46) |
|---|---|
| $R_f$ value: | 0.2 (silica gel; dichloromethane/ethanol = 4:1) |
| mass spectrum: | $(M - H)^- = 416$ |
| | $(M + Na)^+ = 440$ |

EXAMPLE 216

Trans-3-(naphth-2-yl)-but-2-enoic acid-N-[2-carboxy-5-(1,2-dimethylhydrazino-carbonyl)-phenyl]-amide Prepared analogously to Example 2 from trans-3-(naphth-2-yl)-but-2-enoic acid-N-[2-methoxycarbonyl-5-(1,2- dimethylhydrazino-carbonyl)-phenyl]-amide and lithium hydroxide in tetrahydrofuran/water.

| | |
|---|---|
| Yield: | 77% of theory, $C_{24}H_{23}N_3O_4$ (417.46) |
| $R_f$ value: | 0.3 (silica gel; dichloromethane/ethanol = 4:1) |
| mass spectrum: | $(M - H)^- = 416$ |
| | $(M + Na)^+ = 440$ |

EXAMPLE 217

Trans-3-(naphth-2-yl)-but-2-enoic acid-N-[2-carboxy-5-(N-prop-2-ynyl-aminocarbonyl)-phenyl]-amide Prepared analogously to Example 2 from trans-3-(naphth-2-yl)-but-2-enoic acid-N-[2-methoxycarbonyl-5-(N-prop-2-ynyl-aminocarbonyl)-phenyl]-amide and lithium hydroxide in methanol/water.

| | |
|---|---|
| Yield: | 65% of theory, $C_{25}H_{20}N_2O_4$ (412.44) |
| $R_f$ value: | 0.46 (silica gel; dichloromethane/ethanol = 3:1) |
| mass spectrum: | $(M - H)^- = 411$ |
| | $(M + Na)^+ = 435$ |

EXAMPLE 218

Trans-3-(naphth-2-yl)-but-2-enoic acid-N-[2-carboxy-5-(N-isobutylaminocarbonyl)-phenyl]-amide Prepared analogously to Example 2 from trans-3-(naphth-2-yl)-but-2-enoic acid-N-[2-methoxycarbonyl-5-(N-isobutylaminocarbonyl)-phenyl]-amide and lithium hydroxide in methanol/water.

| | |
|---|---|
| Yield: | 58% of theory, $C_{26}H_{26}N_2O_4$ (430.50) |
| $R_f$ value: | 0.41 (silica gel; dichloromethane/ethanol = 3:1) |
| mass spectrum: | $(M - H)^- = 429$ |
| | $(M + Na)^+ = 453$ |

EXAMPLE 219

Trans-3-(naphth-2-yl)-but-2-enoic acid-N-[2-carboxy-5-(N-(pyridin-3-yl-methyl)-aminocarbonyl)-phenyl]-amide Prepared analogously to Example 2 from trans-3-(naphth-2-yl)-but-2-enoic acid-N-[2-methoxycarbonyl-5-(N-(pyridin-3-yl-methyl)-aminocarbonyl)-phenyl]-amide and lithium hydroxide in methanol/water.

| | |
|---|---|
| Yield: | 39% of theory, $C_{28}H_{23}N_3O_4$ (465.51) |
| $R_f$ value: | 0.21 (silica gel; dichloromethane/ethanol = 3:1) |
| mass spectrum: | $(M - H)^- = 464$ |

EXAMPLE 220

Trans-3-(naphth-2-yl)-but-2-enoic acid-N-[2-carboxy-5-(N-(2-methylthio-ethyl)-aminocarbonyl)-phenyl]-amide Prepared analogously to Example 2 from trans-3-(naphth-2-yl)-but-2-enoic acid-N-[2-methoxycarbonyl-5-(N-(2-methylthio-ethyl)-aminocarbonyl)-phenyl]-amide and lithium hydroxide in methanol/water.

| | |
|---|---|
| Yield: | 45% of theory, $C_{25}H_{24}N_2O_4S$ (448.54) |
| $R_f$ value: | 0.41 (silica gel; dichloromethane/ethanol = 3:1) |
| mass spectrum | $(M - H)^- = 447$ |

EXAMPLE 221

Trans-3-(naphth-2-yl)-but-2-enoic acid-N-[2-carboxy-5-(N-(2-hydroxy-ethyl)-aminocarbonyl)-phenyl]-amide Prepared analogously to Example 2 from trans-3-(naphth-2-yl)-but-2-enoic acid-N-[2-methoxycarbonyl-5-(N-(2-hydroxy-ethyl)-aminocarbonyl)-phenyl]-amide and lithium hydroxide in methanol/water.

| | |
|---|---|
| Yield: | 68% of theory, $C_{24}H_{22}N_2O_5$ (418.45) |
| $R_f$ value: | 0.20 (silica gel; dichloromethane/ethanol = 3:1) |
| mass spectrum: | $(M - H)^- = 417$ |

EXAMPLE 222

Trans-3-(naphth-2-yl)-but-2-enoic acid-N-[2-carboxy-5-(2-tert.-butoxycarbonylhydrazino-carbonyl)-phenyl]-amide Prepared analogously to Example 2 from trans-3-(naphth-2-yl)-but-2-enoic acid-N-[2-methoxycarbonyl-5-(2-tert.butoxycarbonylhydrazino-carbonyl)-phenyl]-amide and lithium hydroxide in methanol/water.

| | |
|---|---|
| Yield: | 48% of theory, $C_{27}H_{27}N_3O_6$ (489.53) |
| $R_f$ value: | 0.38 (silica gel; dichloromethane/ethanol = 3:1) |
| mass spectrum: | $(M - H)^- = 488$ |

EXAMPLE 223

Trans-3-(naphth-2-yl)-but-2-enoic acid-N-[2-carboxy-5-(2,5-dihydropyrrol-1-yl-carbonyl)-phenyl]-amide Prepared analogously to Example 2 from trans-3-(naphth-2-yl)-but-2-enoic acid-N-[2-methoxycarbonyl-5-(2,5-dihydropyrrol-1-yl-carbonyl)-phenyl]-amide and lithium hydroxide in methanol/water.

| | |
|---|---|
| Yield: | 73% of theory, $C_{26}H_{22}N_2O_4$ (426.47) |
| $R_f$ value: | 0.48 (silica gel; dichloromethane/ethanol = 3:1) |
| mass spectrum: | $(M - H)^- = 425$ |
| | $(M + Na)^+ = 449$ |

EXAMPLE 224

Trans-3-(naphth-2-yl)-but-2-enoic acid-N-[2-carboxy-5-(allylaminocarbonyl)-phenyl]-amide Prepared analogously to Example 2 from trans-2-yl)-but-2-enoic acid-N-[2-carboxy-5-

(allylaminocarbonyl)-phenyl]-amide and lithium hydroxide in methanol/water.

| | |
|---|---|
| Yield: | 68% of theory, $C_{25}H_{22}N_2O_4$ (414.46) |
| $R_f$ value: | 0.44 (silica gel; dichloromethane/ethanol = 3:1) |
| mass spectrum: | $(M - H)^- = 413$ |
| | $(M + Na)^+ = 437$ |

EXAMPLE 225

Trans-3-(naphth-2-yl)-but-2-enoic acid-N-[2-carboxy-5-(3-hydroxy-1-propynyl)-phenyl]-amide Prepared analogously to Example 2 from trans-3-(naphth-2-yl)-but-2-enoic acid-N-[2-methoxycarbonyl-5-(3-hydroxy-1-propynyl)-phenyl]-amide and lithium hydroxide in tetrahydrofuran/water.

| | |
|---|---|
| Yield: | 27% of theory, $C_{24}H_{19}NO_4$ (385.42) |
| $R_f$ value: | 0.3 (silica gel; dichloromethane/ethanol = 9:1) |
| mass spectrum: | $(M - H)^- = 384$ |

EXAMPLE 226

Trans-3-(naphth-2-yl)-but-2-enoic acid-N-[2-carboxy-5-benzylamino-phenyl]-amide

Prepared analogously to Example 2 from trans-3-(naphth-2-yl)-but-2-enoic acid-N-[2-methoxycarbonyl-5-benzylamino-phenyl]-amide and potassium hydroxide solution in methanol.

| | |
|---|---|
| Yield: | 87% of theory, $C_{28}H_{24}N_2O$ (436.51) |
| $R_f$ value: | 0.25 (silica gel; dichloromethane/ethanol = 49:1) |
| mass spectrum: | $(M - H)^- = 435$ |

EXAMPLE 227

Trans-3-(naphth-2-yl)-but-2-enoic acid-N-[2-carboxy-5-(N-(2-dimethylamino-ethyl)-amino)-phenyl]-amide Prepared analogously to Example 2 from trans-3-(naphth-2-yl)-but-2-enoic acid-N-[2-methoxycarbonyl-5-(N-(2-dimethylaminoethyl)-amino)-phenyl]-amide and lithium hydroxide in tetrahydrofuran/water.

| | |
|---|---|
| Yield: | 86% of theory, $C_{25}H_{27}N_3O_3$ (417.51) |
| $R_f$ value: | 0.15 (silica gel; dichloromethane/ethanol = 1:1) |
| mass spectrum: | $(M - H)^- = 416$ |

EXAMPLE 228

Trans-3-(naphth-2-yl)-but-2-enoic acid-N-(6-carboxy-quinolin-5-yl)-amide

Prepared analogously to Example 31 from trans-(naphth-2-yl)-but-2-enoic acid chloride and 5-amino-6-carboxyquinoline in dimethylformamide with the addition of triethylamine and subsequent reaction analogously to Example 2 with lithium hydroxide in methanol/water.

| | |
|---|---|
| Yield: | 17% of theory, $C_{24}H_{18}N_2O_3$ (382.42) |
| $R_f$ value: | 0.7 (silica gel; dichloromethane/ethanol = 9:1) |
| mass spectrum: | $(M - H)^- = 381$ |

EXAMPLE 229

Trans-3-(naphth-2-yl)-but-2-enoic acid-N-(4-carboxy-3-biphenyl)-amide

Prepared analogously to Example 31 from trans-(naphth-2-yl)-but-2-enoic acid chloride and 3-amino-biphenyl-4-carboxylic acid in pyridine with the addition of 2-dimethylaminopyridine.

| | |
|---|---|
| Yield: | 29% of theory, $C_{27}H_{21}NO_3$ (407.47) |
| $R_f$ value: | 0.7 (silica gel; dichloromethane/ethanol = 9:1) |
| mass spectrum: | $(M - H)^- = 406$ |

EXAMPLE 230

Trans-3-(naphth-2-yl)-but-2-enoic acid-N-(2-carboxy-5-isopropylaminocarbonylamino)-amide Prepared analogously to Example 2 from trans-3-(naphth-2-yl)-but-2-enoic acid-N-(2-methoxycarbonyl-5-isopropylaminocarbonylamino)-amide and potassium hydroxide solution in ethanol.

| | |
|---|---|
| Yield: | 31% of theory, $C_{25}H_{25}N_3O_4$ (431.49) |
| mass spectrum: | $(M - H)^- = 430$ |

EXAMPLE 231

Trans-3-(naphth-2-yl)-but-2-enoic acid-N-[2-carboxy-5-(N-(pyridin-2-yl-methyl)-aminocarbonyl)-phenyl]-amide Prepared analogously to Example 2 from trans-3-(naphth-2-yl)-but-2-enoic acid-N-[2-methoxycarbonyl-5-(N-(pyridin-2-yl-methyl)-aminocarbonyl)-phenyl]-amide and lithium hydroxide in tetrahydrofuran/water.

| | |
|---|---|
| Yield: | 34% of theory, $C_{28}H_{23}N_3O_4$ (465.51) |
| $R_f$ value: | 0.35 (silica gel; dichloromethane/ethanol = 3:1) |
| mass spectrum: | $(M - H)^- = 464$ |

EXAMPLE 232

Trans-3-(naphth-2-yl)-but-2-enoic acid-N-[2-carboxy-5-(N-(pyridin-4-yl-methyl)-aminocarbonyl)-phenyl]-amide Prepared analogously to Example 2 from trans-3-(naphth-2-yl)-but-2-enoic acid-N-[2-methoxycarbonyl-5-(N-

(pyridin-4-yl-methyl)-aminocarbonyl)-phenyl]-amide and lithium hydroxide in tetrahydrofuran/water.

| | |
|---|---|
| Yield: | 31% of theory, |
| | $C_{28}H_{23}N_3O_4$ (465.51) |
| $R_f$ value: | 0.2 (silica gel; dichloromethane/ethanol = 3:1) |
| mass spectrum: | $(M - H)^- = 464$ |

EXAMPLE 233

Trans-3-(naphth-2-yl)-but-2-enoic acid-N-{2-carboxy-5-[N-(pyridin-3-yl-methyl)-N-methyl-amino)-carbonyl]-phenyl}-amide Prepared analogously to Example 2 from trans-3-(naphth-2-yl)-but-2-enoic acid-N-{2-methoxycarbonyl-5-[N-(pyridin-3-yl-methyl)-N-methyl-amino)-carbonyl]-phenyl}-amide and lithium hydroxide in tetrahydrofuran/water.

| | |
|---|---|
| Yield: | 51% of theory, |
| | $C_{29}H_{25}N_3O_4$ (479.54) |
| $R_f$ value: | 0.3 (silica gel; dichloromethane/ethanol = 3:1) |
| mass spectrum: | $(M - H)^- = 478$ |

EXAMPLE 234

Trans-3-(naphth-2-yl)-but-2-enoic acid-N-[2-carboxy-5-(N-(pyridin-4-yl)-aminocarbonyl)-phenyl]-amide Prepared analogously to Example 2 from trans-3-(naphth-2-yl)-but-2-enoic acid-N-[2-methoxycarbonyl-5-(N-(pyridin-4-yl)-aminocarbonyl)-phenyl]-amide and lithium hydroxide in tetrahydrofuran/water.

| | |
|---|---|
| Yield: | 44% of theory, |
| | $C_{27}H_{21}N_3O_4$ (451.48) |
| $R_f$ value: | 0.2 (silica gel; dichloromethane/ethanol = 3:1) |
| mass spectrum: | $(M - H)^- = 450$ |
| | $M^+ = 451$ |

EXAMPLE 235

Trans-3-(naphth-2-yl)-but-2-enoic acid-N-{2-carboxy-5-[(1-methyl-piperidin-4-yl-methyl)-aminocarbonyl]-phenyl}-amide-hydrochloride Prepared analogously to Example 2 from trans-3-(naphth-2-yl)-but-2-enoic acid-N-{2-methoxycarbonyl-5-[(1-methyl-piperidin-4-yl-methyl)-aminocarbonyl]-phenyl}-amide and lithium hydroxide in tetrahydrofuran/water and subsequent treatment with HCl.

| | |
|---|---|
| Yield: | 52% of theory, |
| | $C_{29}H_{31}N_3O_4 \times HCl$ (485.58/522.05) |
| $R_f$ value: | 0.2 (Reversed Phase RP 8; methanol/5% sodium chloride = 6:4) |
| mass spectrum: | $(M - H)^- = 484$ |
| | $(M + H)^+ = 486$ |

EXAMPLE 236

Trans-3-(naphth-2-yl)-but-2-enoic acid-N-{2-carboxy-5-[(1-tert.butoxycarbonyl-piperidin-4-yl-methyl)-aminocarbonyl]-phenyl}-amide Prepared analogously to Example 2 from trans-3-(naphth-2-yl)-but-2-enoic acid-N-{2-methoxycarbonyl-5-[(1-tert.butoxycarbonyl-piperidin-4-yl-methyl)-aminocarbonyl]-phenyl}-amide and lithium hydroxide in tetrahydrofuran/water.

| | |
|---|---|
| Yield: | 39% of theory, |
| | $C_{33}H_{37}N_3O_6$ (571.67) |
| $R_f$ value: | 0.5 (silica gel: dichloromethane/ethanol = 3:1) |
| mass spectrum: | $(M - H)^- = 570$ |

EXAMPLE 237

Trans-3-(naphth-2-yl)-but-2-enoic acid-N-{2-carboxy-5-[(1-aza-bicyclo[2.2.2]oct-3-ylamino)-carbonyl]-phenyl}-amide Prepared analogously to Example 2 from trans-3-(naphth-2-yl)-but-2-enoic acid-N-{2-methoxycarbonyl-5-[(1-aza-bicyclo[2.2.2]oct-3-ylamino)-carbonyl]-phenyl}-amide and lithium hydroxide in tetrahydrofuran/water.

| | |
|---|---|
| Yield: | 31% of theory, |
| | $C_{29}H_{29}N_3O_4$ (483.57) |
| $R_f$ value: | 0.2 (Reversed Phase RP 8; methanol/5% sodium chloride = 6:4) |
| mass spectrum: | $(M + H)^+ = 484$ |

EXAMPLE 238

Trans-3-(naphth-2-yl)-but-2-enoic acid-N-[2-carboxy-5-(2-carboxy-ethyl-aminocarbonyl)-phenyl]-amide Prepared analogously to Example 2 from trans-3-(naphth-2-yl)-but-2-enoic acid-N-[2-methoxycarbonyl-5-(2-methoxycarbonyl-ethyl-aminocarbonyl)-phenyl]-amide and lithium hydroxide in tetrahydrofuran/water.

| | |
|---|---|
| Yield: | 80% of theory, |
| | $C_{25}H_{22}N_2O_6$ (446.46) |
| $R_f$ value: | 0.2 (silica gel; dichloromethane/ethanol = 3:1) |
| mass spectrum: | $(M - H)^- = 445$ |

EXAMPLE 239

Trans-3-(naphth-2-yl)-but-2-enoic acid-N-{2-carboxy-5-[(1H-imidazol-4-ylmethyl)-aminocarbonyl]-phenyl}-amide Prepared analogously to Example 2 from trans-3-(naphth-2-yl)-but-2-enoic acid-N-{2-methoxycarbonyl-5-[(1H-imidazol-4-ylmethyl)-aminocarbonyl]-phenyl}-amide and lithium hydroxide in tetrahydrofuran/water.

| | |
|---|---|
| Yield: | 26% of theory, |
| | $C_{26}H_{22}N_4O_4$ (454.48) |
| $R_f$ value: | 0.7 (silica gel; ethyl acetate/ethanol/ammonia = 10:9:1) |
| mass spectrum: | $(M - H)^- = 453$ |

EXAMPLE 240

Trans-3-(naphth-2-yl)-but-2-enoic acid-N-{2-carboxy-5-[N-(2-acetylaminoethyl)-aminocarbonyl]-phenyl}-amide Prepared analogously to Example 2 from trans-3-(naphth-2-yl)-but-2-enoic acid-N-{2-methoxycarbonyl-5-[N-(2- acetylaminoethyl)-aminocarbonyl]-phenyl}-amide and lithium hydroxide in tetrahydrofuran/water.

| | |
|---|---|
| Yield: | 100% of theory, $C_{26}H_{25}N_3O_5$ (459.50) |
| $R_f$ value: | 0.2 (silica gel; dichloromethane/ethanol = 3:1) |
| mass spectrum: | $(M - H)^- = 458$ |

EXAMPLE 241

Trans-3-(naphth-2-yl)-but-2-enoic acid-N-{2-carboxy-5-[N-(piperidin-4-yl-methyl)-aminocarbonyl]-phenyl}-amide-trifluoroacetate Prepared analogously to Example 163 from trans-3-(naphth-2-yl)-but-2-enoic acid-N-{2-carboxy-5-[N-(1-tert.butoxycarbonyl-piperidin-4-yl-methyl)-aminocarbonyl]-phenyl}-amide and trifluoroacetic acid in dichloromethane.

| | |
|---|---|
| Yield: | 98% of theory, $C_{28}H_{29}N_3O_4 \times CF_3COOH$ (471.58/585.58) |
| $R_f$ value: | 0.3 (silica gel; dichloromethane/ethanol = 4:1) |
| mass spectrum: | $(M - H)^- = 470$ |
| | $(M + H)^+ = 472$ |

EXAMPLE 242

Trans-3-(naphth-2-yl)-but-2-enoic acid-N-(2-carboxy-5-pyrrolidino-phenyl)-amide

Prepared analogously to Example 2 from trans-3-(naphth-2-yl)-but-2-enoic acid-N-(2-methoxycarbonyl-5-pyrrolidino-phenyl)-amide and potassium hydroxide solution in tetrahydrofuran.

| | |
|---|---|
| Yield: | 41% of theory, $C_{25}H_{24}N_2O_3$ (400.48) |
| $R_f$ value: | 0.3 (silica gel; dichloromethane/ethanol = 49:1) |
| mass spectrum: | $(M - H)^- = 399$ |

EXAMPLE 243

Trans-3-(naphth-2-yl)-but-2-enoic acid-N-(2-carboxy-5-isopropylamino-phenyl)-amide Prepared analogously to Example 2 from trans-3-(naphth-2-yl)-but-2-enoic acid-N-(2-methoxycarbonyl-5-isopropylamino-phenyl)-amide and potassium hydroxide solution in tetrahydrofuran.

| | |
|---|---|
| Yield: | 83% of theory, $C_{24}H_{24}N_2O_3$ (388.47) |
| $R_f$ value: | 0.4 (silica gel; dichloromethane/ethanol = 19:1) |
| mass spectrum: | $(M - H)^- = 387$ |
| | $M^+ = 388$ |

EXAMPLE 244

Trans-3-(naphth-2-yl)-but-2-enoic acid-N-(2-carboxy-5-propylamino-phenyl)-amide

Prepared analogously to Example 2 from trans-3-(naphth-2-yl)-but-2-enoic acid-N-(2-methoxycarbonyl-5-propylamino-phenyl)-amide and potassium hydroxide solution in methanol.

| | |
|---|---|
| Yield: | 74% of theory, $C_{24}H_{24}N_2O_3$ (388.47) |
| $R_f$ value: | 0.4 (silica gel; dichloromethane/ethanol = 19:1) |
| mass spectrum: | $(M - H)^- = 387$ |

EXAMPLE 245

Trans-3-(naphth-2-yl)-but-2-enoic acid-N-(2-carboxy-5-morpholino-phenyl)-amide

Prepared analogously to Example 2 from trans-3-(naphth-2-yl)-but-2-enoic acid-N-(2-methoxycarbonyl-5-morpholino-phenyl)-amide and potassium hydroxide solution in methanol.

| | |
|---|---|
| Yield: | 71% of theory, $C_{25}H_{24}N_2O_3$ (416.48) |
| $R_f$ value: | 0.6 (silica gel; dichloromethane/ethanol = 9:1) |
| mass spectrum: | $(M - H)^- = 415$ |

EXAMPLE 246

Trans-3-(naphth-2-yl)-but-2-enoic acid-N-(2-carboxy-5-phenyl-amino-phenyl)-amide Prepared analogously to Example 2 from trans-3-(naphth-2-yl)-but-2-enoic acid-N-(2-methoxycarbonyl-5-phenylamino-phenyl)-amide and potassium hydroxide solution in methanol.

| | |
|---|---|
| Yield: | 97% of theory, $C_{27}H_{22}N_2O_3$ (422.49) |
| $R_f$ value: | 0.79 (silica gel; dichloromethane/ethanol = 9:1) |
| mass spectrum: | $(M - H)^- = 421$ |

EXAMPLE 247

Trans-3-(naphth-2-yl)-but-2-enoic acid-N-(2-carboxy-5-(3-di-methylamino-prop-1-ynyl)-phenyl)-amide Prepared analogously to Example 2 from trans-3-(naphth-2-yl)-but-2-enoic acid-N-(2-methoxycarbonyl-5-(3-dimethylamino-prop-1-ynyl)-phenyl)-amide and lithium hydroxide in a mixture of tetrahydrofuran and water.

| | |
|---|---|
| Yield: | 82% of theory, $C_{26}H_{24}N_2O_3$ (412.49) |
| $R_f$ value: | 0.22 (silica gel; dichloromethane/ethanol = 4:1) |
| mass spectrum: | $(M - H)^- = 411$ |
| | $(M + H)^+ = 413$ |
| | $M^+ = 412$ |

EXAMPLE 248

Trans-3-(isoquinolyl)-but-2-enoic acid-N-(2-carboxyphenyl)-amide

Prepared analogously to Example 2 from trans-3-(isoquinolyl)-but-2-enoic acid-N-(2-methoxycarbonyl-phenyl)-amide and lithium hydroxide in a mixture of tetrahydrofuran and water.

| Yield: | 69% of theory, |
| --- | --- |
| | $C_{20}H_{16}N_2O_3$ (332.36) |
| $R_f$ value: | 0.48 (silica gel; dichloromethane/ethanol = 9:1) |
| mass spectrum: | $(M - H)^- = 331$ |
| | $(M + H)^+ = 333$ |
| | $(M + Na)^+ = 355$ |

EXAMPLE 249
Tablets containing 50 mg of active substance

| Active substance | 50.0 mg |
| --- | --- |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

The active substance, $CaHPO_4$, lactose and corn starch are evenly moistened with an aqueous PVP solution. The mass is passed through a 2-mm screen, dried in a circulating air drier at 50° C. and screened again.

After the lubricant has been mixed in, the granules are compressed in a tablet-making machine.

EXAMPLE 250
Coated tablets containing 50 mg of active substance

| Active substance | 50.0 mg |
| --- | --- |
| Lysine | 25.0 mg |
| Lactose | 60.0 mg |
| Corn starch | 34.0 mg |
| Gelatine | 10.0 mg |
| Magnesium stearate | 1.0 mg |
| | 180.0 mg |

Preparation:

The active substance is mixed with the excipients and moistened with an aqueous gelatine solution. After screening and drying, the granules are mixed with magnesium stearate and compressed to form tablet cores.

The cores thus produced are covered with a coating by known methods. The coating suspension or solution may have colouring added to it.

EXAMPLE 251
Coated tablets containing 100 mg of active substance

| Active substance | 100.0 mg |
| --- | --- |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation:

The active substance is mixed with the excipients and moistened with an aqueous PVP solution. The moist mass is passed through a 1.5 mm screen and dried at 45° C. After drying, the mass is screened again and the magnesium stearate is added. This mixture is compressed to form tablet cores.

The cores thus produced are covered with a coating by known methods. The coating suspension or solution may have colouring added to it.

EXAMPLE 252
Capsules containing 250 mg of active substance

| Active substance | 250.0 mg |
| --- | --- |
| Corn starch | 68.5 mg |
| Magnesium stearate | 1.5 mg |
| | 320.0 mg |

Preparation:

Active substance and corn starch are mixed together and moistened with water. The moist mass is screened and dried. The dry granules are screened and mixed with magnesium stearate. The final mixture is packed into size 1 hard gelatine capsules.

What is claimed is:

1. A compound of the formula I

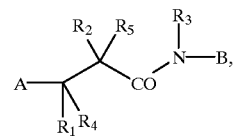

wherein:

$R_1$ denotes a hydrogen atom or a $C_{1-3}$-alkyl group, $R_2$ denotes a hydrogen atom, $R_4$ denotes a hydrogen atom, $R_4$ and $R_5$ together denote another carbon-carbon bond, A denotes a naphthyl group mono-or disubstituted by a fluorine, chlorine, bromine or iodine atom or by a $C_{1-6}$-alkyl, $C_{3-7}$-cycloalkyl or trifluoromethyl group, whilst the substituents may be identical or different, or a naphthyl group, and B denotes a phenylgroup, which is substituted by a carboxy group, whilst the above-mentioned phenyl group may additionally be substituted by a fluorine, chlorine or bromine atom, by a $C_{1-3}$-alkyl, hydroxy, $C_{1-3}$-alkoxy, $C_{1-3}$-alkylsulphonyloxy, pyrrolidino, piperidino, morpholino or N-($C_{1-3}$-alkyl)-piperazino group, by an n-$C_{2-3}$-alkoxy, $C_{2-3}$-alkenyl or $C_{2-3}$-alkynyl group substituted in the 2 or 3 position by a di-($C_{1-3}$-alkyl)-amino group, by an N-methyl-N-(n-$C_{2-3}$-alkyl)-amino group substituted in the 2 or 3 position by a di-($C_{1-3}$-alkyl)-amino group, by a di-($C_{1-3}$-alkyl)-amino group, by an imidazolyl or pyrazolyl group optionally substituted by a $C_{1-4}$-alkyl group, by a $C_{1-4}$-allylaminocarbonyl, N-(pyridinylmethyl)-aminocarbonyl, pyrrolidinoaminocarbonyl or piperidinoaminocarbonyl group and may additionally be substituted by another fluorine atom, by another $C_{1-3}$-alkyl or $C_{1-3}$-alkoxy group, or a physiologically acceptable salt thereof.

2. A compound of the formula I according to claim 1, wherein:

$R_1$ denotes a methyl group, $R_2$ denotes a hydrogen atom, $R_3$ denotes a hydrogen atom, $R_4$ and $R_5$ together denote another carbon-carbon bond, A denotes a naphthyl group, and B denotes a 2-carboxy-phenyl group, which may additionally be substituted in the phenyl nucleus by a fluorine, chlorine or bromine atom, by a $C_{1-3}$-alkyl, hydroxy, $C_{1-3}$-alkoxy, $C_{1-3}$-alkylsulphonyloxy or morpholino group, by an n-$C_{2-3}$-alkoxy group substituted in the 2 or 3 position by a di-($C_{1-3}$-alkyl)-amino group, by an N-methyl-N-(n-$C_{2-3}$-alkyl)-amino group substituted in the 2 or 3 position by a di-($C_{1-3}$-alkyl)-amino group, by an imidazolyl or pyrazolyl group optionally substituted by a $C_{1-4}$-alkyl group, by a $C_{1-4}$-alkylaminocarbonyl, N-(pyridinylmethyl)-aminocarbonyl, pyrrolidinoaminocarbonyl or piperidinoaminocarbonyl group and may additionally be substituted by another fluorine atom or by another methoxy group, or a physiologically acceptable salt thereof.

3. A compound selected from the group consisting of:

(a) trans-3-(naphth-2-yl)-but-2-enoic acid-N-(2-carboxy-phenyl)-amide, (b) trans-3-(naphth-2-yl)-but-2-enoic acid-N-(2-carboxy4,5-dimethoxy-phenyl)-amide, (c) trans-3-(naphth-2-yl)-but-2-enoic acid-N-(2-carboxy-4-fluoro-phenyl)-amide, (d) trans-3-(naphth-2-yl)-but-2-enoic acid-N-(2-carboxy-4,5-difluoro-phenyl)-amide, (e) trans-3-(naphth-2-yl)-but-2-enoic acid-N-(2-carboxy-5-fluoro-phenyl)-amide, (f) trans-3-(naphth-2-yl)-but-2-enoic acid-N-(2-carboxy-4-methoxy-5-methyl-phenyl)-amide, (g) trans-3-(naphth-2-yl)-but-2-enoic acid-N-[2-carboxy-4-(morpholin-4-yl)-phenyl]-amide, (h) trans-3-(naphth-2-yl)-but-2-enoic acid-N-(2-carboxy-4-dimethylamino-phenyl)-amide, (i) trans-3-(naphth-2-yl)-but-2-enoic acid-N-(2-carboxy-4-hydroxy-phenyl)-amide, (j) trans-3-(naphth-2-yl)-but-2-enoic acid-N-[2-carboxy-4-(imidazol-1-yl)-phenyl]-amide, (k) trans-3-(naphth-2-yl)-but-2-enoic acid-N-[(2-carboxy-4-(imidazol-1-yl)-5-fluoro-phenyl]-amide, (l) trans-3-(naphth-2-yl)-but-2-enoic acid-N-(2-carboxy-4-methanesulphonyloxy-phenyl)-amide, (m) trans-3-(naphth-2-yl)-but-2-enoic acid-N-[2-carboxy-4-(2-N,N-dimethylamino-ethyloxy)-phenyl]-amide, (n) trans-3-(naphth-2-yl)-but-2-enoic acid-N-(2-carboxy-6-methyl-phenyl)-amide, (o) trans-3-(naphth-2-yl)-but-2-enoic acid-N-(2-carboxy-6-fluoro-phenyl)-amide, (p) trans-3-(naphth-2-yl)-but-2-enoic acid-N-[2-carboxy-5-(propylaminocarbonyl)-phenyl]-amide, (q) trans-3-(naphth-2-yl)-but-2-enoic acid-N-[2-carboxy-5-(pyrrolidin-1-yl-aminocarbonyl)-phenyl]-amide, (r) trans-3-(naphth-2-yl)-but-2-enoic acid-N-[2-carboxy-5-(N-(pyridin-3-yl-methyl)-aminocarbonyl)-phenyl]-amide, and (s) trans-3-(naphth-2-yl)-but-2-enoic acid-N-(2-carboxy-6-chloro-phenyl)-amide or a physiologically acceptable salt thereof.

4. Trans-3-(naphth-2-yl)-but-2-enoic acid-N-(2-carboxy-phenyl)-amide or a physiologically acceptable salt thereof.

5. A pharmaceutical composition containing a compound according to claim 1, 2, 3 or 4 together with one or more inert carriers and/or diluents.

6. A method for treating carcinoma, sarcoma or leukaemia, psoriasis or rheumatoid arthritis which method comprises administering to a host in need of such treatment a therapeutic amount of a compound in accordance with claim 1, 2, 3 or 4.

* * * * *

UNITED STATES PATENT AND TRADEMARK OFFICE
CERTIFICATE OF CORRECTION

| | | |
|---|---|---|
| PATENT NO. | : 6,362,210 B1 | Page 1 of 1 |
| DATED | : March 26, 2002 | |
| INVENTOR(S) | : Norbert Hauel, Henning Priepke, Klaus Damm and Andreas Schnapp | |

It is certified that error appears in the above-identified patent and that said Letters Patent is hereby corrected as shown below:

<u>Column 90,</u>
Line 41, change "$R_4$ denotes a hydrogen atom," to -- $R_3$ denotes a hydrogen atom, --.

Signed and Sealed this

Seventh Day of January, 2003

JAMES E. ROGAN
*Director of the United States Patent and Trademark Office*